(12) United States Patent
Jantz et al.

(10) Patent No.: US 11,278,632 B2
(45) Date of Patent: Mar. 22, 2022

(54) ENGINEERED NUCLEASES USEFUL FOR TREATMENT OF HEMOPHILIA A

(71) Applicant: Precision BioSciences, Inc., Durham, NC (US)

(72) Inventors: Derek Jantz, Durham, NC (US); James Jefferson Smith, Morrisville, NC (US); Victor Bartsevich, Durham, NC (US); Clayton Beard, Durham, NC (US); Michael G. Nicholson, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 16/098,660

(22) PCT Filed: May 3, 2017

(86) PCT No.: PCT/US2017/030872
§ 371 (c)(1),
(2) Date: Nov. 2, 2018

(87) PCT Pub. No.: WO2017/192741
PCT Pub. Date: Nov. 9, 2017

(65) Prior Publication Data
US 2019/0142973 A1    May 16, 2019

Related U.S. Application Data

(60) Provisional application No. 62/331,335, filed on May 3, 2016.

(51) Int. Cl.
| | | |
|---|---|---|
| C12N 15/85 | (2006.01) | |
| A61K 48/00 | (2006.01) | |
| C07K 14/755 | (2006.01) | |
| C12N 9/22 | (2006.01) | |
| C12N 15/00 | (2006.01) | |
| C12N 15/90 | (2006.01) | |
| C12N 15/10 | (2006.01) | |
| A61P 7/04 | (2006.01) | |
| A61K 38/00 | (2006.01) | |
| A61K 38/46 | (2006.01) | |

(52) U.S. Cl.
CPC ........ *A61K 48/0066* (2013.01); *A61K 48/005* (2013.01); *A61K 48/0091* (2013.01); *A61P 7/04* (2018.01); *C07K 14/755* (2013.01); *C12N 9/22* (2013.01); *C12N 15/00* (2013.01); *C12N 15/102* (2013.01); *C12N 15/907* (2013.01); *C12Y 301/21001* (2013.01); *A61K 38/00* (2013.01); *A61K 38/465* (2013.01); *C12N 2750/14143* (2013.01); *C12Y 301/00* (2013.01)

(58) Field of Classification Search
None
See application file for complete search history.

(56) References Cited

U.S. PATENT DOCUMENTS

| | | |
|---|---|---|
| 4,873,192 A | 10/1989 | Kunkel |
| 6,015,832 A | 1/2000 | Baker, Jr. et al. |
| 6,506,803 B1 | 1/2003 | Baker, Jr. et al. |
| 6,559,189 B2 | 5/2003 | Baker, Jr. et al. |
| 6,635,676 B2 | 10/2003 | Baker, Jr. et al. |
| 8,021,867 B2 | 9/2011 | Smith et al. |
| 8,445,251 B2 | 5/2013 | Smith et al. |
| 2002/0045667 A1 | 4/2002 | Baker, Jr. et al. |
| 2004/0043041 A1 | 3/2004 | Baker, Jr. et al. |
| 2016/0045575 A1* | 2/2016 | Howard ................ C12N 15/111 514/44 R |
| 2018/0021457 A1* | 1/2018 | Kim ......................... A61P 7/02 424/93.21 |
| 2020/0299658 A1 | 9/2020 | Hekele et al. |

FOREIGN PATENT DOCUMENTS

| | | |
|---|---|---|
| EP | 2 500 434 A1 | 9/2012 |
| WO | WO 02/12514 A2 | 2/2002 |
| WO | WO 2004/067753 A2 | 8/2004 |
| WO | WO 2007/047859 A2 | 4/2007 |
| WO | WO 2009/059195 A2 | 5/2009 |
| WO | WO 2009/095742 A1 | 8/2009 |
| WO | WO 2010/009147 A1 | 1/2010 |
| WO | WO 2012/167192 A2 | 12/2012 |
| WO | WO 2014/089541 A2 | 6/2014 |

(Continued)

OTHER PUBLICATIONS

Silva et al. (Current Gene Therapy, 2011, vol. 11, pp. 11-27).*
International Search Report and Written Opinion for Application No. PCT/US2017/030872 dated Jun. 28, 2017.
International Preliminary Report on Patentability for Application No. PCT/US2017/030872 dated Nov. 15, 2018.
Airenne et al., "Baculovirus: an insect-derived vector for diverse gene transfer applications," Mol. Ther. 21(4), 739-749 (2013).
Altschul et al., "Basic local alignment search tool," J. Mol. Biol. 215, pp. 403-410 (1990).
Altschul et al., "Gapped BLAST and PSI-BLAST: a new generation of protein database search programs," Nucleic Acids Res. 25, pp. 3389-3402 (1997).

(Continued)

*Primary Examiner* — Celine X Qian
(74) *Attorney, Agent, or Firm* — Wolf, Greenfield & Sacks, P.C.

(57) ABSTRACT

The present invention encompasses engineered nucleases which recognize and cleave a recognition sequence within the int22h-1 sequence of a Factor VIII gene. The present invention also encompasses methods of using such engineered nucleases to make genetically-modified cells, and the use of such cells in a pharmaceutical composition and in methods for treating hemophilia A. Further, the invention encompasses pharmaceutical compositions comprising engineered nuclease proteins, nucleic acids encoding engineered nucleases, or genetically-modified cells of the invention, and the use of such compositions for treating of hemophilia A.

16 Claims, 17 Drawing Sheets

Specification includes a Sequence Listing.

(56) References Cited

FOREIGN PATENT DOCUMENTS

WO     WO 2016/111546 A2     11/2017

OTHER PUBLICATIONS

Arnould et al., "Engineering of large numbers of highly specific homing endonucleases that induce recombination on novel DNA targets," J. Mol. Biol. 355, pp. 443-458 (2006).
Bagnall et al., Int22h-related inversions causing hemophilia A: a novel insight into their origin and a new more discriminant PCR test for their detection. J Thromb Haemost. Mar. 2006;4(3):591-8.
Belfort et al., Homing endonucleases: from genetic anomalies to programmable genomic clippers. Methods Mol Biol. 2014;1123:1-26. doi: 10.1007/978-1-62703-968-0_1. Author manuscript.
Benoist et al., "In vivo sequence requirements of the SV40 early promotor region," Nature 290(5804), pp. 304-310 (1981).
Beurdeley et al., "Compact designer TALENs for efficient genome engineering," Nat. Commun. 4, p. 1762 (2013).
Bolton-Maggs et al., Haemophilias A and B. Lancet. May 24, 2003;361(9371):1801-9.
Bowen, Haemophilia A and haemophilia B: molecular insights. Mol Pathol. Apr. 2002;55(2):127-44. Erratum in Mol Pathol Jun. 2002;55(3):208.
Cahill et al., "Mechanisms of eukaryotic DNA double strand break repair," Front. Biosci. 11, pp. 1958-1976 (2006).
Chames et al., "In vivo selection of engineered homing endonucleases using double-strand break induced homologous recombination," Nucleic Acids Res. 33, p. e178 (2005).
Chang et al., "Inducible retroviral vectors regulated by lac repressor in mammalian cells," Gene 183, pp. 137-142 (1996).
Chen et al., A novel adenoviral vector carrying an all-in-one Tet-On system with an autoregulatory loop for tight, inducible transgene expression. BMC Biotechnol. Feb. 13, 2015;15:4. doi: 10.1186/s12896-015-0121-4.
Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).
Cheng et al., "Dendrimers as drug carriers: applications in different routes of drug administration," J. Pharm. Sci. 97(1): 123-143 (2008).
Chevalier et al., Homing endonucleases: structural and functional insight into the catalysts of intron/intein mobility. Nucleic Acids Res. Sep. 15, 2001;29(18):3757-74.
Cots et al., "Helper dependent adenovirus vectors: progress and future prospects," Curr. Gene Ther. 13(5) pp. 370-381 (2013).
Deshayes et al., "Cell-penetrating peptides: tools for intracellular delivery of therapeutics," Cell Mol. Life Sci. 62, pp. 1839-1849 (2005).
Deshayes et al., "Primary amphipathic cell-penetrating peptides: structural requirements and interactions with model membranes," Biochemistry 43, pp. 7698-7706 (2004).
Dinda et al., "Nanobiotechnology-based drug delivery in brain targeting," Curr. Pharm. Biotechnol. 14, pp. 1264-1274 (2013).
Dingermann et al., "Establishment of a system for conditional gene expression using an inducible tRNA suppressor gene," Mol. Cell Biol. 12(9), pp. 4038-4045 (1992).
Durai et al., "Zinc finger nucleases: custom-designed molecular scissors for genome engineering of plant and mammalian cells," Nucleic Acids Res. 33, pp. 5978-5990 (2005).
Gao et al., "Efficient gene delivery into mammalian cells mediated by a recombinant baculovirus containing a whispovirus ie1 promoter, a novel shuttle promoter between insect cells and mammalian cells," J. Biotechnol. 131(2), pp. 138-143 (2007).
GenBank Submission; NIH/NCBI, Accession No. AY619999.1. Homo sapiens isolate Int22h-1 F8a gene, complete cds. Feb. 4, 2005. 3 pages.
Gish et al., "Identification of protein coding regions by database similarity search," Nature Genet. 3, pp. 266-272 (1993).

Grizot et al., "Efficient targeting of a SCID gene by an engineered single-chain homing endonuclease," Nucleic Acids Res. 37, pp. 5405-5419 (2009).
Haase, et al., "Generation of a tumor- and tissue-specific episomal non-viral vector system," BMC Biotechnol. 13, pp. 49-54 (2013).
Hudecz et al., "Medium-sized peptides as built in carriers for biologically active compounds," Med. Res. Rev. 25, pp. 679-736 (2005).
Jacox et al., "Tissue-specific and ubiquitous expression patterns from alternative promoters of human genes," PLoS One 5(8), p. e12274 (2010).
Jearawiriyapaisam et al., "Sustained dystrophin expression induced by peptide-conjugated morpholino oligomers in the muscles of mdx mice," Mol. Ther. 16, pp. 1624-1629 (2008).
Jiang et al., "Cationic core-shell liponanoparticles for ocular gene delivery," Biomaterials. 33(30), pp. 7621-7630 (2012).
Kang et al., "Harnessing the capacity of cell-penetrating peptides for drug delivery to the central nervous system," Curr. Pharm. Biotechnol. 15(3), pp. 220-230 (2014).
Kang et al., Thermoresponsive hydrogels as a new ocular drug delivery platform to the posterior segment of the eye. Trans Am Ophthalmol Soc. 2008;106:206-13; discussion 213-4.
Kramer et al., "In vitro and in vivo comparative study of chimeric liver-specific promoters," Mol. Ther. 7, pp. 375-385 (2003).
Kunkel et al., Rapid and efficient site-specific mutagenesis without phenotypic selection. Methods Enzymol. 1987;154:367-82.
Kunkel, "Rapid and efficient site-specific mutagenesis without phenotypic selection," Proc Natl Acad Sci U S A. Jan. 1985;82(2):488-92.
Lentz, et al., "Viral vectors for gene delivery to the central nervous system," Neurobiol. Dis. 48, pp. 179-188 (2012).
Li et al., "Generation of single-chain LAGLIDADG homing endonucleases from native homodimeric precursor proteins," Nucleic Acids• Res. 37, pp. 1650-1662 (2009).
Liu et al., "Therapeutic levels of factor IX expression using a muscle-specific promoter and adeno-associated virus serotype 1 vector," Hum. Gene Ther. 15, pp. 783-792 (2004).
Lozier et a., The Chapel Hill hemophilia A dog colony exhibits a factor VIII gene inversion. Proc Natl Acad Sci U S A. Oct. 1, 2002;99(20):12991-6. Epub Sep. 19, 2002.
Madden et al., "Applications of network BLAST server," Meth. Enzymol. 266, pp. 131-141 (1996).
Mak et al., "TAL effectors: function, structure, engineering and applications," Curr. Opin. Struct. Biol. 23, pp. 93-99 (2013).
Mali et al., "Cas9 as a versatile tool for engineering biology," Nat. Methods 10, pp. 957-963 (2013).
Martin et al., "Gene delivery to the eye using adeno-associated viral vectors," Methods 28, pp. 267-275 (2002).
Mastorakos et al., "Hydroxyl PAMAM dendrimer-based gene vectors for transgene delivery to human retinal pigment epithelial cells," Nanoscale 7(9), pp. 3845-3856 (2015).
McCall et al., "Pathogen-inspired drug delivery to the central nervous system," Tissue Barriers. 2(4), e944449; 12 pages (2014).
McCarty et al., "Self-complementary recombinant adeno-associated virus (scAAV) vectors promote efficient transduction independently of DNA synthesis," Gene Ther. 8, pp. 1248-1254 (2001).
Mishra et al., Recent applications of liposomes in ophthalmic drug delivery. J Drug Deliv. 2011;2011:863734. doi: 10.1155/2011/863734. Epub Mar. 1, 2011.
Park et al., Functional Correction of Large Factor VIII Gene Chromosomal Inversions in Hemophilia A Patient-Derived iPSCs Using CRISPR-Cas9. Cell Stem Cell. Aug. 6, 2015;17(2):213-20. doi: 10.1016/j.stem.2015.07.001. Epub Jul. 23, 2015.
Park et al., Targeted inversion and reversion of the blood coagulation factor 8 gene in human iPS cells using TALENs. Proc Natl Acad Sci U S A. Jun. 24, 2014;111(25):9253-8. doi: 10.1073/pnas.1323941111. Epub Jun. 9, 2014.
Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.
Ran et al., "Genome engineering using the CRISPR-Cas9 system," Nat. Protoc. 8, pp. 2281-2308 (2013).

(56) References Cited

OTHER PUBLICATIONS

Reyon et al., "FLASH assembly of TALENs for high-throughput genome editing," Nat Biotechnol. May 2012;30(5):460-5. doi: 10.1038/nbt.2170. Author manuscript.

Sands, AAV-mediated liver-directed gene therapy. Methods Mol Biol. 2011;807:141-57. doi: 10.1007/978-1-61779-370-7_6. Author manuscript.

Sauna et al., The intron-22-inverted F8 locus permits factor VIII synthesis: explanation for low inhibitor risk and a role for pharmacogenomics. Blood. Jan. 8, 2015;125(2):223-8. doi: 10.1182/blood-2013-12-530113. Epub Nov. 18, 2014.

Seligman et al., "Mutations altering the cleavage specificity of a homing endonuclease," Nucleic Acids Res. 30, pp. 3870-3879 (2002).

Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.

Sharma et al., "Next generation delivery system for proteins and genes of therapeutic purpose: why and how?" Biomed Res Int. 2014;2014:327950. doi: 10.1155/2014/327950. Epub Jul. 15, 2014.

Simeoni et al., "Insight into the mechanism of the peptide-based gene delivery system MPG: implications for delivery of siRNA into mammalian cells," Nucleic Acids Res. 31, pp. 2717-2724 (2003).

Sowa et al., "In vitro and in vivo testing of a novel regulatory system for gene therapy for intervertebral disc degeneration," Spine, 36(10), pp. E623-E628 (2011).

Stoddard, Homing endonuclease structure and function. Q Rev Biophys. Feb. 2005;38(1):49-95. Epub Dec. 9, 2005.

Sussman et al., "Isolation and characterization of new homing endonuclease specificities at individual target site positions," J. Mol. Biol. 342, pp. 31-41 (2004).

Tamboli et al., Polymeric vectors for ocular gene delivery. Ther Deliv. Apr. 2011;2(4):523-36. doi: 10.4155/tde.11.20.

Thomsen et al., "Promoter-regulatory region of the major immediate early gene of human cytomegalovirus," Proc. Natl. Acad. Sci. USA 81(3), pp. 659-663 (1984).

Tong et al., "Eye drop delivery of nano-polymeric micelle formulated genes with cornea-specific promoters," J. Gene Med. 9(11), pp. 956-966 (2007).

Vannucci et al., Viral vectors: a look back and ahead on gene transfer technology. New Microbiol. Jan. 2013;36(1):1-22. Epub Jan. 1, 2013.

Wu et al., In situ genetic correction of F8 intron 22 inversion in hemophilia A patient-specific iPSCs. Sci Rep. Jan. 8, 2016;6:18865. doi: 10.1038/srep18865.

Yuasa et al., "Adeno-associated virus vector-mediated gene transfer into dystrophin-deficient skeletal muscles evokes enhanced immune response against the transgene product," Gene Ther. 9, pp. 1576-1588 (2002).

Zhang et al., "A greedy algorithm for aligning DNA sequences," J. Comput. Biol. 7(1-2), pp. 203-214 (2000).

Zuris et al., "Efficient Delivery of Genome-Editing Proteins In Vitro and In Vivo," Nat. Biotechnol. 33, pp. 73-80 (2015). Author's manuscript. Published online Oct. 30, 2014. doi: 10.1038/nbt.3081.

International Search Report and Written Opinion for Application No. PCT/US2018/058692 dated Jan. 30, 2019.

International Preliminary Report on Patentability for Application No. PCT/US2018/058692 dated May 14, 2020.

\* cited by examiner

```
                              F8R1           F8R2
                            Half-Site       Half-Site F8R 1-2                  CCAGGCGCTGCATGCGCGTGAA      SEQ ID NO: 7
Recognition Sequence     GGTCCGCGACGTACGCGCACTT      SEQ ID NO: 8

F8R3           F8R4
                            Half-Site       Half-Site

F8R 3-4                  GCAGCAGCAGCACGCGGGACAC      SEQ ID NO: 9
Recognition Sequence     CGTCGTCGTCGTGCGCCCTGTG      SEQ ID NO:10

F8R9           F8R10
                            Half-Site       Half-Site

F8R 9-10                 CAGGATTGTGTGCAACTTCGGC      SEQ ID NO:11
Recognition Sequence     GTCCTAACACACGTTGAAGCCG      SEQ ID NO:12

F8R11          F8R12
                            Half-Site       Half-Site

F8R 11-12                CTGCAGGCTGTACAAGGCTTCT      SEQ ID NO:13
Recognition Sequence     GACGTCCGACATGTTCCGAAGA      SEQ ID NO:14

F8R13          F8R14
                            Half-Site       Half-Site

F8R 13-14                GGAGGACGGGTACCACGCCTTC      SEQ ID NO:15
Recognition Sequence     CCTCCTGCCCATGGTGCGGAAG      SEQ ID NO:16

F8R15          F8R16
                            Half-Site       Half-Site

F8R 15-16                GGCCGTCAGGTACTCAATAACC      SEQ ID NO:17
Recognition Sequence     CCGGCAGTCCATGAGTTATTGG      SEQ ID NO:18
```

Fig. 2

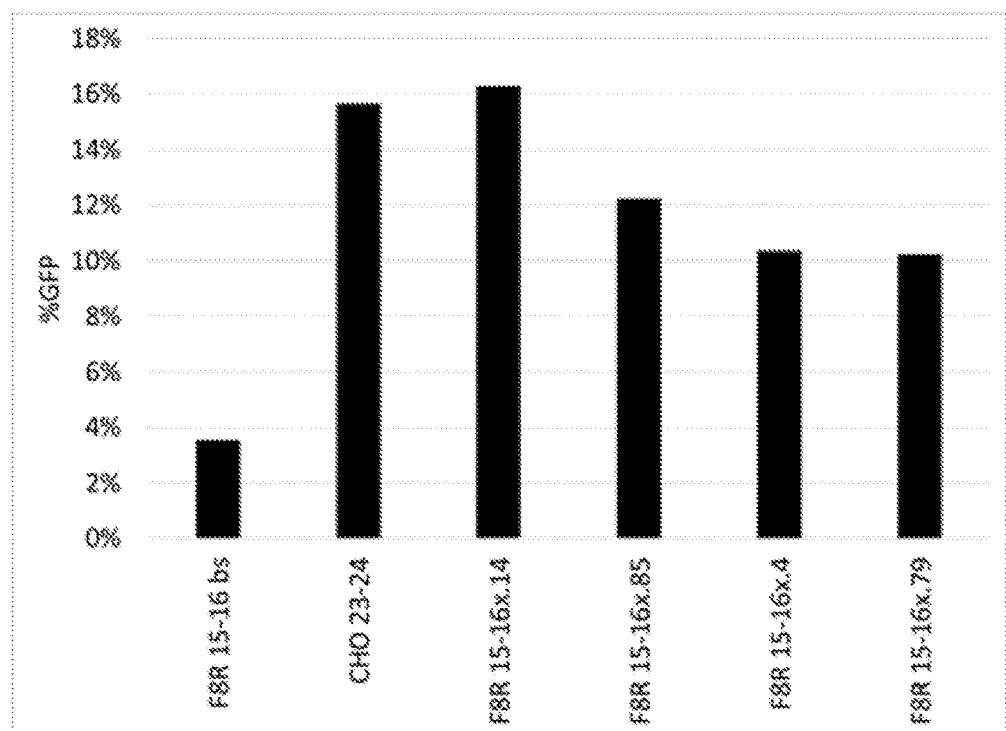

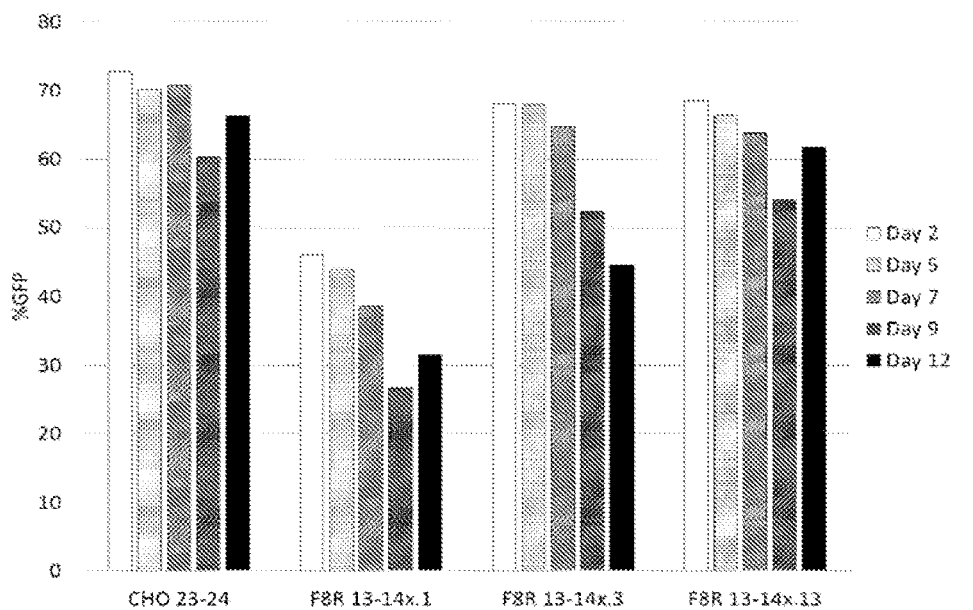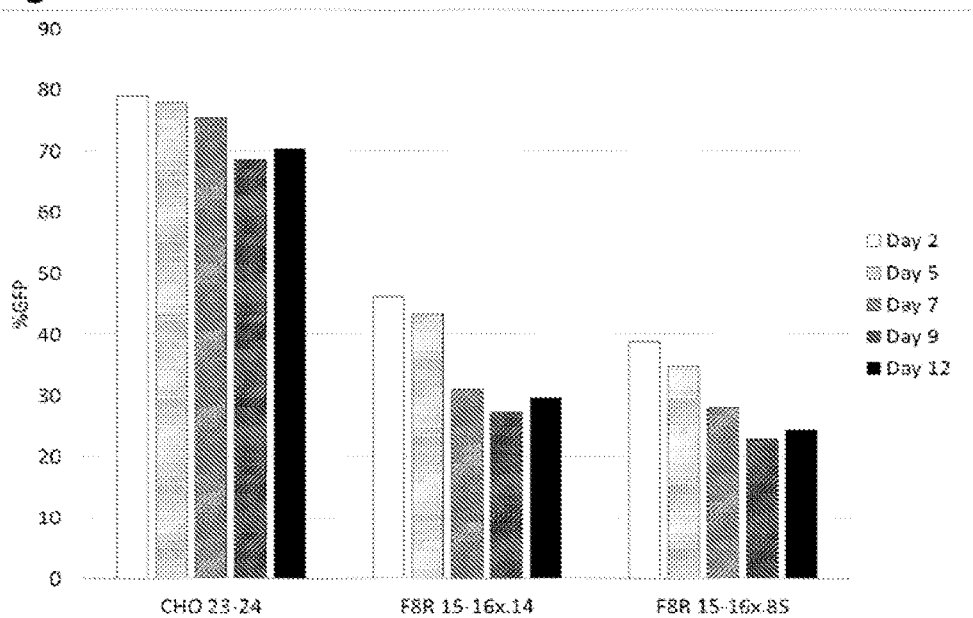

Primers H1R and H1F

Primers H1F and H2/3R lanes 1 and 4: molecular weight standard
lanes 2 and 5: human T-cells
lanes 3 and 6: human T-cells treated with F8R3-4x.43 nuclease

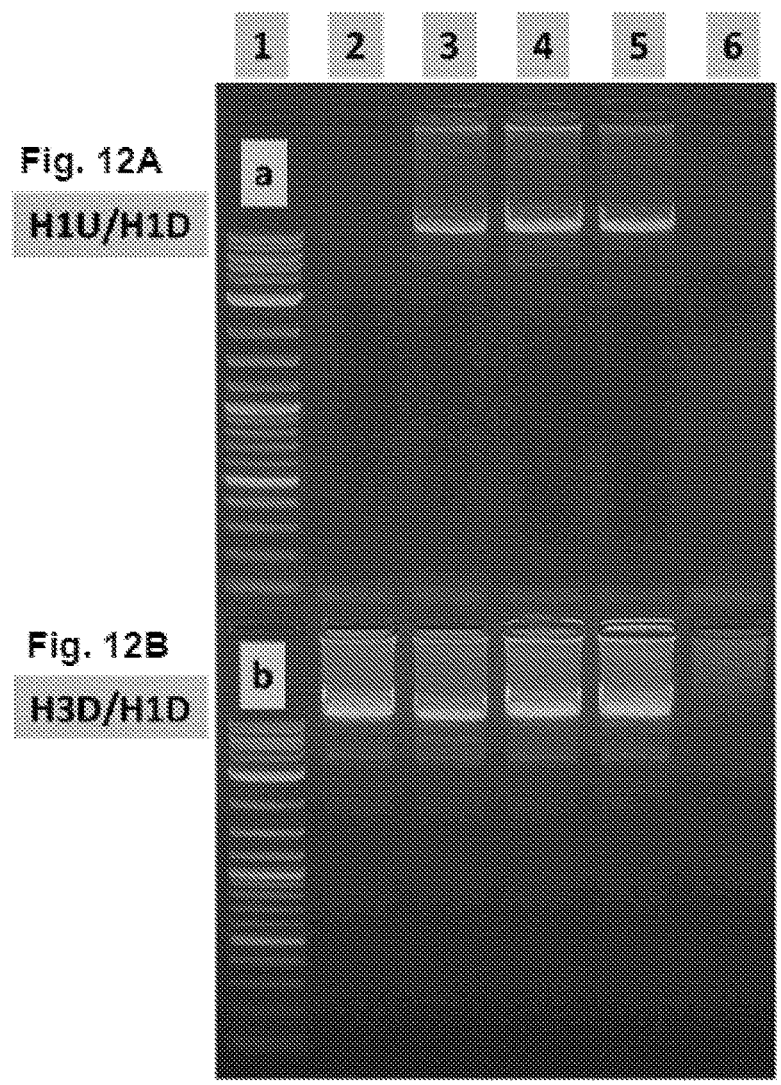
Fig. 12A H1U/H1D
Fig. 12B H3D/H1D
lanes 1a and 1b: molecular weight standard
lanes 2a and 2b: patient T-cells treated with GFP
lanes 3a and 3b: patient T-cells treated with F8R3-4x.43 nuclease
lanes 4a and 4b: patient T-cells treated with F8R11-12x.69 nuclease
lanes 5a and 5b: patient T-cells treated with F8R15-16x.14 nuclease
lanes 6a and 6b: no-template control

SEQUENCE LISTING

```
<160> NUMBER OF SEQ ID NOS: 96

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro
```

```
<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 9512
<212> TYPE: DNA
<213> ORGANISM: Homo sapiens

<400> SEQUENCE: 3
ttgaacagtc actgagcaac tactatgtcc tgggttctaa ttcagggctg ggcaaactat      60
agccccagaa tttggcccat agcctgcttt tgtacggact gtgagttaag aatagttttt     120
acacgttgaa aggattgcaa agacaaacat acaaagaaac aaagaagact gtgcaacaga     180
gaccacctgt ggtctgtaaa gactaacaca tttctatccc gcccttgaca gaaagagtct     240
gtgggctgct ggtctcctct aacggtggta gagatgcctg cacggttaac attaatcctt     300
ggcaccgaaa tcctcagcac ctaggaacca gatcttgcct aacacgctaa tttcagtctt     360
gaccaccttc ctccggcgta gcggttctca acgtctttg tctttgtact attcacgtat      420
aaaatattct ttcataagca acatttatcc ttttgggaat acctcacaat ggggagaagg     480
ggaaccccaa cagcctttaa gggttcactg cttcgctgcc accatttccg acggtttaca     540
ctgttttaag tgtgaatttg gaattgtttt caagttaaaa agcaaactaa tcatgtcctc     600
tgaaagtatt tgcttttggc atgctagaaa tcagtgttga cttttgatac tgatgtgata     660
cattacgagg gaattctcaa aactgctgaa atctggcctc ggcccagtta tcactgctct     720
taagcttctg agggagatac atgaatgagc ccacggcaaa tggaaaacga ggagttttag     780
tgtttcctag aattatgctc agatacccac tacctgaccg tctggttatc cttcccctca     840
cctccctgac gcaaggagtt tggaccagag cctaaggag cttctcctg aagcccaaat      900 cccaaactgg tcaccagtca tgctccgtaa ctcctgaacc tgacaagaag ccagccggcc     960
aggtctgcag cccgggttaa gaggagcata ccaggaaaga gccaaagagc aaggagcat     1020 gagcccttca accgctttta caataatttg ggctaggcgt tcagggctcc gtaggaccct    1080
tcctggcagc caagtgagag aaagaggaat gatggtggaa tgggcctctc ctgtgcttcc    1140
cattacttcc acactgtcga aatagaaata aagcagaaaa agaaccccct acaagtccca    1200
cccatttgga ggcactcaac tcacagtgac aaccctccac acctctcccc tgcaaaaaga    1260
cgcaaaacaa aaacacctac tccaaactgt gtccttacat ctcagccccg aagatcagga    1320 tgtgtgcaa cttcggccca aggatgcat ttccccaggg ttgaaagttt gagaaagagg      1380
ctatattctg aagagttctt gttgtcacca tcaaaaggat taaaaagacg caataaataa    1440
gaaaacagcg tagttggggg gcatgctcca tttgagccag aaagccttgg aaacttaagt    1500
gttctcaaac ggaacgccat cctgctttgg gggaacacgg aggctgcctt gcagtcacgt    1560
gatcgcacaa caccaagggg ccacgcactc tgatttcacc tacttaacta aaagttgcag    1620
caaaatccct attacaggcc aggcgtggtg gctcatgcct gtaatcccag cactttggga    1680
ggccgaggag ggtggatcat ttgaggtcag gagttggaga ccagcttggc caacatggtg    1740
agaccccatc tctattaaaa atacaaaaat tagcccagcg tggtggtgca cgcctgtaat    1800
cccaggcacc ctggaggttg aggtaggaga atcgcttgaa cccaggaggc ggaggttgca    1860
```

```
gtgagccgag atcacgccac tgcgctcctg cctgggcgac agagtgagac tccatctcgg    1920
ggaaaaaaaa aaaaaaaaa aaaaaaatcc ctattacaaa taaaagctgt tgtgatccag    1980
actgcatata cctctgcgaa tggaaccaga accgtgaatt ccaatgcaaa tcgatgcatc    2040
ggcaccagac ccgctgcact ggatgtatct gcattgcagt cacccgagta cggagcacat    2100
catagatgat ctctgcaggt tcgttgccca cataggaggc atagcgcaaa tttcaaagga    2160
acgaatacat cctggagccc aaacagctat ctggttctgc tgctggcctc ctgacaagta    2220
ggtaagagag tcacatttta tagacgacgg acaccaaaac cacacatgag gagtacaaga    2280
gtagctttat catggattta gggctgtggt tacaaggaag ctgtaaggaa taaaatgact    2340
cccatgaaga cgtaccgtgc ggacgagtgg aaggagaaat ttggccatta caaagacaca    2400
ggaatatgtt aagaagtgag gggcaggatg aaatcatcta gggtaggtat ttagagggag    2460
ggcgccgtgc aaaataaaat cctcactatg aaacaaaggc ggaggcagga ggctgcgtta    2520
ggtggaagca gcggaggaag gagacgaaag ggattgtcat tttcatgtcg tggcttttta    2580
gaagacagcc atgtcctcta ctctgattct atcaaaatgt gttctcgggg tgctggtaac    2640
gttcagccaa cgaaataatt cctatggcgg cagtaggaat aacaaaacgc agaagcggga    2700
acgatgtctt tttattcctc cccagacgca aacgtggatg catgaggttt ggtaacaggc    2760
aaagtcatct ggttaacgtg actgatgcaa aaagtccagg cctgggcaaa aagaagtcac    2820
tgggtgaatg ggatggatca gactccctgt cctgaggggg agatggtttc ttgcagaacg    2880
aggtgaagga ggtggttctg ctcagcagtc aacagtggcc acatctccac ctgcagcgac    2940
ttgatggctt ccgtgtcctt ttcgtgggta gccatgacca aagactggag cagcagaaag    3000
agctcctcgg gaagctggcc gctgctctcc tgcccgtggc tgtcaaaagc ctcccaggag    3060
tacttctcca gggtctgggc gtgctccggc agcagcttgg cgggcggtgg ttgcaggagg    3120
agcagcagca gcacgcggga cacctcgcag cggaccagca cgtccgagaa ggcgcccagg    3180
gcggcgggag agggcgccgc cgagccggag ttcgaggaa gcagcgcggc cggtagggcg    3240
ggcgtcgccc cgggcccggg ctggggtgcc ggcggcgggg gcggcggcag tgactgcacc    3300
gggtggctgc cgtgctcccg cgccaggcgc tgcatgcgcg tgaagaccgc cagggcgccg    3360
gtgtagtcgc gcgccagcag ctggcaggag gcggcctcgc caagcgcctg cagcgcggcc    3420
aggggcagct ggggcagctg gagctgggcg gcgcgctgga agtgaccggc ggcggcggcc    3480
ggctggccca ggtcgcgcag ggcggcggcc agctcgaggc agagggcggc ggcggcggcc    3540
ggctggccca gctcgaggtg cagacgcacc gcggcgccca gggcgctggc ggcggcctgc    3600
agcggctccc cgtaggcggc ggggcagacc aggcgctggc gcgcgtcgcg ctcctgccgc    3660
aggaagaggc gggcggcctc ggtgagggcc agcgcctccc cgggcccgtg aagagcgcg    3720 tgctggcagc gcgccaccgc cagctggcac caggccgcgt agggcagaca ctcctgggcg    3780
cgcagctccc ggcccagctg tccgaactgc tcgccggcct ccgccacgtt cggcttccgc    3840
aggaaccgct tcttcagctt gttcgatacc agccggtagc gggccaggaa gtccccggcc    3900
tcgggtcccg gccggcgcc gccgccgccc aggcctgcag ccgctgccgc catgctcgcc    3960
gccccaagca cttcccgacg cgccgccgca gctggcgggc gggccggggc ggggcgacgt    4020
gccctgcgtc ccctcggcg ggctgccgcc gtgcccgcgc cggctcccca gcccgagcct    4080
gccccttgcc ctgatgaggt gcaaagagcg ggatcggagg cggggcctgg ccgggctgtg    4140
agcggcgtat gcaaatcgag ggtctcgggg atgcggatcc aagaccctgg gaaggtacgc    4200
```

```
ggggcctggc ggggcaccag ctgctgctag ctcggctgca atgcaagtgg tctaggttgc    4260
taaaggcatc ccacagcctc tccatctgaa catgacccaa acgaaactcg tgaccctaat    4320
tccatgtctg cgcatttcta gactgttgtc cccccccccc cccgcccga ctactcagtc    4380 ctccgtcttc cggtccaggg ccccttgcca agcaccgggt ccacctctcc gtccccaccc    4440
cggttgcctt agaagtccgt cctgtcgcaa cactgcagtc atggtcttga ggcccacccg    4500
ccccaacgaa caccatcatg ctgaggactt tcccgggcag ccctgactt gctcagaacc     4560 agcgggggtg tccccttccc acccagggcc actccctgc actgtcaccc ggagagactg     4620
ctcctctgtg ccatccctgg ctcccaccca accccagacc cccaccacct ctccatccct    4680
ccagctgtgg aggtctcaca acccccaac ccatctcacc gccccccac ccccaccca      4740 aggcaaagtg actgaagcgg gcagatggct tccttgaaac attttattga cagaattaat    4800
gaaggcccaa gactttgggg cctgggttgt gggggaggg tgtttaaggc cggggggttca    4860 ggccggggga tttggggccg ggtgggtgga cgagtggacc tgtcaggtcc caggggccgg    4920
gtgtcagaag ctagtcctcg ccaggggcca cttgagagat ggtggtcgtg ttgaaaaggg    4980
tgctcagtag cctgtcgttg tgaaccacca tgtccagcag caggggagtg atgttccgct    5040
ctccgctgtt ctgggcctcg ttgcccgcca gctccggac cttggccgtc aggtactcaa     5100
taaccgcagc gaggtagacc ggcgccgtgc gactcaggcg ctgagcgtag tggccctccc    5160
gtagactgcg ctccacctgg ctcactgaaa acgaaagctc cgctcggacg gtgcgagagc    5220
aggtccgccc ccggccgcca gcaccggagg accctcggcg tctcctcctc ctcggcatgc    5280
tgggcgttga gtgtgctatc tcggcttggc ccagctaggc aagatggctc tcaagaggac    5340
agttaccgcg tccagtactg tgtatcctag cgaccagggc ccagcccctc attggctagg    5400
gagccgagac caatgggcac gcacatccgg cgacgggcac gcatgtggtg acggcccctc    5460
acaagggaca cacgtccgtc aggtgacctc atcactttcc cattggcctc gagggagcag    5520
gcctgggcct agaagtggct ggagggccgt gggggtgggg tggggcgggg caggggggaat    5580 cgcgctggtg accctctctt tgccagtggg aactttccct ttctactgga tgggaacacc    5640
gtgggaaaga caaaggggtg ggcgagggga ggacgggtac cacgccttca caatgttgca    5700
catccatcac gaccacctag ttccaaaacg ttttcaacac cccgaaaaga aaccgaaacc    5760
cctgtaccta taagcagtca cttgccgcac gcctccttcc acaccaccac taccagcccc    5820
cacaccctcc cacacacacc ccctgccccc gcccatacac acgttcccga tagtccctga    5880 caaccccctag tccatctgct ttctgtccat agaggttagc ctgttctgga gatttcctat    5940
agatggaatt atacgaccaa atgtgaggcc gtgtgtgtct ggctgctttc acttagcgta    6000
atggtttcat cagggtgcat ccatgtagag gcatgaatca ctacttcctt cctttgaatg    6060
actgagtacg attctgttgt atgaatagga ggccacattt tgtttaccca ctcgtcagtt    6120
gatggacagg ttatttcccc cttctggcta ttgtgagtgg cactgccatg accatctctc    6180
tacaggtttt tctttgaata tctcttttca gttcttttgg gtctatttct agcagtcaaa    6240
ctgctggctc gtgtggtaat tctgtttaac ttattgagga accaccaaac tgatttccac    6300
agcagctgta atcttcgca ttcccaacag tagtgcatga gagtcccaat tcttcacag      6360 cctcatcaaa acctgttttc tgtttgcctc attttgtttt gtttacagta gccatcctac    6420
tgggtgtcaa gtgctatctc atggtggttt tcattcgtat ttcccaaatg gctaatgatg    6480
ttgctgtggt ttgagtgcat ccccaaaatt gtgtgtcttg gaaacttaat ccccaaattc    6540
acatgttgat tggaggcgca gcctctgaga cggtaattag gattagataa ggtcatcggg    6600
```

```
gtgagacccc caggatgcga ctggtggctt tataagaata ggaagagagg cctgaaacga   6660
catacacgct cttgccctct cgccgtgtga taccctctgc cgtccccaga tgccgggtca   6720
cttcccagtc cccagaacgg taagaaataa atttcttttc tttataaatt gttcagtgtc   6780
gggtattcaa ttatggcaac agaaaacaga ctaagacatc ttttcatgtg cttcttggcc   6840
ctctgtacct ctgctttgga ggaatgtcta ttcaagccct tgcccattt tttaattcgg   6900 ttgattgtat tttggctgtg gcttctaaa acttattcat atattctgga aaatagactc   6960
ttatcagata tgtgacttgc aaatgtttct cccattcact ttctggatag agccctttgt   7020
tgcccaaaag atttacattt ggatgtagtc caacttgcca aatgaaaaga tatctgtggc   7080
tttgcctttg gtgtcatact gaaggagctg ttgcctaatc caaggtcgtg caaagttaca   7140
tctccgtttt cttcttagag ttttatagtt tcagcccta catttagatc tgtgatccat   7200
tttgaattaa ttctttacat gatgtgaggt aggggtccag gggccttctt ttgcatgtgg   7260
ctatccagtt gtcccagcgc agtttgttga ggggattatt cttcccctcc acccattgag   7320
gggtgccgga actcttactg aaaataaact ttacataaat atatgggttt attcctgact   7380
ctgagttctg taacattgac ctaatgtatc gatcacgatg gcagtaccac ccttttcgga   7440
ttactgcggt tttgtagtac gttttgaaat tgggaagtgt gagtccttca acttttttct   7500
tttctgagat tgttttggct atctgagccc cttacatttt cttatgaatt ttaggatcag   7560
cttgtcagtt tttacaaaga aggcaggttg gattctgaca ggcatcacga tgaatctgta   7620
tattgccttg gagattatgg gcatcttaac aatattaagt gtcccaatcc gttaacacaa   7680
aatgcctttc gatttattta ggtcttcttt aatttatttt agcaacgtct tgaaattttc   7740
agagtataca tcttgtacac ctttagttaa atttattcct cgacatttta ttgtttcgat   7800
gctactgtaa aatgaatcat ttccttaatc ttatttttcat gttattcatt gctagggtgt   7860
agaaatacaa ccgactgttg cagattgatc ttggatactg caactttgct gagccgaata   7920
tgctttgctg agcatactca gacagggttg gcatattagt ccgttcctac actgctataa   7980
agaactgcct gagaatgggt aattcctaaa gaaaagaggt ttaattgcct catggttctg   8040
caggctgtac aaggcttctg cttctgggca ggcctcagga aacgtgcaat catggcggaa   8100
ggcgaagggg aagcaagcac cttcttcaca tgttggagca ggaggaagag agagagaacg   8160
cacgcaaagg gggaagcgct gcacattttc aaacaatcat cagatcttgt gagcgctcta   8220
tcagaagaat agcaaggggg aagtccgccc ccatgattca atcacctccc actaggccct   8280
tccttcaaca ggtggggatt acaattcgac atgagatttg ggtggggaca cagagccaaa   8340
ccgtctcagt tttttttttt ttcttttgtt ggactcttta gtgtcctcta tataagaaca   8400
tgccatctat gcatctatga atagagatgg ttttacttgt tcctttccga tctggatgcc   8460
ttttatttct ttttcttgac taattgccct gactagaact ttgagtacga tgttgagtta   8520
caagtggcat tcctgatctt aggggaaat caaccagtct ttcaccatta agtatgatat   8580
tatctctggg tttttcatgg atgccctcta tcaggttgaa gaagtttctt tctgttcctg   8640
gtttgttgaa tttattttca tgaaagggta ctgcgttttg tcaaatgatc cttttttgtac   8700 atgattaaga tgaccatgag cccctcccc cgccccgct ccgccatgca ttctgttaat   8760
atggtgtatt ataaaattg attttcacat gttgaaccaa ccttacattt gtgggataaa   8820
tcctatttgg tcatagtgta taagagtgg tcaataaaca tttcgttgaa agaataggag   8880
tggatctggc aagcttcttg gaggacaatg tgtgtgttaa agaatctgta gcatgatgag   8940
```

| | |
|---|---|
| aagccaaggc accggtggga ggaggggagt tgcaaccaat tcattaaggc tggagagtac | 9000 |
| gatgccagtg gagcagtagt ggttgatgtg gctgggaaag aggtaggcag gagccaagac | 9060 |
| atggaggttc tattatgcca tgctcaggtt ttagaatacc ctgtaggcta cactgaaccc | 9120 |
| actgtggtct ttcagcttgg gagtgacgtg gtctgatttg cctctagaaa tatcaccctg | 9180 |
| gaagctgtgt ggagaataga acagagagga ttgtgtgtgg agaatagaac agagaggact | 9240 |
| gagattggaa ttagaaagct gctgtattat accagtcaag aaatgacaga tatctcaact | 9300 |
| aagacaatgg cattggtaga taagactagg ggacagagtc cataaaaagt ttaggtagta | 9360 |
| aaatggcaca cagtagacac tcactacata ttactcatac tggcgaacct agctggagac | 9420 |
| atgataattc atgtgctcat tcttcaaaaa atattgaagg gtagtgccag gtatactgtg | 9480 |
| ttaagcattg agacaacacc aacgagaaat at | 9512 |

<210> SEQ ID NO 4
<211> LENGTH: 13008
<212> TYPE: DNA
<213> ORGANISM: Canis lupus familiaris

<400> SEQUENCE: 4

| | |
|---|---|
| aagattttat ttttatttat ttgaaagaga gcatgagggg atccctgggt ggctcagcgg | 60 |
| tttagcgcct gcctttggcc cagggcgtga tcctggagac ccgggatcga gtcccacatc | 120 |
| aggctccttg catggagctt gcttctccct ctgcctgtgt ctccacctct ctctgtgtgt | 180 |
| ttctcatgaa taaataaata aattttcaaa agagagagag agcatgagta agagggagag | 240 |
| ggagagatag agaatctaaa gcagactctg tgctgagcag gaacccaaca cagggctcaa | 300 |
| tcccacgacc ctgagatcgt gacctgagcc aaaaacaaga gtcagatgct taaccaactg | 360 |
| agccacccag gcgcccctgg agttgttttc taactcatta atttctgttc aaaactttaa | 420 |
| aattttcttt tactttcttt cggttttgtc tttcctaaaa catggagttg aatgactagt | 480 |
| tcatttattt tcagtctttc tcattcagta tgataaaaga gttaactact ctcatgaagg | 540 |
| tcattcattt aataaacagt tactgagtaa ctgctatgtt ctagattcta gtacagagat | 600 |
| ggggaagcta gagcccatcc ttgaatttgg actaccactt gcttttgtac ggactgtgac | 660 |
| ttaagaatgg tttttacagg tttaaagttg caaaaacaaa cattatgcaa cgaagatcat | 720 |
| ttgtggcctg aaaagactaa aatattgcca tctggtcctt tacagaaagt ttgcagactg | 780 |
| ctggtctggc ctaaaggcag tagagatgcc taggcagtgc catgaagcag gactcttcat | 840 |
| ccccacagct tgcctaatgt gcagatttca atcttagtca tcgtccccca gtgtagtgat | 900 |
| tctcagatgt ttttatatct ttgttttgct cacagacaaa atcttgttca tcagagatat | 960 |
| ttcttatcat ggatgtccca cataaagagg gagaggggaa cctttaagga ccacagctac | 1020 |
| actgccaccg ttctcaatag tgtagaataa tgtaaatgtt aactttttta ttttttttaag | 1080 |
| atttatttat tcacgaaaga cacagagaga gaggcacaga cagaggcaga gggagaagca | 1140 |
| ggctccatgc agggagcccg acatgggact ccatcctggg gccccagcat cacgccctgg | 1200 |
| actaaaggcg gcgctaaacc gctgagccac ctgggctgcc ctaacttttt tatttttttaa | 1260 |
| aagattttac ttatttatcc atgagagaca cagagaggca gagacacagg cagagggagg | 1320 |
| agcaggcttc atgcagtgag cccgatgcgg gactcgatcc caggacccca ggatcatgac | 1380 |
| ctgagccaaa ggcagatgct cagccactga gccacccagg tgcccctgta tatgttaact | 1440 |
| ttgatatatc aatgaacatt tcagtgatgt ggcttttttct ctctggtttt caagttaaaa | 1500 |
| agaagagtat ttttaatgtc cttaaaaaat atttattttt ggttgtgtta gaaatcagtg | 1560 |

```
ttattttgac ataaagttga taattaccaa gggatttgtc aaagcctatg aaaattgcag    1620
aaatctagcc ttagcccagc tatctatgct ttgaagtttc tgagggagag ctataaagga    1680
gccaatgaca aatggaaaac aactttcatg ttttctaaaa ttatacttgt atacccaaca    1740
ccaggctctc tggcaaaccc tcccctctac atcctcaatg caaggagtta gaccagaggt    1800
ccaagggtgc ttttccttaa gcccaaaccc aaatactgcc accagtcaca tatcaaaact    1860
cctatacatt gttgttgtag tgatgtgatt tgaagtgagg tttgggagcc aatggcgaag    1920
aattcttgag actttttcag tgcaaaaaat gctgttttaa ttacagcaca gggacaggac    1980
ccatgggcag aaagacctgc actggggttg cgaggagtgg ctgattatgt aagattttcc    2040
atcctatgga ggggagggtg atgttaaggt cccaggaaat tgagtatagg gttcgggagg    2100
tctggctatt gatgattgct ttttttcctt gtaaatcatt aagacagttg caaactgatg    2160
gaagattcat gtcgtgcatg actgtgatct ctgtcagtta agcatttgtt tttcccttc     2220 ctttgctctt gggcagccag gagtgcctgc acaacatcac acctttccca cctggtgggt    2280
ggggtgggag ggggcagtt gttgcggagt attagcgtgt gctttaccct cagcttgcct     2340
tttgctccct catcaataag actactggcc agactgaggg gggcacttga cgggatgagc    2400
actgggtgtt actctagatg ttggcaaatt gaacaccaat aaaaaataaa tgtataaaaa    2460
aaaaaaagac tactggccag gcctgtagcc cgggttgaga gtataccaag aaaagtaaaa    2520
ctgcaaagga ccatgcaccc taaccacttt tttaaaaaat gttttcaaa aattccagta     2580 taattaatgt agtgttacat tagtttcagg tgtacaacat ggtgactcaa cacctctata    2640
catttcccag ggctcatgat gattacgtgc actcttaatc cccatcatgt atttcaccca    2700
tccccacacc tacaccccat ctggtgacca tcagtttctg gtctatattt aggagtctgg    2760
tttttttatc tcttttttt ctttcatctt ttgtttctta aattccacag gagtgaaatc      2820
atacagtatt tgtctttctc tgacttattt cacataacat tatacattct agatccatcc    2880
atgttgcaaa tggcaagatt gaattctttt tcagggctca aaaatactcc attttggatc    2940
tgtgtgtgtg tgtgtgtgtg tgtgtgtgtg tgtgtgtgtg tcttgatcct ttcatctatg    3000
gacacttgga ttgcttccat atattgactg ttgtaaataa tgctgctgta aacataggg      3060 tgtgtatctt tcttcgaatt agtgttctca ttttcgttgg gtaaataccc agttggggaa    3120
ttacatggtc atatggtggt tctattttta atttttaaag gaacctccat actatttcc     3180 acagtggccg caacagctgg cattcacacc aatagtgcat gaaggctcct ttttctccac    3240
atcctcacca acacctgtgc tttcctgtgg ttttgatttt agccattctg acagatgtga    3300
tatctcattg tggttttcac ttgcatttcc ctgatgatta gtgatgttga gcatcttttc    3360
atgtgtctga tacccaaca cttttgcaat aagttagact aggcttttag ggctccgaaa     3420
gacccttcca ggcagccacg tgagtgcgca ggactggtgg cggagtctgt gtcagatggg    3480 cctctttgt attttcttac ctactgactg cttccccgtt gctgaaatgg cggcatgagg     3540
actacctaac cgtcccaccc atttacaggc gcttaactca cggtgaccac cgcctacaca    3600
tcccccaaca cacacacaca ctaaaggcaa aacagaactg cccaaccgca tccttaaacc    3660
tcaccccacc agatcagttc cgtacacagc ctcaggctaa agggtgcatt ttccgaaagc    3720
agaaggactg agagggagat tacattctgg agagttctca ctggccctcc caaacccta     3780 aaggcaagtg gaatgtaaaa acacgcggct agtaacgttt gcacgcgaca tttgaccaa     3840 aaagccttga aaatgtagga ttctgaaaca ggatgctgtc ctcttgggca agaaaggcgc    3900
```

```
ggtctcgcag accgaggacc acgcaatagg tcggaagcac gctgattcaa cacatctgag    3960
ttacctacca gtggcgggaa ggcgcccagg acaagtaagt cccagcgtgg cccaggccca    4020
cgtctgagaa tggaacctag gcccacaacc ctgagttcca aggcacgcca gacacctcga    4080
cagtcgaacg tgggcccctg ctttgcgcag gacacattcg ccttggcgcc gaggaaggcc    4140
cacgcggcca aggttgtctg tggattgact gtgcggcaca gcccgagcag caggcgcacg    4200
gaccgctgcg agtgaacgac cacactgcgg cccgaagcac agccacccgc tcttcccctt    4260
gctgcctccc gacaggtgga gcagctattc cgcgttacgg aggaaggcga accgcaggcg    4320
agaggcatca gaacggcttt attgtggatt tagggcagca gccccgaggg cccgtgccat    4380
ctagtgctcc ccaggggtac gcgtggggcg tgggcaacaa aggagaacct gggtgagcac    4440
ctggagagac accggcctgc gctaaagcag atccccgacg aacaaaaaac ggaaccgaga    4500
ggcgtgtgca acatccaacc gtccgacttg caacagaggt gtacgggagg gtggggtgg    4560
gggtggggt gggggcccgc aggggagttg ggtgcaagaa gaggccaggg gtaaaggggc    4620
cgctcggtgt cccgtggccc gtcttgggga agagagccaa gtcctccagg ctgacccgt    4680
gatgctgggg tggttgccgc gccagggacg gcacgaagcc tgtgggatgc gggaggctgc    4740
agtcccgcag cgtccggtgg aggcgggcgg gcgaagagca agacaggtgc gagtgccggg    4800
cccctgcccg tcggtccgtg ggcaccgccg cccgccggcc ggccggccgg ccggccggcc    4860
ggcccgcggt ccaacggcgg ggcagcagca ggccacgggg ccagaggcgg aaagcggctt    4920
cggggctggc gcgcgcgagt ggtcagacgc cctgccccga cggggacacg cttcctgca    4980
gaacgaggtg cagcaggtgg ttctgctccg cactgagcag cggccacatg tccacctgca    5040
gcgacttgac ggcctccgtg tccttctcgt gggtggccat gaccagggac tggagcagca    5100
ggaacagctc gtcgggaagc tggccggcgc cgtcgggccc gtggccgtcg aaggcctccc    5160
aggagtactt ctccagcgtg tgggcgtgct cgggcagcag cttggcgggc ggcggctgca    5220
gcaggagcag cagcagcacg cgggacacct cgcagcggac cagcacgtcc gagaaggcgc    5280
ccagcgtggc gggcgcgggc gtgggcgtgg gcgcgggcgc ggcaggcagc agggcggcgg    5340
gcagggccgg ggcggcggcg gcggggccca gcggggcgga ggccgacgag gacgaggccg    5400
aggccgacga ggtcgaggcc gaggccgacg aggtcgacgc cgccgccggc ggggccaggg    5460
gcagcggcgg ggcgggcggc ggcggggccg gggcggctg ccgcagcggg tggctgccgt    5520
gctcccgcgc caggcgctgc atgcgcgtga agacggccag ggcgccgctg tagtcgcgcg    5580
ccagcagctg gcaggaggcg gcgtcgccca gcgcctgcag cgcggccagg gcagctgcg    5640
gcaggtgcag ctgcgcggcg cgcaggaagt ggccggcggc ggcggccggc tggcccaggt    5700
cgcgcagggc ggcggccagc tcgaggcaca gccggcggc ggcggccggc tggcccagct    5760
ccaggtgcag gcgcacggcg gcgcccagcg cgctggcggc ggcctgcagc ggctccccgt    5820
aggccgcggg gcaggcgagg cgctggcggg cgtcgcgctc ctgccgcagg aagaggcgcg    5880
cggcctcggt cagcgccagc gcctccccgg gcccgtggaa cagcgcctgc tggcagcgcg    5940
ccacggccag ctggcaccac gcggcgtacg gcaggcactc ctgcgcgcgc agctcccggc    6000
ccagctgcgc gaactgctcg cccgcctccg ccacgttcgg cttccgcagg aaccgcttac    6060
gcagcttgct cgacacctgc cggtagcggg ccaggaagtc cccggcctcg ggcccgggc    6120
ccgcgccgcc gccgccgccg ccgccgccgc ccccgggccg ccgccgccgc cgccgcccgc    6180
ggccgcccgc cgccgccgcc gccatcttgc ccgcacgcgc gcacgccga cgtgcccgcg    6240
tcccccggcc ccgccccctg cgggcccgcg cccccgcgg accccgcgca tgcgtgcgcc    6300
```

```
gcccccgcc  gtcccgccgg  acggaaccga  gcgcgcgggc  cggcgcgggg  cctgggcggc  6360
cgcggcctt  ccgaggcgac  cccggcccc   gggtcggccc  gcgcccccg   gccctcccg   6420
gccctgccg  gccccgagc   taacgtcgcg  gcgccggccc  gctggcccc   gaggccgctt  6480
ggccggagtc  aggatggtcc  ccgccccccc  agccttccgt  caaagccctg  tccctcgag   6540
tccgcgccgg  cacctgtgtc  ccccaacagt  ccgcgccggc  agctgtgtcc  ccccattcac  6600
tccgcgccgg  caggtgtgtc  ccctccatc   ccgcagccag  gttgttactg  caccggcgtt  6660
caccccatca  ccacgccgca  ggcatggtcc  tgagctccag  cccacacac   accatcgtcc  6720
acgggactgg  cccgtgcggt  ggggggggt   cttctatgcc  ccagcgtcac  tcccagccca  6780
gccaccccct  gtcctgaccc  cgagcagtcc  ccgtccccgc  accccagccg  accccacca   6840
ccacccctgc  accccagccg  gaccccgcca  cagcccccgt  ccctgcaccc  caacaatgct  6900
ccggaccgca  tgaccgaacc  ccgcaccaca  cccacgaacc  cgcgcccac   gccacacccc  6960
aaatcctcca  tcaccccat   cgtgcaccgc  cgagggcacc  ccaacccccc  gtcatccccg  7020
agccccgcac  ccccacccca  acctcgccca  aaccccaaa   ccccaacctc  ccccccgccc  7080
cccccgccc   tccccccgag  gcgcgtcccg  cacccagtga  gccaggcgca  cacgtctggt  7140
tgtctctgcg  cctttttattg  cggggacgcg  ggggtcaccg  agccccccg   gcggctcccc  7200
gggcggcggc  gggcatcagg  ggccggggc   ggctagtacc  gggccgggc   cacctgggac  7260
acggtggtca  tcgtgaacaa  gccgctgagc  agctcgtggt  tgtgcagcgc  ccggtccacg  7320
agctccgggg  tgatgtacgc  ggtgcgcctg  tgccggcct   cgtcgcccgc  cagccccagc  7380
acggtggccg  tcaggaactg  gatgacggcc  gccaggaaga  tggggcgga   cgcgcccagg  7440
cgcttggcgt  agcggccggc  ccgcaggagg  cgctccatct  ggcacacgga  gaaggccagc  7500
cccgcgcggg  cgctgcgcga  gcggcacgac  ctcgggcggc  cggcccgccc  tccacggctc  7560
ccctgagcc   gcgcgcgggg  cctcggcggc  gctcggcgcg  gggcctcggg  ctgcggcccg  7620
gctgcggccc  ggctggggac  gctcgggcgt  cgggccgcgg  agccacgggc  ctcgggctgc  7680
ggagaccccg  ggctgcggac  gctcgggcgt  cgggccgcgg  agccacgggc  ctcgggctgc  7740
ggagaccccg  ggctgcggac  ggtcgggcgt  cgggccgcgg  ggacatgggg  cttgggctgc  7800
agagacatcg  ggctgcggac  agagagacac  cggcctcggg  ctgcggagag  acggggcaag  7860
ggctgcagac  agacgggcct  caggctgcag  agagaccgac  ctcgggctgc  agagagaccg  7920
aactcgggct  gcagagtgtc  tgacctcggg  ctgcagagac  cgacctcggg  ctgcggagag  7980
acgggcctcg  ggctgcagaa  agtccgacct  cgggctgcag  agaccgacct  caggctgcgg  8040
agagacgggc  ctcgcgctgc  agagagaccg  acctcgggct  gtagagagac  tgacctcggg  8100
ctgcagagac  cgacctcggg  ctgcagagag  tccgacctcg  ggctgcagag  agtccgacct  8160
cgggctgcag  agagacgggc  ctcgggctgc  gctgccgaaa  cagcgtcggg  gcgcagagag  8220
gagcgccggg  gtgcaccgcc  gtgcggcgcg  ctggccggc   tgcacccgag  ccctcagcag  8280
cgggcgagga  ggccccgctc  cgtatccgag  ggacacaccc  cctccccgcc  ccgctgcgca  8340
cgcggtgaca  cgcaggcctg  atgaggtcac  cgcgtcccca  ttggcccggc  ccggccctcg  8400
cccgccagaa  aagccgctgg  cgggaagtcg  ctggctctgc  gccgcgcgga  cggcatgggg  8460
cgccaccgac  gagcgtgcag  gagctcgcgc  gccccacgt   gcaccccga   catgtcggcc  8520
ctctcggctg  cacacgcggc  accgcccgc   acagacggcc  cggccgccgc  gcgctcactg  8580
cccctgcac   cccgtcctgc  cccgggggac  cgaccgctcc  tcggcctcct  gtccctgccg  8640
```

```
cttggcgtcc gctggacacc tgctgcaggg gccaccctgg gaccagtagg tggccgtgtg    8700
cgccggccgc gttccctcgg caccgtgttc tcaggagggc tgttctctga gggagcggga    8760
accggggtcc ctccccccga gagagcagga atcgggcccc tcccctgag ggagcaggaa     8820
tcggggcacc ccccccagg gagcaggaat aacggcctct tccccccccc cagggagcag    8880
gaatcgggc ccctcccctc aagggagcag gagtcggggt ccctccccc cgagagagca     8940
ggaatcgggc ccctcccct gagggagcag gaatcgggt ccctcctccc gagggagcag     9000
gaatcgggc accccccccc ccagggagca ggaataacgg cctcttcccc cccccccccc   9060
cgggagcagg aatcgggccc cctccctcg agggagcagg aatccggac ccccaaggga    9120
gcgggaattg gggtccctcc gcccgaggga gcaaaagacg gaccctcggc tgcagaaaga   9180
cggacctcgg gctgcggaga gaccgacctc gggctgcgga gagaccaacc tcgggctgcg   9240
cttccgaaag acggcgtcgg ggcgcagaga ggagcgccgg ggtgcaccgc cgtgcggcgc   9300
gctgggccgg ctgctcccga gctctgagca gcgggcgagg aggccccgct ccgtataaaa   9360
gcgacacccc ctcccctccc cgctgcgcac gcggtgacac gcagatctga tgaggtcacc   9420
gcgtcctcat tggcccggcc ctcgcccgcc agaaaaggcg ggaagtcgct ggctctgcgc   9480
cgcgcggacg catggggcg ccacccacga gcgtgcagga gctcgcgcgc ccccacgtgc    9540
acccccgaca tgtcggccct ctcggctgca cacgcggcag cgccccgcac agacggcccg   9600
gccgccgcgc gctcactgcc ccctgcaccc cgtcctgccc cggggaccg accgctcctc    9660
ggcctcctgt ccctgccgct tggcgtccgc tggacacctg ctcaggggc caccctggga    9720
ccagtaggtg gccgtgtgcg ccggccgcgt tccctcggca ccgtgttctc aggagggctg   9780
ttctccgagg gagcgggaac ccgggtcccc cccccaagg gagcaggaat tggggtccct    9840
cccccgagc gatcaggaag cggggtccct ccaccaaggg acaggagtcg gggtccctcc    9900
ccccgaggga tcaggaatcg gggtccctcc accaagggat caggagttgg ggtccctccc   9960
ccaagggaca ggagtcaggg tccctccccc aagggacagg agtcgggtc cctccgccaa   10020
gggacaggag tcggggtccg tccccccgag ggagcaggaa taggcccccc gaggcagcgg   10080
ggatcgccct gcacgtccat cgaggggcac tcgccccac tgcgcgcccc ccctggcgga   10140
gaggggcacc tgcgggcgga cgtgcgcggc ggcggcggcg gcgaaggtcg cgcggggccc   10200
ctccgggcgc gggatggggg gcccgacggc agggcgacac ccgctgtctg ggcagcgcgc   10260
tgacccggcc ccctgctccc gccgcgccgc cccactggcc ctggcccgcg cctgctcctc   10320
ccggtgcggc ctcgcgagcc cccgcgcggg ctgtgccgcg gcacctggca cctgggggtc   10380
actgtccccc gtgtgtaggg aggggcaggg cggggcccga gggacaggga gctcgggcag   10440
ctgcagcccg ctgacccggg ccccgtgga gcctgcgggc tccccccgcg ccccaggggc    10500
tgccgacccg agcccgggct gcaggcgggc gcccagctga tccccccgc ccccccccc    10560
cccgggctgg gcctgtcgcg cccccgggtc ccgagcgccg cccgcggtg ccagcagcgg    10620
cgggtcggcg cggcgggagc gctgcaggtg cgccggacc gggcggggcc ctccctctgg    10680
gtgcccctcc aggcggcccc tgcactcggg ctgcgcaggg cggggcgggg gagcttcccg   10740
gagggggtgc ggcctgtctg tcgcctgggc gcgactcggc gatgggacac gttcaggtcc   10800
tgacaccggg ggggggggg ggagcggggg ggcttccgc gtattcgggg cctcccgagt     10860
gactttcagc aatgttccgt gactttccgt gcacacgccc tgcacgtcct ccgctacgtg   10920
tattcctagg gatgtaattg cacgtgatcc cgatttgaat aaaattattc aatcagttag   10980
ttaactgatc aattaatcag tttcgtttga ggttcgtcgc cgctgccgcg tggaaaaccc   11040
```

```
cctaatttct gcacgttggt ctcatatcct gaagtttgtt gaattcacta actctgccgg    11100
tgtttcgtga attctttagg acttttttctg tgtaaggtta tgtcatctga aacacagat    11160 ggttttcctt cttcctttcc aatttaaata ccctttattt ctttctcttg catcattgct    11220
ctagccagga tttccattac aatgtcggtt agaggcaggg aaagcgcgga ttcttgttcc    11280
tgattagggg aaaagctttc agtcctccac cagtgagtat gaccttagct atgggtattt    11340
cataaatgcc ctttattatg tttggtgatt ccccttctat tcctagtttg ctgagtgttt    11400
tttgtcagga aaaggtggat tttagtcaat gcttttttctg catgaatcaa gacagtcatg    11460 tgggttttttc cccctttatt ttattaacgt agagttattt tcttaagttg aagcatcttt    11520
gtattcctgg gacagttcct ttttggacat gaaatgtcac ttttataatg tactgctgga    11580
ttccgtctgc taaaatcatt tgaggatttc tgcacctata ttcttttta aagatttttt    11640 aggtactatt tgagagacca tgaatgatca gggggcggag ggagaggatg aagcagactc    11700
cccactgagc agggagcctg acgcgggcct cgatctcccg acccgggatc atgacctgag    11760
ctgaaagcgg atgcttcacc gactgagcca ccaggcaccc gggcaaaaca atttcttaca    11820
acattctgca cgatactgta atgctgatgt gtcatcatat aacacacact gattcctatt    11880
ctagtgtatt caagcataca caaagcctag gagatcattt taaactttcc gtagcctgta    11940
cgccatggtt taaaccgagg ccttctgagt aggtgttcct tttttattta aagattttat    12000
ttatttattc atgagagaca cagagagaga gagagaggca gagacccagg cagagggaga    12060
agcaggctcc atgcagggag cccgacgcgg ggctcgatcc caggtctcca ggttcatgcc    12120
ctgggccgaa ggcaggtgcc aagccactga gcccccagg gatcccctga ctaggtgttc    12180
ctatcacatt tctcaaactg tgttcccttt cctttgaaga tgccgtgtac tttctctgca    12240
ccctagactg ctcaaggtcc gaaccccac atgttggatg ttaacacgtg tcttacaaat    12300
ccatacacaa ggaatcatta attaaagcct cacagttcat gcacatgtgc acacacacac    12360
acacacagag agagaccaca gtcttggaag attatcctga ggccagggtg gtagggtggt    12420
gcctgccagc accctctcag atgtggaaca gggcccgaca tacaggactt ctagctacga    12480
cggttgtatg tgagcgctgc gtgctgtcga gagaagcaca aagcaaaatt agagggaaga    12540
tgcaatgggg agcaattgct ttgtaccctg tctgcacctg gcatgtacct gtgctaatcc    12600
ctccccacag gtcttctttg gcaacgtgga ttcatctggg atcaaacaca atattttttaa    12660 ccctccgatt attgctcagt acatccgttt gcacccaacc cattacagca tccgcagcac    12720
tcttcgcatg gagctcttgg gctgtgactt caacagtaag tgcccagtca tcacgtgccc    12780
ttccgtgtcc cagccccggg tgggatgaat gactgtccta gtcttctcga gggcagggcg    12840
atgtcccagg acacagaacc acgaatgcta agagcagcgc agtcccgagc aaacgcaggc    12900
cttggtcatt gtaaccatgg gattccctag gggcagccac ctcctccggc actcttaagg    12960
tcaaagtgcc cccgaactga gaagagctga ccagaaggcg cggggcag                13008

<210> SEQ ID NO 5
<211> LENGTH: 1116
<212> TYPE: DNA
<213> ORGANISM: Homo sapiens

<400> SEQUENCE: 5
atggcggcag cggctgcagg cctgggcggc ggcggcgccg gcccgggacc cgaggccggg    60
gacttcctgg cccgctaccg gctggtatcg aacaagctga agaagcggtt cctgcggaag    120
```

| | |
|---|---|
| ccgaacgtgg cggaggccgg cgagcagttc ggacagctgg gccgggagct gcgcgcccag | 180 |
| gagtgtctgc cctacgcggc ctggtgccag ctggcgtgg cgcgctgcca gcaggcgctc | 240 |
| ttccacgggc ccggggaggc gctggccctc accgaggccg cccgcctctt cctgcggcag | 300 |
| gagcgcgacg cgcgccagcg cctggtctgc cccgccgcct acggggagcc gctgcaggcc | 360 |
| gccgccagcg ccctgggcgc gcggtgcgt ctgcacctcg agctgggcca gccggccgcc | 420 |
| gccgccgccc tctgcctcga gctggccgcc gccctgcgcg acctgggcca gccggccgcc | 480 |
| gccgccggtc acttccagcg cgccgcccag ctccagctgc cccagctgcc cctggccgcg | 540 |
| ctgcaggcgc ttggcgaggc cgcctcctgc cagctgctgg cgcgcgacta caccggcgcc | 600 |
| ctggcggtct tcacgcgcat gcagcgcctg gcgcgggagc acggcagcca cccggtgcag | 660 |
| tcactgccgc cgcccccgcc gccggcaccc cagcccgggc ccggggcgac gcccgcccta | 720 |
| ccggccgcgc tgcttcctcc gaactccggc tcggcggcgc cctctcccgc cgccctgggc | 780 |
| gccttctcgg acgtgctggt ccgctgcgag gtgtcccgcg tgctgctgct gctcctcctg | 840 |
| caaccaccgc ccgccaagct gctgccggag cacgcccaga ccctgagaa gtactcctgg | 900 |
| gaggcttttg acagccacgg gcaggagagc agcggccagc ttcccgagga gctctttctg | 960 |
| ctgctccagt ctttggtcat ggctacccac gaaaaggaca cggaagccat caagtcgctg | 1020 |
| caggtggaga tgtggccact gttgactgct gagcagaacc acctccttca cctcgttctg | 1080 |
| caagaaacca tctccccctc aggacaggga gtctga | 1116 |

<210> SEQ ID NO 6
<211> LENGTH: 1349
<212> TYPE: DNA
<213> ORGANISM: Canis lupus familiaris

<400> SEQUENCE: 6

| | |
|---|---|
| atgcgcgggg tccgcggggg ggcggggccc gcaggggcg gggccggggg acgcgggcac | 60 |
| gtcgggcgtg cgcgcgtgcg ggcaagatgg cggcggcggc ggcgggcggc ccgggcggcg | 120 |
| gcggcggcgg cggcccgggc ggcggcggcg gcggcggcgg cggcggcgcg ggcccggggc | 180 |
| ccgaggccgg ggacttcctg gcccgctacc ggcaggtgtc gagcaagctg cgtaagcggt | 240 |
| tcctgcggaa gccgaacgtg gcggaggcgg gcgagcagtt cgcgcagctg ggccgggagc | 300 |
| tgcgcgcgca ggagtgcctg ccgtacgccg cgtggtgcca gctggccgtg gcgcgctgcc | 360 |
| agcaggcgct gttccacggg cccggggagg cgctggcgct gaccgaggcc gcgcgcctct | 420 |
| tcctgcggca ggagcgcgac gcccgccagc gcctcgcctg ccccgcggcc tacggggagc | 480 |
| cgctgcaggc cgccgccagc gcgctgggcg ccgccgtgcg cctgcacctg agctgggcc | 540 |
| agccggccgc cgccgccggc ctgtgcctcg agctggccgc cgccctgcgc gacctgggcc | 600 |
| agccggccgc cgccgccggc cacttcctgc gccgcgcgca gctgcacctg ccgcagctgc | 660 |
| ccctggccgc gctgcaggcg ctgggcgacg ccgcctcctg ccagctgctg gcgcgcgact | 720 |
| acagcggcgc cctggccgtc ttcacgcgca tgcagcgcct ggcgcgggag cacggcagcc | 780 |
| acccgctgcg gcagccgccc cggccccgc cgcccgcccgc ccgccgctg ccctggccc | 840 |
| cgccggcggc ggcgtcgacc tcgtcggcct cggcctcgac ctcgtcggcc tcggcctcgt | 900 |
| cctcgtcggc ctccgccccg ctgggcccg ccgccgccg ccggccctg cccgccgccc | 960 |
| tgctgcctgc cgccgcccgc cccacgccca cgccgcgcc cgccacgctg ggcgccttct | 1020 |
| cggacgtgct ggtccgctgc gaggtgtccc gcgtgctgct gctgctcctg ctgcagccgc | 1080 |
| cgcccgccaa gctgctgccc gagcacgccc acacgctgga gaagtactcc tgggaggcct | 1140 |

```
tcgacggcca cgggcccgac ggcgccggcc agcttcccga cgagctgttc ctgctgctcc    1200
agtccctggt catggccacc cacgagaagg acacggaggc cgtcaagtcg ctgcaggtgg    1260
acatgtggcc gctgctcagt gcggagcaga accacctgct gcacctcgtt ctgcaggaag    1320
ccgtgtcccc gtcggggcag ggcgtctga                                      1349

<210> SEQ ID NO 7
<211> LENGTH: 22
<212> TYPE: DNA
<213> ORGANISM: Homo sapiens

<400> SEQUENCE: 7
ccaggcgctg catgcgcgtg aa                                               22

<210> SEQ ID NO 8
<211> LENGTH: 22
<212> TYPE: DNA
<213> ORGANISM: Homo sapiens

<400> SEQUENCE: 8
ggtccgcgac gtacgcgcac tt                                               22

<210> SEQ ID NO 9
<211> LENGTH: 22
<212> TYPE: DNA
<213> ORGANISM: Homo sapiens

<400> SEQUENCE: 9
gcagcagcag cacgcgggac ac                                               22

<210> SEQ ID NO 10
<211> LENGTH: 22
<212> TYPE: DNA
<213> ORGANISM: Homo sapiens

<400> SEQUENCE: 10
cgtcgtcgtc gtgcgccctg tg                                               22

<210> SEQ ID NO 11
<211> LENGTH: 22
<212> TYPE: DNA
<213> ORGANISM: Homo sapiens

<400> SEQUENCE: 11
caggattgtg tgcaacttcg gc                                               22

<210> SEQ ID NO 12
<211> LENGTH: 22
<212> TYPE: DNA
<213> ORGANISM: Homo sapiens

<400> SEQUENCE: 12
gtcctaacac acgttgaagc cg                                               22

<210> SEQ ID NO 13
<211> LENGTH: 22
<212> TYPE: DNA
<213> ORGANISM: Homo sapiens

<400> SEQUENCE: 13
ctgcaggctg tacaaggctt ct                                               22
```

<210> SEQ ID NO 14
<211> LENGTH: 22
<212> TYPE: DNA
<213> ORGANISM: Homo sapiens

<400> SEQUENCE: 14
gacgtccgac atgttccgaa ga                                          22

<210> SEQ ID NO 15
<211> LENGTH: 22
<212> TYPE: DNA
<213> ORGANISM: Homo sapiens

<400> SEQUENCE: 15
ggaggacggg taccacgcct tc                                          22

<210> SEQ ID NO 16
<211> LENGTH: 22
<212> TYPE: DNA
<213> ORGANISM: Homo sapiens

<400> SEQUENCE: 16
cctcctgccc atggtgcgga ag                                          22

<210> SEQ ID NO 17
<211> LENGTH: 22
<212> TYPE: DNA
<213> ORGANISM: Homo sapiens

<400> SEQUENCE: 17
ggccgtcagg tactcaataa cc                                          22

<210> SEQ ID NO 18
<211> LENGTH: 22
<212> TYPE: DNA
<213> ORGANISM: Homo sapiens

<400> SEQUENCE: 18
ccggcagtcc atgagttatt gg                                          22

<210> SEQ ID NO 19
<211> LENGTH: 354
<212> TYPE: PRT
<213> ORGANISM: Artificial Sequence
<220> FEATURE:
<223> OTHER INFORMATION: Synthesized

<400> SEQUENCE: 19

Met Asn Thr Lys Tyr Asn Lys Glu Phe Leu Leu Tyr Leu Ala Gly Phe
1               5                   10                  15

Val Asp Gly Asp Gly Ser Ile Phe Ala Cys Ile Gln Pro Arg Gln Gln
            20                  25                  30

Ser Lys Phe Lys His Ser Leu Gln Leu Trp Phe Tyr Val Thr Gln Lys
        35                  40                  45

Thr Gln Arg Arg Trp Phe Leu Asp Lys Leu Val Asp Glu Ile Gly Val
    50                  55                  60

Gly Tyr Val Thr Asp Tyr Gly Ser Val Ser Asn Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Gly Gln Leu

```
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile His Ala Cys Ile Ser Pro Asp Gln Ala Cys
    210                 215                 220

Lys Phe Lys His Tyr Leu Arg Leu Arg Phe Tyr Val Ile Gln Lys Thr
225                 230                 235                 240

Gln Arg Arg Trp Phe Leu Asp Lys Leu Val Asp Glu Ile Gly Val Gly
                245                 250                 255

Tyr Val Glu Asp Ser Gly Ser Val Ser Arg Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 20
<211> LENGTH: 354
<212> TYPE: PRT
<213> ORGANISM: Artificial Sequence
<220> FEATURE:
<223> OTHER INFORMATION: Synthesized

<400> SEQUENCE: 20

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Thr Pro Ser Gln Val
            20                  25                  30

Met Lys Phe Lys His Gln Leu Arg Leu Arg Phe Tyr Val Ile Gln Lys
        35                  40                  45

Thr Gln Arg Arg Trp Phe Leu Asp Lys Leu Val Asp Glu Ile Gly Val
    50                  55                  60

Gly Tyr Val Glu Asp Ser Gly Ser Val Ser Arg Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
            195                 200                 205

Asp Gly Asp Gly Ser Ile Phe Ala Cys Ile Gln Pro Arg Gln Gln Ser
210                 215                 220

Lys Phe Lys His Ser Leu Gln Leu Trp Phe Tyr Val Thr Gln Lys Thr
225                 230                 235                 240

Gln Arg Arg Trp Phe Leu Asp Lys Leu Val Asp Glu Ile Gly Val Gly
                245                 250                 255

Tyr Val Asn Asp Trp Gly Gly Ala Ser Thr Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 21
<211> LENGTH: 354
<212> TYPE: PRT
<213> ORGANISM: Artificial Sequence
<220> FEATURE:
<223> OTHER INFORMATION: Synthesized

<400> SEQUENCE: 21

Met Asn Thr Lys Tyr Asn Lys Glu Phe Leu Leu Tyr Leu Ala Gly Phe
1               5                   10                  15

Val Asp Gly Asp Gly Ser Ile His Ala Cys Ile Ser Pro Asp Gln Ala
            20                  25                  30

Cys Lys Phe Lys His Tyr Leu Arg Leu Arg Phe Asn Val Ala Gln Lys
        35                  40                  45

Thr Gln Arg Arg Trp Phe Leu Asp Lys Leu Val Asp Glu Ile Gly Val
    50                  55                  60

Gly Tyr Val His Asp Gln Gly Ser Val Ser Tyr Tyr Gln Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Cys Ile Gln Pro Arg Gln Gln Ser
    210                 215                 220

Lys Phe Lys His Ser Leu Gln Leu Trp Phe Tyr Val Thr Gln Lys Thr
225                 230                 235                 240

Gln Arg Arg Trp Phe Leu Asp Lys Leu Val Asp Glu Ile Gly Ala Gly
                245                 250                 255

Tyr Val Asn Asp Trp Gly Gly Ala Ser Gln Tyr Arg Leu Ser Glu Ile
            260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 22
<211> LENGTH: 147
<212> TYPE: PRT
<213> ORGANISM: Artificial Sequence
<220> FEATURE:
<223> OTHER INFORMATION: Synthesized

<400> SEQUENCE: 22

Lys Glu Phe Leu Leu Tyr Leu Ala Gly Phe Val Asp Gly Asp Gly Ser
1               5                   10                  15

Ile His Ala Cys Ile Ser Pro Asp Gln Ala Cys Lys Phe Lys His Tyr
            20                  25                  30

Leu Arg Leu Arg Phe Tyr Val Ile Gln Lys Thr Gln Arg Arg Trp Phe
        35                  40                  45

Leu Asp Lys Leu Val Asp Glu Ile Gly Val Gly Tyr Val Glu Asp Ser
    50                  55                  60

Gly Ser Val Ser Arg Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
```

```
            115                 120                 125
Leu Asn Asp Ser Lys Thr Arg Lys Thr Thr Ser Glu Thr Val Arg Ala
        130                 135                 140
Val Leu Asp
145

<210> SEQ ID NO 23
<211> LENGTH: 147
<212> TYPE: PRT
<213> ORGANISM: Artificial Sequence
<220> FEATURE:
<223> OTHER INFORMATION: Synthesized

<400> SEQUENCE: 23

Lys Glu Phe Leu Leu Tyr Leu Ala Gly Phe Val Asp Gly Asp Gly Ser
1               5                   10                  15

Ile Phe Ala Ser Ile Thr Pro Ser Gln Val Met Lys Phe Lys His Gln
            20                  25                  30

Leu Arg Leu Arg Phe Tyr Val Ile Gln Lys Thr Gln Arg Arg Trp Phe
        35                  40                  45

Leu Asp Lys Leu Val Asp Glu Ile Gly Val Gly Tyr Val Glu Asp Ser
    50                  55                  60

Gly Ser Val Ser Arg Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 24
<211> LENGTH: 147
<212> TYPE: PRT
<213> ORGANISM: Artificial Sequence
<220> FEATURE:
<223> OTHER INFORMATION: Synthesized

<400> SEQUENCE: 24

Lys Glu Phe Leu Leu Tyr Leu Ala Gly Phe Val Asp Gly Asp Gly Ser
1               5                   10                  15

Ile His Ala Cys Ile Ser Pro Asp Gln Ala Cys Lys Phe Lys His Tyr
            20                  25                  30

Leu Arg Leu Arg Phe Asn Val Ala Gln Lys Thr Gln Arg Arg Trp Phe
        35                  40                  45

Leu Asp Lys Leu Val Asp Glu Ile Gly Val Gly Tyr Val His Asp Gln
    50                  55                  60

Gly Ser Val Ser Tyr Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 25
<211> LENGTH: 147
<212> TYPE: PRT
<213> ORGANISM: Artificial Sequence
<220> FEATURE:
<223> OTHER INFORMATION: Synthesized

<400> SEQUENCE: 25

Lys Glu Phe Leu Leu Tyr Leu Ala Gly Phe Val Asp Gly Asp Gly Ser
1               5                   10                  15

Ile Phe Ala Cys Ile Gln Pro Arg Gln Gln Ser Lys Phe Lys His Ser
            20                  25                  30

Leu Gln Leu Trp Phe Tyr Val Thr Gln Lys Thr Gln Arg Arg Trp Phe
        35                  40                  45

Leu Asp Lys Leu Val Asp Glu Ile Gly Val Gly Tyr Val Thr Asp Tyr
    50                  55                  60

Gly Ser Val Ser Asn Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Gly Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 26
<211> LENGTH: 147
<212> TYPE: PRT
<213> ORGANISM: Artificial Sequence
<220> FEATURE:
<223> OTHER INFORMATION: Synthesized

<400> SEQUENCE: 26

Lys Glu Phe Leu Leu Tyr Leu Ala Gly Phe Val Asp Gly Asp Gly Ser
1               5                   10                  15

Ile Phe Ala Cys Ile Gln Pro Arg Gln Gln Ser Lys Phe Lys His Ser
            20                  25                  30

Leu Gln Leu Trp Phe Tyr Val Thr Gln Lys Thr Gln Arg Arg Trp Phe
        35                  40                  45

Leu Asp Lys Leu Val Asp Glu Ile Gly Val Gly Tyr Val Asn Asp Trp
    50                  55                  60

Gly Gly Ala Ser Thr Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 27
<211> LENGTH: 147
<212> TYPE: PRT
<213> ORGANISM: Artificial Sequence
<220> FEATURE:
<223> OTHER INFORMATION: Synthesized

<400> SEQUENCE: 27

Lys Glu Phe Leu Leu Tyr Leu Ala Gly Phe Val Asp Gly Asp Gly Ser
1               5                   10                  15

Ile Phe Ala Cys Ile Gln Pro Arg Gln Gln Ser Lys Phe Lys His Ser
            20                  25                  30

Leu Gln Leu Trp Phe Tyr Val Thr Gln Lys Thr Gln Arg Arg Trp Phe
        35                  40                  45

Leu Asp Lys Leu Val Asp Glu Ile Gly Ala Gly Tyr Val Asn Asp Trp
    50                  55                  60

Gly Gly Ala Ser Gln Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 28
<211> LENGTH: 354
<212> TYPE: PRT
<213> ORGANISM: Artificial Sequence
<220> FEATURE:
<223> OTHER INFORMATION: Synthesized

<400> SEQUENCE: 28

Met Asn Thr Lys Tyr Asn Lys Glu Phe Leu Leu Tyr Leu Ala Gly Phe
1               5                   10                  15

Val Asp Gly Asp Gly Ser Ile Tyr Ala Lys Ile Asp Pro Asn Gln Lys
            20                  25                  30

Ser Lys Phe Lys His Val Leu Arg Leu Arg Phe Asp Val Ala Gln Lys
        35                  40                  45

Thr Gln Arg Arg Trp Phe Leu Asp Lys Leu Val Asp Glu Ile Gly Val
    50                  55                  60

Gly Tyr Val Tyr Asp His Gly Ser Val Ser His Tyr Thr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
```

```
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
        195                 200                 205
Asp Gly Asp Gly Ser Ile Phe Ala Ser Ile Arg Pro Ser Gln Thr Met
    210                 215                 220
Lys Phe Lys His Gln Leu Arg Leu Gly Phe Glu Val Gly Gln Lys Thr
225                 230                 235                 240
Gln Arg Arg Trp Phe Leu Asp Lys Leu Val Asp Glu Ile Gly Val Gly
                245                 250                 255
Tyr Val Arg Asp Asn Gly Ser Val Ser Val Tyr Thr Leu Ser Glu Ile
            260                 265                 270
Lys Pro Leu His Asn Phe Leu Thr Gln Leu Gln Pro Phe Leu Lys Leu
        275                 280                 285
Lys Gln Lys Gln Ala Asn Leu Val Leu Lys Ile Ile Glu Gln Leu Pro
    290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 29
<211> LENGTH: 354
<212> TYPE: PRT
<213> ORGANISM: Artificial Sequence
<220> FEATURE:
<223> OTHER INFORMATION: Synthesized

<400> SEQUENCE: 29

Met Asn Thr Lys Tyr Asn Lys Glu Phe Leu Leu Tyr Leu Ala Gly Phe
1               5                   10                  15
Val Asp Gly Asp Gly Ser Ile Tyr Ala Arg Ile Arg Pro Asn Gln Arg
                20                  25                  30
Cys Lys Phe Lys His Ala Leu Cys Leu Thr Phe Ser Val Arg Gln Lys
            35                  40                  45
Thr Gln Arg Arg Trp Phe Leu Asp Lys Leu Val Asp Glu Ile Gly Val
        50                  55                  60
Gly Tyr Val Tyr Asp Ser Gly Ser Val Ser Glu Tyr Ser Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
            195                 200                 205

Asp Gly Asp Gly Ser Ile Phe Ala Ser Ile Arg Pro Ser Gln Thr Met
            210                 215                 220

Lys Phe Lys His Gln Leu Arg Leu Gly Phe Glu Val Gly Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Asn Gly Ser Val Ser Val Tyr Asp Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro

<210> SEQ ID NO 30
<211> LENGTH: 354
<212> TYPE: PRT
<213> ORGANISM: Artificial Sequence
<220> FEATURE:
<223> OTHER INFORMATION: Synthesized

<400> SEQUENCE: 30

Met Asn Thr Lys Tyr Asn Lys Glu Phe Leu Leu Tyr Leu Ala Gly Phe
1               5                   10                  15

Val Asp Gly Asp Gly Ser Ile Tyr Ala Lys Ile Asp Pro Asn Gln Lys
                20                  25                  30

Ser Lys Phe Lys His Val Leu Arg Leu Arg Phe Asp Val Ala Gln Lys
            35                  40                  45

Thr Gln Arg Arg Trp Phe Leu Asp Lys Leu Val Asp Glu Ile Gly Val
50                  55                  60

Gly Tyr Val Tyr Asp His Gly Ser Ala Ser His Tyr Gln Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Ser Ile Arg Pro Ser Gln Thr Met
    210                 215                 220

Lys Phe Lys His Gln Leu Arg Leu Gly Phe Glu Val Gly Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Asn Gly Ser Val Ser Val Tyr Thr Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 31
<211> LENGTH: 354
<212> TYPE: PRT
<213> ORGANISM: Artificial Sequence
<220> FEATURE:
<223> OTHER INFORMATION: Synthesized

<400> SEQUENCE: 31

Met Asn Thr Lys Tyr Asn Lys Glu Phe Leu Leu Tyr Leu Ala Gly Phe
1               5                   10                  15

Val Asp Gly Asp Gly Ser Ile Tyr Ala Lys Ile Ser Pro Val Gln Lys
                20                  25                  30

Ala Lys Phe Lys His Val Leu Arg Leu Arg Phe Asp Val Ala Gln Lys
            35                  40                  45

Thr Gln Arg Arg Trp Phe Leu Asp Lys Leu Val Asp Glu Ile Gly Val
        50                  55                  60

Gly Tyr Val Tyr Asp His Gly Ser Val Ser His Tyr Thr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
```

```
            115                 120                 125
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Ser Ile Arg Pro Ser Gln Thr Met
    210                 215                 220

Lys Phe Lys His Gln Leu Arg Leu Gly Phe Glu Val Gly Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Asn Gly Ser Val Ser Val Tyr Asp Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 32
<211> LENGTH: 147
<212> TYPE: PRT
<213> ORGANISM: Artificial Sequence
<220> FEATURE:
<223> OTHER INFORMATION: Synthesized

<400> SEQUENCE: 32

Lys Glu Phe Leu Leu Tyr Leu Ala Gly Phe Val Asp Gly Asp Gly Ser
1               5                   10                  15

Ile Phe Ala Ser Ile Arg Pro Ser Gln Thr Met Lys Phe Lys His Gln
            20                  25                  30

Leu Arg Leu Gly Phe Glu Val Gly Gln Lys Thr Gln Arg Arg Trp Phe
        35                  40                  45

Leu Asp Lys Leu Val Asp Glu Ile Gly Val Gly Tyr Val Arg Asp Asn
    50                  55                  60

Gly Ser Val Ser Val Tyr Thr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
            130                 135                 140

Val Leu Asp
145

<210> SEQ ID NO 33
<211> LENGTH: 147
<212> TYPE: PRT
<213> ORGANISM: Artificial Sequence
<220> FEATURE:
<223> OTHER INFORMATION: Synthesized

<400> SEQUENCE: 33

Lys Glu Phe Leu Leu Tyr Leu Ala Gly Phe Val Asp Gly Asp Gly Ser
1               5                   10                  15

Ile Phe Ala Ser Ile Arg Pro Ser Gln Thr Met Lys Phe Lys His Gln
            20                  25                  30

Leu Arg Leu Gly Phe Glu Val Gly Gln Lys Thr Gln Arg Arg Trp Phe
        35                  40                  45

Leu Asp Lys Leu Val Asp Glu Ile Gly Val Gly Tyr Val Arg Asp Asn
    50                  55                  60

Gly Ser Val Ser Val Tyr Asp Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 34
<211> LENGTH: 147
<212> TYPE: PRT
<213> ORGANISM: Artificial Sequence
<220> FEATURE:
<223> OTHER INFORMATION: Synthesized

<400> SEQUENCE: 34

Lys Glu Phe Leu Leu Tyr Leu Ala Gly Phe Val Asp Gly Asp Gly Ser
1               5                   10                  15

Ile Phe Ala Ser Ile Arg Pro Ser Gln Thr Met Lys Phe Lys His Gln
            20                  25                  30

Leu Arg Leu Gly Phe Glu Val Gly Gln Lys Thr Gln Arg Arg Trp Phe
        35                  40                  45

Leu Asp Lys Leu Val Asp Glu Ile Gly Val Gly Tyr Val Arg Asp Asn
    50                  55                  60

Gly Ser Val Ser Val Tyr Thr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
                115                 120                 125
Leu Asn Asp Ser Lys Thr Arg Lys Thr Thr Ser Glu Thr Val Arg Ala
            130                 135                 140
Val Leu Asp
145

<210> SEQ ID NO 35
<211> LENGTH: 147
<212> TYPE: PRT
<213> ORGANISM: Artificial Sequence
<220> FEATURE:
<223> OTHER INFORMATION: Synthesized

<400> SEQUENCE: 35

Lys Glu Phe Leu Leu Tyr Leu Ala Gly Phe Val Asp Gly Asp Gly Ser
1               5                  10                  15

Ile Phe Ala Ser Ile Arg Pro Ser Gln Thr Met Lys Phe Lys His Gln
            20                  25                  30

Leu Arg Leu Gly Phe Glu Val Gly Gln Lys Thr Gln Arg Arg Trp Phe
        35                  40                  45

Leu Asp Lys Leu Val Asp Glu Ile Gly Val Gly Tyr Val Arg Asp Asn
    50                  55                  60

Gly Ser Val Ser Val Tyr Asp Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 36
<211> LENGTH: 147
<212> TYPE: PRT
<213> ORGANISM: Artificial Sequence
<220> FEATURE:
<223> OTHER INFORMATION: Synthesized

<400> SEQUENCE: 36

Lys Glu Phe Leu Leu Tyr Leu Ala Gly Phe Val Asp Gly Asp Gly Ser
1               5                  10                  15

Ile Tyr Ala Lys Ile Asp Pro Asn Gln Lys Ser Lys Phe Lys His Val
            20                  25                  30

Leu Arg Leu Arg Phe Asp Val Ala Gln Lys Thr Gln Arg Arg Trp Phe
        35                  40                  45

Leu Asp Lys Leu Val Asp Glu Ile Gly Val Gly Tyr Val Tyr Asp His
    50                  55                  60

Gly Ser Val Ser His Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 37
<211> LENGTH: 147
<212> TYPE: PRT
<213> ORGANISM: Artificial Sequence
<220> FEATURE:
<223> OTHER INFORMATION: Synthesized

<400> SEQUENCE: 37

Lys Glu Phe Leu Leu Tyr Leu Ala Gly Phe Val Asp Gly Asp Gly Ser
1               5                   10                  15

Ile Tyr Ala Arg Ile Arg Pro Asn Gln Arg Cys Lys Phe Lys His Ala
            20                  25                  30

Leu Cys Leu Thr Phe Ser Val Arg Gln Lys Thr Gln Arg Arg Trp Phe
        35                  40                  45

Leu Asp Lys Leu Val Asp Glu Ile Gly Val Gly Tyr Val Tyr Asp Ser
50                  55                  60

Gly Ser Val Ser Glu Tyr Ser Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 38
<211> LENGTH: 147
<212> TYPE: PRT
<213> ORGANISM: Artificial Sequence
<220> FEATURE:
<223> OTHER INFORMATION: Synthesized

<400> SEQUENCE: 38

Lys Glu Phe Leu Leu Tyr Leu Ala Gly Phe Val Asp Gly Asp Gly Ser
1               5                   10                  15

Ile Tyr Ala Lys Ile Asp Pro Asn Gln Lys Ser Lys Phe Lys His Val
            20                  25                  30

Leu Arg Leu Arg Phe Asp Val Ala Gln Lys Thr Gln Arg Arg Trp Phe
        35                  40                  45

Leu Asp Lys Leu Val Asp Glu Ile Gly Val Gly Tyr Val Tyr Asp His
50                  55                  60

Gly Ser Ala Ser His Tyr Gln Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

-continued

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 39
<211> LENGTH: 147
<212> TYPE: PRT
<213> ORGANISM: Artificial Sequence
<220> FEATURE:
<223> OTHER INFORMATION: Synthesized

<400> SEQUENCE: 39

Lys Glu Phe Leu Leu Tyr Leu Ala Gly Phe Val Asp Gly Asp Gly Ser
1               5                   10                  15

Ile Tyr Ala Lys Ile Ser Pro Val Gln Lys Ala Lys Phe Lys His Val
            20                  25                  30

Leu Arg Leu Arg Phe Asp Val Ala Gln Lys Thr Gln Arg Arg Trp Phe
        35                  40                  45

Leu Asp Lys Leu Val Asp Glu Ile Gly Val Gly Tyr Val Tyr Asp His
    50                  55                  60

Gly Ser Val Ser His Tyr Thr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 40
<211> LENGTH: 354
<212> TYPE: PRT
<213> ORGANISM: Artificial Sequence
<220> FEATURE:
<223> OTHER INFORMATION: Synthesized

<400> SEQUENCE: 40

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Glu Pro Glu Gln Arg
            20                  25                  30

Tyr Lys Phe Lys His Arg Leu Arg Leu Tyr Phe Ile Val Ser Gln Lys
        35                  40                  45

Thr Gln Arg Arg Trp Phe Leu Asp Lys Leu Val Asp Glu Ile Gly Val
    50                  55                  60

Gly Tyr Val Ala Asp Leu Gly Ser Val Ser Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu

```
                  100                 105                 110
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ser Ile Glu Pro Arg Gln Lys Tyr
        210                 215                 220

Lys Phe Lys His Arg Leu Ala Leu Ile Phe Gln Val Thr Gln Lys Thr
225                 230                 235                 240

Gln Arg Arg Trp Phe Leu Asp Lys Leu Val Asp Glu Ile Gly Val Gly
                245                 250                 255

Tyr Val Arg Asp Thr Gly Ser Val Ser His Tyr Ala Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 41
<211> LENGTH: 354
<212> TYPE: PRT
<213> ORGANISM: Artificial Sequence
<220> FEATURE:
<223> OTHER INFORMATION: Synthesized

<400> SEQUENCE: 41

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Glu Pro Arg Gln Lys
            20                  25                  30

Tyr Lys Phe Lys His Arg Leu Ala Leu Ile Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser His Tyr Ala Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Tyr Leu Ala Gly Phe Val
        195                 200                 205

Asp Gly Asp Gly Ser Ile Phe Ala Ser Ile Glu Pro Glu Gln Arg Tyr
        210                 215                 220

Lys Phe Lys His Arg Leu Arg Leu Tyr Phe Ile Val Ser Gln Lys Thr
225                 230                 235                 240

Gln Arg Arg Trp Phe Leu Asp Lys Leu Val Asp Glu Ile Gly Val Gly
                245                 250                 255

Tyr Val Ser Asp Cys Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
        340                 345                 350

Ser Pro

<210> SEQ ID NO 42
<211> LENGTH: 354
<212> TYPE: PRT
<213> ORGANISM: Artificial Sequence
<220> FEATURE:
<223> OTHER INFORMATION: Synthesized

<400> SEQUENCE: 42

Met Asn Thr Lys Tyr Asn Lys Glu Phe Leu Tyr Leu Ala Gly Phe
1               5                   10                  15

Val Asp Gly Asp Gly Ser Ile Tyr Ala Ser Ile Cys Pro Ala Gln Lys
                20                  25                  30

Leu Lys Phe Lys His Glu Leu Arg Leu Trp Phe Asn Val Ala Gln Lys
        35                  40                  45

Thr Gln Arg Arg Trp Phe Leu Asp Lys Leu Val Asp Glu Ile Gly Val
    50                  55                  60

Gly Tyr Val Cys Asp Lys Gly Ser Val Ser Tyr Tyr Thr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110
```

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Thr Ile Pro Pro Asp Gln Ser His
    210                 215                 220

Lys Phe Lys His Arg Leu Arg Leu Trp Phe Val Thr Gln Lys Thr
225                 230                 235                 240

Gln Arg Arg Trp Phe Leu Asp Lys Leu Val Asp Glu Ile Gly Val Gly
                245                 250                 255

Tyr Val Ala Asp Leu Gly Ser Val Ser Glu Tyr Arg Leu Ser Gln Ile
            260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
                340                 345                 350

Ser Pro

<210> SEQ ID NO 43
<211> LENGTH: 354
<212> TYPE: PRT
<213> ORGANISM: Artificial Sequence
<220> FEATURE:
<223> OTHER INFORMATION: Synthesized

<400> SEQUENCE: 43

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Glu Pro Arg Gln Lys
            20                  25                  30

Tyr Lys Phe Lys His Arg Leu Ala Leu Ile Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Ala Gly Ser Val Ser His Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
```

```
                115                 120                 125
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Pro Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Phe Ala Ser Ile Glu Pro Glu Gln Arg Tyr
    210                 215                 220

Lys Phe Lys His Arg Leu Lys Leu Gln Phe Glu Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Asn Gly Ser Val Ser Phe Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 44
<211> LENGTH: 147
<212> TYPE: PRT
<213> ORGANISM: Artificial Sequence
<220> FEATURE:
<223> OTHER INFORMATION: Synthesized

<400> SEQUENCE: 44

Lys Glu Phe Leu Leu Tyr Leu Ala Gly Phe Val Asp Gly Asp Gly Ser
1               5                   10                  15

Ile Phe Ala Ser Ile Glu Pro Glu Gln Arg Tyr Lys Phe Lys His Arg
                20                  25                  30

Leu Arg Leu Tyr Phe Ile Val Ser Gln Lys Thr Gln Arg Arg Trp Phe
            35                  40                  45

Leu Asp Lys Leu Val Asp Glu Ile Gly Val Gly Tyr Val Ala Asp Leu
        50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

-continued

Leu Asn Asp Ser Lys Thr Arg Lys Thr Thr Ser Glu Thr Val Arg Ala
            130                 135                 140

Val Leu Asp
145

<210> SEQ ID NO 45
<211> LENGTH: 147
<212> TYPE: PRT
<213> ORGANISM: Artificial Sequence
<220> FEATURE:
<223> OTHER INFORMATION: Synthesized

<400> SEQUENCE: 45

Lys Glu Phe Leu Leu Tyr Leu Ala Gly Phe Val Asp Gly Asp Gly Ser
1               5                   10                  15

Ile Phe Ala Ser Ile Glu Pro Glu Gln Arg Tyr Lys Phe Lys His Arg
            20                  25                  30

Leu Arg Leu Tyr Phe Ile Val Ser Gln Lys Thr Gln Arg Arg Trp Phe
        35                  40                  45

Leu Asp Lys Leu Val Asp Glu Ile Gly Val Gly Tyr Val Ser Asp Cys
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 46
<211> LENGTH: 147
<212> TYPE: PRT
<213> ORGANISM: Artificial Sequence
<220> FEATURE:
<223> OTHER INFORMATION: Synthesized

<400> SEQUENCE: 46

Lys Glu Phe Leu Leu Tyr Leu Ala Gly Phe Val Asp Gly Asp Gly Ser
1               5                   10                  15

Ile Phe Ala Thr Ile Pro Pro Asp Gln Ser His Lys Phe Lys His Arg
            20                  25                  30

Leu Arg Leu Trp Phe Val Val Thr Gln Lys Thr Gln Arg Arg Trp Phe
        35                  40                  45

Leu Asp Lys Leu Val Asp Glu Ile Gly Val Gly Tyr Val Ala Asp Leu
    50                  55                  60

Gly Ser Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
                  115                 120                 125

Leu Asn Asp Ser Lys Thr Arg Lys Thr Thr Ser Glu Thr Val Arg Ala
    130                 135                 140

Val Leu Asp
145

<210> SEQ ID NO 47
<211> LENGTH: 147
<212> TYPE: PRT
<213> ORGANISM: Artificial Sequence
<220> FEATURE:
<223> OTHER INFORMATION: Synthesized

<400> SEQUENCE: 47

Lys Glu Phe Leu Leu Tyr Leu Ala Gly Phe Val Asp Gly Asp Gly Ser
1               5                   10                  15

Ile Phe Ala Ser Ile Glu Pro Glu Gln Arg Tyr Lys Phe Lys His Arg
            20                  25                  30

Leu Lys Leu Gln Phe Glu Val Tyr Gln Lys Thr Gln Arg Arg Trp Phe
        35                  40                  45

Leu Asp Lys Leu Val Asp Glu Ile Gly Val Gly Tyr Val Tyr Asp Asn
    50                  55                  60

Gly Ser Val Ser Phe Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 48
<211> LENGTH: 147
<212> TYPE: PRT
<213> ORGANISM: Artificial Sequence
<220> FEATURE:
<223> OTHER INFORMATION: Synthesized

<400> SEQUENCE: 48

Lys Glu Phe Leu Leu Tyr Leu Ala Gly Phe Val Asp Gly Asp Gly Ser
1               5                   10                  15

Ile Tyr Ala Ser Ile Glu Pro Arg Gln Lys Tyr Lys Phe Lys His Arg
            20                  25                  30

Leu Ala Leu Ile Phe Gln Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser His Tyr Ala Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 49
<211> LENGTH: 147
<212> TYPE: PRT
<213> ORGANISM: Artificial Sequence
<220> FEATURE:
<223> OTHER INFORMATION: Synthesized

<400> SEQUENCE: 49

Lys Glu Phe Leu Leu Tyr Leu Ala Gly Phe Val Asp Gly Asp Gly Ser
1               5                   10                  15

Ile Tyr Ala Ser Ile Glu Pro Arg Gln Lys Tyr Lys Phe Lys His Arg
            20                  25                  30

Leu Ala Leu Ile Phe Gln Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser His Tyr Ala Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 50
<211> LENGTH: 147
<212> TYPE: PRT
<213> ORGANISM: Artificial Sequence
<220> FEATURE:
<223> OTHER INFORMATION: Synthesized

<400> SEQUENCE: 50

Lys Glu Phe Leu Leu Tyr Leu Ala Gly Phe Val Asp Gly Asp Gly Ser
1               5                   10                  15

Ile Tyr Ala Ser Ile Cys Pro Ala Gln Lys Leu Lys Phe Lys His Glu
            20                  25                  30

Leu Arg Leu Trp Phe Asn Val Ala Gln Lys Thr Gln Arg Arg Trp Phe
        35                  40                  45

Leu Asp Lys Leu Val Asp Glu Ile Gly Val Gly Tyr Val Cys Asp Lys
    50                  55                  60

Gly Ser Val Ser Tyr Tyr Thr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 51
<211> LENGTH: 147
<212> TYPE: PRT
<213> ORGANISM: Artificial Sequence
<220> FEATURE:
<223> OTHER INFORMATION: Synthesized

<400> SEQUENCE: 51

Lys Glu Phe Leu Leu Tyr Leu Ala Gly Phe Val Asp Gly Asp Gly Ser
1               5                   10                  15

Ile Tyr Ala Ser Ile Glu Pro Arg Gln Lys Tyr Lys Phe Lys His Arg
            20                  25                  30

Leu Ala Leu Ile Phe Gln Val Thr Gln Lys Thr Gln Arg Arg Trp Phe
        35                  40                  45

Leu Asp Lys Leu Val Asp Glu Ile Gly Val Gly Tyr Val Arg Asp Ala
    50                  55                  60

Gly Ser Val Ser His Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 52
<211> LENGTH: 354
<212> TYPE: PRT
<213> ORGANISM: Artificial Sequence
<220> FEATURE:
<223> OTHER INFORMATION: Synthesized

<400> SEQUENCE: 52

Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Arg Pro Cys Gln Trp
            20                  25                  30

Gly Lys Phe Lys His Arg Leu Ser Leu Ser Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Thr Asp Ser Gly Ser Val Ser Asn Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu

```
                100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
            130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
            165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
            195                 200                 205
Asp Gly Asp Gly Ser Ile Tyr Ala Thr Ile Ile Pro Ser Gln Trp Arg
            210                 215                 220
Lys Phe Lys His Gln Leu Val Leu Arg Phe Thr Val Ala Gln Lys Thr
225                 230                 235                 240
Gln Arg Arg Trp Phe Leu Asp Lys Leu Val Asp Glu Ile Gly Val Gly
            245                 250                 255
Tyr Val His Asp Ala Gly Ser Val Ser Thr Tyr Tyr Leu Ser Glu Ile
            260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
            290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
            325                 330                 335
Glu Thr Val Arg Ala Val Leu Asp Ser Leu Ser Glu Lys Lys Lys Ser
            340                 345                 350
Ser Pro

<210> SEQ ID NO 53
<211> LENGTH: 354
<212> TYPE: PRT
<213> ORGANISM: Artificial Sequence
<220> FEATURE:
<223> OTHER INFORMATION: Synthesized

<400> SEQUENCE: 53

Met Asn Thr Lys Tyr Asn Lys Glu Phe Leu Leu Tyr Leu Ala Gly Phe
1               5                   10                  15
Val Asp Gly Asp Gly Ser Ile Trp Ala Ser Ile Ser Pro Leu Gln Cys
            20                  25                  30
Leu Lys Phe Lys His Arg Leu Tyr Leu Glu Phe Asn Val Thr Gln Lys
            35                  40                  45
Thr Gln Arg Arg Trp Phe Leu Asp Lys Leu Val Asp Glu Ile Gly Val
        50                  55                  60
Gly Tyr Val Arg Asp Thr Gly Ser Val Ser Gln Tyr Arg Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
```

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Tyr Leu Ala Gly Phe Val
            195                 200                 205

Asp Gly Asp Gly Ser Ile Tyr Ala Cys Ile Ile Pro Ser Gln Gly Arg
            210                 215                 220

Lys Phe Lys His Gln Leu Ile Leu Arg Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Ser Asp Thr Gly Ser Val Ser Thr Tyr Val Leu Ser Gln Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 54
<211> LENGTH: 354
<212> TYPE: PRT
<213> ORGANISM: Artificial Sequence
<220> FEATURE:
<223> OTHER INFORMATION: Synthesized

<400> SEQUENCE: 54

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Arg Pro Ser Gln Gln
            20                  25                  30

Met Lys Phe Lys His Arg Leu Leu Leu Glu Phe Asn Val Thr Gln Lys
        35                  40                  45

Thr Gln Arg Arg Trp Phe Leu Asp Lys Leu Val Asn Glu Ile Gly Val
    50                  55                  60

Gly Tyr Val Arg Asp Thr Gly Ser Val Ser Gln Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Cys Ala Val Ile Lys Pro Gln Gln Tyr Asn
210                 215                 220

Lys Phe Lys His Leu Leu Gln Leu Arg Phe Gln Val Ala Gln Lys Thr
225                 230                 235                 240

Gln Arg Arg Trp Phe Leu Asp Lys Leu Val Asp Glu Ile Gly Val Gly
                245                 250                 255

Tyr Val Ser Asp Ser Gly Ser Val Ser Gln Tyr Arg Leu Ser Gln Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 55
<211> LENGTH: 354
<212> TYPE: PRT
<213> ORGANISM: Artificial Sequence
<220> FEATURE:
<223> OTHER INFORMATION: Synthesized

<400> SEQUENCE: 55

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Arg Pro Ser Gln Gln
            20                  25                  30

Met Lys Phe Lys His Arg Leu Leu Leu Glu Phe Asn Val Thr Gln Lys
        35                  40                  45

Thr Gln Arg Arg Trp Phe Leu Asp Lys Leu Val Asn Glu Ile Gly Val
    50                  55                  60

Gly Tyr Val Arg Asp Thr Gly Ser Val Ser Gln Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
            115                 120                 125
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Tyr Ala Thr Ile Ile Pro Asn Gln Cys His
    210                 215                 220

Lys Phe Lys His Gln Leu Leu Leu Arg Phe Arg Val Tyr Gln Lys Thr
225                 230                 235                 240

Gln Arg Arg Trp Phe Leu Asp Lys Leu Val Asp Glu Ile Gly Val Gly
                245                 250                 255

Tyr Val Glu Asp Gln Gly Ser Val Ser Ser Tyr Thr Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 56
<211> LENGTH: 147
<212> TYPE: PRT
<213> ORGANISM: Artificial Sequence
<220> FEATURE:
<223> OTHER INFORMATION: Synthesized

<400> SEQUENCE: 56

Lys Glu Phe Leu Leu Tyr Leu Ala Gly Phe Val Asp Gly Asp Gly Ser
1               5                   10                  15

Ile Tyr Ala Cys Ile Arg Pro Cys Gln Trp Gly Lys Phe Lys His Arg
                20                  25                  30

Leu Ser Leu Ser Phe Gln Val Thr Gln Lys Thr Gln Arg Arg Trp Phe
            35                  40                  45

Leu Asp Lys Leu Val Asp Glu Ile Gly Val Gly Tyr Val Thr Asp Ser
        50                  55                  60

Gly Ser Val Ser Asn Tyr Arg Leu Ser Glu Ile Lys Pro Leu His Asn
65              70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
            130                 135                 140

Val Leu Asp
145

<210> SEQ ID NO 57
<211> LENGTH: 147
<212> TYPE: PRT
<213> ORGANISM: Artificial Sequence
<220> FEATURE:
<223> OTHER INFORMATION: Synthesized

<400> SEQUENCE: 57

Lys Glu Phe Leu Leu Tyr Leu Ala Gly Phe Val Asp Gly Asp Gly Ser
1               5                   10                  15

Ile Trp Ala Ser Ile Ser Pro Leu Gln Cys Leu Lys Phe Lys His Arg
            20                  25                  30

Leu Tyr Leu Glu Phe Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 58
<211> LENGTH: 147
<212> TYPE: PRT
<213> ORGANISM: Artificial Sequence
<220> FEATURE:
<223> OTHER INFORMATION: Synthesized

<400> SEQUENCE: 58

Lys Glu Phe Leu Leu Tyr Leu Ala Gly Phe Val Asp Gly Asp Gly Ser
1               5                   10                  15

Ile Tyr Ala Ser Ile Arg Pro Ser Gln Gln Met Lys Phe Lys His Arg
            20                  25                  30

Leu Leu Leu Glu Phe Asn Val Thr Gln Lys Thr Gln Arg Arg Trp Phe
        35                  40                  45

Leu Asp Lys Leu Val Asn Glu Ile Gly Val Gly Tyr Val Arg Asp Thr
    50                  55                  60

Gly Ser Val Ser Gln Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
                115                 120                 125
Leu Asn Asp Ser Lys Thr Arg Lys Thr Thr Ser Glu Thr Val Arg Ala
    130                 135                 140

Val Leu Asp
145

<210> SEQ ID NO 59
<211> LENGTH: 147
<212> TYPE: PRT
<213> ORGANISM: Artificial Sequence
<220> FEATURE:
<223> OTHER INFORMATION: Synthesized

<400> SEQUENCE: 59

Lys Glu Phe Leu Leu Tyr Leu Ala Gly Phe Val Asp Gly Asp Gly Ser
1               5                   10                  15

Ile Tyr Ala Ser Ile Arg Pro Ser Gln Gln Met Lys Phe Lys His Arg
            20                  25                  30

Leu Leu Leu Glu Phe Asn Val Thr Gln Lys Thr Gln Arg Arg Trp Phe
        35                  40                  45

Leu Asp Lys Leu Val Asn Glu Ile Gly Val Gly Tyr Val Arg Asp Thr
    50                  55                  60

Gly Ser Val Ser Gln Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 60
<211> LENGTH: 147
<212> TYPE: PRT
<213> ORGANISM: Artificial Sequence
<220> FEATURE:
<223> OTHER INFORMATION: Synthesized

<400> SEQUENCE: 60

Lys Glu Phe Leu Leu Tyr Leu Ala Gly Phe Val Asp Gly Asp Gly Ser
1               5                   10                  15

Ile Tyr Ala Thr Ile Ile Pro Ser Gln Trp Arg Lys Phe Lys His Gln
            20                  25                  30

Leu Val Leu Arg Phe Thr Val Ala Gln Lys Thr Gln Arg Arg Trp Phe
        35                  40                  45

Leu Asp Lys Leu Val Asp Glu Ile Gly Val Gly Tyr Val His Asp Ala
    50                  55                  60

Gly Ser Val Ser Thr Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 61
<211> LENGTH: 147
<212> TYPE: PRT
<213> ORGANISM: Artificial Sequence
<220> FEATURE:
<223> OTHER INFORMATION: Synthesized

<400> SEQUENCE: 61

Lys Glu Phe Leu Leu Tyr Leu Ala Gly Phe Val Asp Gly Asp Gly Ser
1               5                   10                  15

Ile Tyr Ala Cys Ile Ile Pro Ser Gln Gly Arg Lys Phe Lys His Gln
            20                  25                  30

Leu Ile Leu Arg Phe Thr Val Ala Gln Lys Thr Gln Arg Arg Trp Phe
        35                  40                  45

Leu Asp Lys Leu Val Asp Glu Ile Gly Val Gly Tyr Val Ser Asp Thr
    50                  55                  60

Gly Ser Val Ser Thr Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 62
<211> LENGTH: 147
<212> TYPE: PRT
<213> ORGANISM: Artificial Sequence
<220> FEATURE:
<223> OTHER INFORMATION: Synthesized

<400> SEQUENCE: 62

Lys Glu Phe Leu Leu Tyr Leu Ala Gly Phe Val Asp Gly Asp Gly Ser
1               5                   10                  15

Ile Cys Ala Val Ile Lys Pro Gln Gln Tyr Asn Lys Phe Lys His Leu
            20                  25                  30

Leu Gln Leu Arg Phe Gln Val Ala Gln Lys Thr Gln Arg Arg Trp Phe
        35                  40                  45

Leu Asp Lys Leu Val Asp Glu Ile Gly Val Gly Tyr Val Ser Asp Ser
    50                  55                  60

Gly Ser Val Ser Gln Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 63
<211> LENGTH: 147
<212> TYPE: PRT
<213> ORGANISM: Artificial Sequence
<220> FEATURE:
<223> OTHER INFORMATION: Synthesized

<400> SEQUENCE: 63

Lys Glu Phe Leu Leu Tyr Leu Ala Gly Phe Val Asp Gly Asp Gly Ser
1               5                   10                  15

Ile Tyr Ala Thr Ile Ile Pro Asn Gln Cys His Lys Phe Lys His Gln
            20                  25                  30

Leu Leu Leu Arg Phe Arg Val Tyr Gln Lys Thr Gln Arg Arg Trp Phe
        35                  40                  45

Leu Asp Lys Leu Val Asp Glu Ile Gly Val Gly Tyr Val Glu Asp Gln
    50                  55                  60

Gly Ser Val Ser Ser Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 64
<211> LENGTH: 354
<212> TYPE: PRT
<213> ORGANISM: Artificial Sequence
<220> FEATURE:
<223> OTHER INFORMATION: Synthesized

<400> SEQUENCE: 64

Met Asn Thr Lys Tyr Asn Lys Glu Phe Leu Leu Tyr Leu Ala Gly Phe
1               5                   10                  15

Val Asp Gly Asp Gly Ser Ile Tyr Ala Tyr Ile Gln Pro Arg Gln Thr
            20                  25                  30

Tyr Lys Phe Lys His Gln Leu Arg Leu Tyr Phe Asp Val Thr Gln Lys
        35                  40                  45

Thr Gln Arg Arg Trp Phe Leu Asp Lys Leu Val Asp Glu Ile Gly Val
    50                  55                  60

Gly Tyr Val Val Asp Ser Gly Ser Val Ser Asn Tyr Lys Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu

-continued

```
                    100                 105                 110
Pro Ser Ala Lys Glu Ser Pro Asp Lys Phe Leu Glu Val Cys Thr Trp
            115                 120                 125
Val Asp Gln Ile Ala Ala Leu Asn Asp Ser Lys Thr Arg Lys Thr Thr
        130                 135                 140
Ser Glu Thr Val Arg Ala Val Leu Asp Ser Leu Pro Gly Ser Val Gly
145                 150                 155                 160
Gly Leu Ser Pro Ser Gln Ala Ser Ser Ala Ser Ser Ala Ser Ser
                165                 170                 175
Ser Pro Gly Ser Gly Ile Ser Glu Ala Leu Arg Ala Gly Ala Gly Ser
            180                 185                 190
Gly Thr Gly Tyr Asn Lys Glu Phe Leu Leu Tyr Leu Ala Gly Phe Val
            195                 200                 205
Asp Gly Asp Gly Ser Ile Phe Ala Arg Ile Val Pro Ala Gln Thr Gly
        210                 215                 220
Lys Phe Lys His Asn Leu Arg Leu Ser Phe Ala Val Tyr Gln Lys Thr
225                 230                 235                 240
Gln Arg Arg Trp Phe Leu Asp Lys Leu Val Asp Glu Ile Gly Val Gly
                245                 250                 255
Tyr Val Ser Asp His Gly Ser Val Ser Ser Tyr His Leu Ser Glu Ile
                260                 265                 270
Lys Pro Leu His Asn Phe Leu Thr Gln Leu Gln Pro Phe Leu Lys Leu
            275                 280                 285
Lys Gln Lys Gln Ala Asn Leu Val Leu Lys Ile Ile Glu Gln Leu Pro
        290                 295                 300
Ser Ala Lys Glu Ser Pro Asp Lys Phe Leu Glu Val Cys Thr Trp Val
305                 310                 315                 320
Asp Gln Ile Ala Ala Leu Asn Asp Ser Lys Thr Arg Lys Thr Thr Ser
                325                 330                 335
Glu Thr Val Arg Ala Val Leu Asp Ser Leu Ser Glu Lys Lys Lys Ser
            340                 345                 350
Ser Pro

<210> SEQ ID NO 65
<211> LENGTH: 354
<212> TYPE: PRT
<213> ORGANISM: Artificial Sequence
<220> FEATURE:
<223> OTHER INFORMATION: Synthesized

<400> SEQUENCE: 65

Met Asn Thr Lys Tyr Asn Lys Glu Phe Leu Leu Tyr Leu Ala Gly Phe
1               5                   10                  15
Val Asp Gly Asp Gly Ser Ile Tyr Ala Arg Ile Gly Pro Leu Gln Gln
                20                  25                  30
Gly Lys Phe Lys His Ser Leu Arg Leu Thr Leu Ser Val Tyr Gln Lys
            35                  40                  45
Thr Gln Arg Arg Trp Phe Leu Asp Lys Leu Val Asp Glu Ile Gly Val
        50                  55                  60
Gly Tyr Val Thr Asp Ser Gly Ser Val Ser Gly Tyr His Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Tyr Leu Ala Gly Phe Val
        195                 200                 205

Asp Gly Asp Gly Ser Ile Tyr Ala Ser Ile Glu Pro Lys Gln Asn Arg
210                 215                 220

Lys Phe Lys His Gln Leu Arg Leu Tyr Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val His Asp Asn Gly Ser Val Ser Ser Tyr Lys Leu Ser Gln Ile
        260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
        340                 345                 350

Ser Pro

<210> SEQ ID NO 66
<211> LENGTH: 354
<212> TYPE: PRT
<213> ORGANISM: Artificial Sequence
<220> FEATURE:
<223> OTHER INFORMATION: Synthesized

<400> SEQUENCE: 66

Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Leu Pro Gln Gln Ser
                20                  25                  30

Gly Lys Phe Lys His Gly Leu Arg Leu Arg Phe Ser Val Tyr Gln Lys
            35                  40                  45

Thr Gln Arg Arg Trp Phe Leu Asp Lys Leu Val Asp Glu Ile Gly Val
    50                  55                  60

Gly Tyr Val Ser Asp His Gly Ser Val Ser Ser Tyr Thr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

-continued

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ser Ile His Pro Ser Gln Pro Lys
    210                 215                 220

Lys Phe Lys His Gln Leu Arg Leu Tyr Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val His Asp Asn Gly Ser Val Ser Ser Tyr Lys Leu Ser Glu Ile
            260                 265                 270

Lys Pro Leu His Asn Phe Leu Thr Gln Leu Gln Pro Phe Leu Lys Leu
    275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 67
<211> LENGTH: 354
<212> TYPE: PRT
<213> ORGANISM: Artificial Sequence
<220> FEATURE:
<223> OTHER INFORMATION: Synthesized

<400> SEQUENCE: 67

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Ser Ile Leu Pro Gln Gln Ser
            20                  25                  30

Gly Lys Phe Lys His Gly Leu Arg Leu Arg Phe Ser Val Tyr Gln Lys
        35                  40                  45

Thr Gln Arg Arg Trp Phe Leu Asp Lys Leu Val Asp Glu Ile Gly Val
    50                  55                  60

Gly Tyr Val Ser Asp His Gly Ser Val Ser Ser Tyr Thr Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
```

```
                115                 120                 125
Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Ser Ile Gln Pro Arg Gln Ser Tyr
            210                 215                 220

Lys Phe Lys His Gln Leu Arg Leu Ser Phe Asp Val Ser Gln Lys Thr
225                 230                 235                 240

Gln Arg Arg Trp Phe Leu Asp Lys Leu Val Asp Glu Ile Gly Val Gly
                245                 250                 255

Tyr Val Ala Asp Arg Gly Ser Val Ser Trp Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 68
<211> LENGTH: 147
<212> TYPE: PRT
<213> ORGANISM: Artificial Sequence
<220> FEATURE:
<223> OTHER INFORMATION: Synthesized

<400> SEQUENCE: 68

Lys Glu Phe Leu Leu Tyr Leu Ala Gly Phe Val Asp Gly Asp Gly Ser
1               5                   10                  15

Ile Tyr Ala Tyr Ile Gln Pro Arg Gln Thr Tyr Lys Phe Lys His Gln
            20                  25                  30

Leu Arg Leu Tyr Phe Asp Val Thr Gln Lys Thr Gln Arg Arg Trp Phe
        35                  40                  45

Leu Asp Lys Leu Val Asp Glu Ile Gly Val Gly Tyr Val Val Asp Ser
    50                  55                  60

Gly Ser Val Ser Asn Tyr Lys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

```
Leu Asn Asp Ser Lys Thr Arg Lys Thr Thr Ser Glu Thr Val Arg Ala
        130                 135                 140

Val Leu Asp
145

<210> SEQ ID NO 69
<211> LENGTH: 147
<212> TYPE: PRT
<213> ORGANISM: Artificial Sequence
<220> FEATURE:
<223> OTHER INFORMATION: Synthesized

<400> SEQUENCE: 69

Lys Glu Phe Leu Leu Tyr Leu Ala Gly Phe Val Asp Gly Asp Gly Ser
1               5                   10                  15

Ile Tyr Ala Ser Ile Glu Pro Lys Gln Asn Arg Lys Phe Lys His Gln
            20                  25                  30

Leu Arg Leu Tyr Phe Asp Val Thr Gln Lys Thr Gln Arg Arg Trp Phe
        35                  40                  45

Leu Asp Lys Leu Val Asp Glu Ile Gly Val Gly Tyr Val His Asp Asn
    50                  55                  60

Gly Ser Val Ser Ser Tyr Lys Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 70
<211> LENGTH: 147
<212> TYPE: PRT
<213> ORGANISM: Artificial Sequence
<220> FEATURE:
<223> OTHER INFORMATION: Synthesized

<400> SEQUENCE: 70

Lys Glu Phe Leu Leu Tyr Leu Ala Gly Phe Val Asp Gly Asp Gly Ser
1               5                   10                  15

Ile Tyr Ala Ser Ile His Pro Ser Gln Pro Lys Lys Phe Lys His Gln
            20                  25                  30

Leu Arg Leu Tyr Phe Asp Val Thr Gln Lys Thr Gln Arg Arg Trp Phe
        35                  40                  45

Leu Asp Lys Leu Val Asp Glu Ile Gly Val Gly Tyr Val His Asp Asn
    50                  55                  60

Gly Ser Val Ser Ser Tyr Lys Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
```

```
            115                 120                 125
Leu Asn Asp Ser Lys Thr Arg Lys Thr Thr Ser Glu Thr Val Arg Ala
    130                 135                 140

Val Leu Asp
145

<210> SEQ ID NO 71
<211> LENGTH: 147
<212> TYPE: PRT
<213> ORGANISM: Artificial Sequence
<220> FEATURE:
<223> OTHER INFORMATION: Synthesized

<400> SEQUENCE: 71

Lys Glu Phe Leu Leu Tyr Leu Ala Gly Phe Val Asp Gly Asp Gly Ser
1               5                   10                  15

Ile Phe Ala Ser Ile Gln Pro Arg Gln Ser Tyr Lys Phe Lys His Gln
            20                  25                  30

Leu Arg Leu Ser Phe Asp Val Ser Gln Lys Thr Gln Arg Arg Trp Phe
        35                  40                  45

Leu Asp Lys Leu Val Asp Glu Ile Gly Val Gly Tyr Val Ala Asp Arg
    50                  55                  60

Gly Ser Val Ser Trp Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 72
<211> LENGTH: 147
<212> TYPE: PRT
<213> ORGANISM: Artificial Sequence
<220> FEATURE:
<223> OTHER INFORMATION: Synthesized

<400> SEQUENCE: 72

Lys Glu Phe Leu Leu Tyr Leu Ala Gly Phe Val Asp Gly Asp Gly Ser
1               5                   10                  15

Ile Phe Ala Arg Ile Val Pro Ala Gln Thr Gly Lys Phe Lys His Asn
            20                  25                  30

Leu Arg Leu Ser Phe Ala Val Tyr Gln Lys Thr Gln Arg Arg Trp Phe
        35                  40                  45

Leu Asp Lys Leu Val Asp Glu Ile Gly Val Gly Tyr Val Ser Asp His
    50                  55                  60

Gly Ser Val Ser Ser Tyr His Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 73
<211> LENGTH: 147
<212> TYPE: PRT
<213> ORGANISM: Artificial Sequence
<220> FEATURE:
<223> OTHER INFORMATION: Synthesized

<400> SEQUENCE: 73

Lys Glu Phe Leu Leu Tyr Leu Ala Gly Phe Val Asp Gly Asp Gly Ser
1               5                   10                  15

Ile Tyr Ala Arg Ile Gly Pro Leu Gln Gln Gly Lys Phe Lys His Ser
            20                  25                  30

Leu Arg Leu Thr Leu Ser Val Tyr Gln Lys Thr Gln Arg Arg Trp Phe
        35                  40                  45

Leu Asp Lys Leu Val Asp Glu Ile Gly Val Gly Tyr Val Thr Asp Ser
50                  55                  60

Gly Ser Val Ser Gly Tyr His Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 74
<211> LENGTH: 147
<212> TYPE: PRT
<213> ORGANISM: Artificial Sequence
<220> FEATURE:
<223> OTHER INFORMATION: Synthesized

<400> SEQUENCE: 74

Lys Glu Phe Leu Leu Tyr Leu Ala Gly Phe Val Asp Gly Asp Gly Ser
1               5                   10                  15

Ile Tyr Ala Ser Ile Leu Pro Gln Gln Ser Gly Lys Phe Lys His Gly
            20                  25                  30

Leu Arg Leu Arg Phe Ser Val Tyr Gln Lys Thr Gln Arg Arg Trp Phe
        35                  40                  45

Leu Asp Lys Leu Val Asp Glu Ile Gly Val Gly Tyr Val Ser Asp His
50                  55                  60

Gly Ser Val Ser Ser Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 75
<211> LENGTH: 147
<212> TYPE: PRT
<213> ORGANISM: Artificial Sequence
<220> FEATURE:
<223> OTHER INFORMATION: Synthesized

<400> SEQUENCE: 75

Lys Glu Phe Leu Leu Tyr Leu Ala Gly Phe Val Asp Gly Asp Gly Ser
1               5                   10                  15

Ile Tyr Ala Ser Ile Leu Pro Gln Gln Ser Gly Lys Phe Lys His Gly
            20                  25                  30

Leu Arg Leu Arg Phe Ser Val Tyr Gln Lys Thr Gln Arg Arg Trp Phe
        35                  40                  45

Leu Asp Lys Leu Val Asp Glu Ile Gly Val Gly Tyr Val Ser Asp His
    50                  55                  60

Gly Ser Val Ser Ser Tyr Thr Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 76
<211> LENGTH: 354
<212> TYPE: PRT
<213> ORGANISM: Artificial Sequence
<220> FEATURE:
<223> OTHER INFORMATION: Synthesized

<400> SEQUENCE: 76

Met Asn Thr Lys Tyr Asn Lys Glu Phe Leu Leu Tyr Leu Ala Gly Phe
1               5                   10                  15

Val Asp Gly Asp Gly Ser Ile Phe Ala Cys Ile Leu Pro Lys Gln Ser
            20                  25                  30

His Lys Phe Lys His Thr Leu Ser Leu Arg Phe Thr Val Gly Gln Lys
        35                  40                  45

Thr Gln Arg Arg Trp Phe Leu Asp Lys Leu Val Asp Glu Ile Gly Val
    50                  55                  60

Gly Tyr Val Tyr Asp Leu Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
```

```
                100                 105                 110
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Ser Ile Arg Pro Arg Gln Gly Gly
210                 215                 220

Lys Phe Lys His Thr Leu Asp Leu Arg Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Gln Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 77
<211> LENGTH: 354
<212> TYPE: PRT
<213> ORGANISM: Artificial Sequence
<220> FEATURE:
<223> OTHER INFORMATION: Synthesized

<400> SEQUENCE: 77

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Gln Pro Arg Gln Ser
                20                  25                  30

Ala Lys Phe Lys His Gly Leu Ile Leu Trp Phe Thr Val Gly Gln Lys
            35                  40                  45

Thr Gln Arg Arg Trp Phe Leu Asp Lys Leu Val Asp Glu Ile Gly Ala
        50                  55                  60

Gly Tyr Val Ile Asp Leu Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
                100                 105                 110
```

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Phe Ala Ser Ile Arg Pro Arg Gln Gly Gly
            210                 215                 220

Lys Phe Lys His Thr Leu Asp Leu Arg Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Gln Tyr Arg Leu Ser Gln Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 78
<211> LENGTH: 354
<212> TYPE: PRT
<213> ORGANISM: Artificial Sequence
<220> FEATURE:
<223> OTHER INFORMATION: Synthesized

<400> SEQUENCE: 78

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Arg Pro Arg Gln Arg
            20                  25                  30

Pro Lys Phe Lys His Asp Leu Val Leu Trp Phe Thr Val Gly Gln Lys
            35                  40                  45

Thr Gln Arg Arg Trp Phe Leu Asp Lys Leu Val Asp Glu Ile Gly Ala
        50                  55                  60

Gly Tyr Val Leu Asp Leu Gly Gly Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

```
Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Tyr Ala Ser Ile Gln Pro Arg Gln Gly Arg
210                 215                 220

Lys Phe Lys His Ser Leu Glu Leu Lys Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Ser Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 79
<211> LENGTH: 354
<212> TYPE: PRT
<213> ORGANISM: Artificial Sequence
<220> FEATURE:
<223> OTHER INFORMATION: Synthesized

<400> SEQUENCE: 79

Met Asn Thr Lys Tyr Asn Lys Glu Phe Leu Leu Tyr Leu Ala Gly Phe
1               5                   10                  15

Val Asp Gly Asp Gly Ser Ile Phe Ala Thr Ile Trp Pro Arg Gln Ser
            20                  25                  30

Ala Lys Phe Lys His Gln Leu Val Leu Trp Phe Ala Val Gly Gln Lys
        35                  40                  45

Thr Gln Arg Arg Trp Phe Leu Asp Lys Leu Val Asp Glu Ile Gly Ala
    50                  55                  60

Gly Tyr Val Val Asp Ala Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
            115                 120                 125
Val Asp Gln Ile Ala Ala Leu Asn Asp Ser Lys Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
                195                 200                 205

Asp Gly Asp Gly Ser Ile Tyr Ala Ser Ile Gln Pro Arg Gln Gly Arg
                210                 215                 220

Lys Phe Lys His Ser Leu Glu Leu Lys Phe Asp Val Thr Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Ser Gly Ser Val Ser Ser Tyr Arg Leu Ser Gln Ile
                260                 265                 270

Lys Pro Leu His Asn Phe Leu Thr Gln Leu Gln Pro Phe Leu Lys Leu
                275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
                340                 345                 350

Ser Pro

<210> SEQ ID NO 80
<211> LENGTH: 147
<212> TYPE: PRT
<213> ORGANISM: Artificial Sequence
<220> FEATURE:
<223> OTHER INFORMATION: Synthesized

<400> SEQUENCE: 80

Lys Glu Phe Leu Leu Tyr Leu Ala Gly Phe Val Asp Gly Asp Gly Ser
1               5                   10                  15

Ile Phe Ala Ser Ile Arg Pro Arg Gln Gly Gly Lys Phe Lys His Thr
                20                  25                  30

Leu Asp Leu Arg Phe Asp Val Thr Gln Lys Thr Gln Arg Arg Trp Phe
            35                  40                  45

Leu Asp Lys Leu Val Asp Glu Ile Gly Val Gly Tyr Val Tyr Asp Ser
        50                  55                  60

Gly Ser Val Ser Gln Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
            130                 135                 140

Val Leu Asp
145

<210> SEQ ID NO 81
<211> LENGTH: 147
<212> TYPE: PRT
<213> ORGANISM: Artificial Sequence
<220> FEATURE:
<223> OTHER INFORMATION: Synthesized

<400> SEQUENCE: 81

Lys Glu Phe Leu Leu Tyr Leu Ala Gly Phe Val Asp Gly Asp Gly Ser
1               5                   10                  15

Ile Phe Ala Ser Ile Arg Pro Arg Gln Gly Gly Lys Phe Lys His Thr
            20                  25                  30

Leu Asp Leu Arg Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Gln Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 82
<211> LENGTH: 147
<212> TYPE: PRT
<213> ORGANISM: Artificial Sequence
<220> FEATURE:
<223> OTHER INFORMATION: Synthesized

<400> SEQUENCE: 82

Lys Glu Phe Leu Leu Tyr Leu Ala Gly Phe Val Asp Gly Asp Gly Ser
1               5                   10                  15

Ile Tyr Ala Ser Ile Gln Pro Arg Gln Gly Arg Lys Phe Lys His Ser
            20                  25                  30

Leu Glu Leu Lys Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Ser Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
                    115                 120                 125

Leu Asn Asp Ser Lys Thr Arg Lys Thr Thr Ser Glu Thr Val Arg Ala
    130                 135                 140

Val Leu Asp
145

<210> SEQ ID NO 83
<211> LENGTH: 147
<212> TYPE: PRT
<213> ORGANISM: Artificial Sequence
<220> FEATURE:
<223> OTHER INFORMATION: Synthesized

<400> SEQUENCE: 83

Lys Glu Phe Leu Leu Tyr Leu Ala Gly Phe Val Asp Gly Asp Gly Ser
1               5                  10                  15

Ile Tyr Ala Ser Ile Gln Pro Arg Gln Gly Arg Lys Phe Lys His Ser
            20                  25                  30

Leu Glu Leu Lys Phe Asp Val Thr Gln Lys Thr Gln Arg Arg Trp Phe
        35                  40                  45

Leu Asp Lys Leu Val Asp Glu Ile Gly Val Gly Tyr Val Tyr Asp Ser
    50                  55                  60

Gly Ser Val Ser Ser Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 84
<211> LENGTH: 147
<212> TYPE: PRT
<213> ORGANISM: Artificial Sequence
<220> FEATURE:
<223> OTHER INFORMATION: Synthesized

<400> SEQUENCE: 84

Lys Glu Phe Leu Leu Tyr Leu Ala Gly Phe Val Asp Gly Asp Gly Ser
1               5                  10                  15

Ile Phe Ala Cys Ile Leu Pro Lys Gln Ser His Lys Phe Lys His Thr
            20                  25                  30

Leu Ser Leu Arg Phe Thr Val Gly Gln Lys Thr Gln Arg Arg Trp Phe
        35                  40                  45

Leu Asp Lys Leu Val Asp Glu Ile Gly Val Gly Tyr Val Tyr Asp Leu
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

```
Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 85
<211> LENGTH: 147
<212> TYPE: PRT
<213> ORGANISM: Artificial Sequence
<220> FEATURE:
<223> OTHER INFORMATION: Synthesized

<400> SEQUENCE: 85

Lys Glu Phe Leu Leu Tyr Leu Ala Gly Phe Val Asp Gly Asp Gly Ser
1               5                   10                  15

Ile Phe Ala Thr Ile Gln Pro Arg Gln Ser Ala Lys Phe Lys His Gly
            20                  25                  30

Leu Ile Leu Trp Phe Thr Val Gly Gln Lys Thr Gln Arg Arg Trp Phe
        35                  40                  45

Leu Asp Lys Leu Val Asp Glu Ile Gly Ala Gly Tyr Val Ile Asp Leu
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 86
<211> LENGTH: 147
<212> TYPE: PRT
<213> ORGANISM: Artificial Sequence
<220> FEATURE:
<223> OTHER INFORMATION: Synthesized

<400> SEQUENCE: 86

Lys Glu Phe Leu Leu Tyr Leu Ala Gly Phe Val Asp Gly Asp Gly Ser
1               5                   10                  15

Ile Phe Ala Thr Ile Arg Pro Arg Gln Arg Pro Lys Phe Lys His Asp
            20                  25                  30

Leu Val Leu Trp Phe Thr Val Gly Gln Lys Thr Gln Arg Arg Trp Phe
        35                  40                  45

Leu Asp Lys Leu Val Asp Glu Ile Gly Ala Gly Tyr Val Leu Asp Leu
    50                  55                  60

Gly Gly Val Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

-continued

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 87
<211> LENGTH: 147
<212> TYPE: PRT
<213> ORGANISM: Artificial Sequence
<220> FEATURE:
<223> OTHER INFORMATION: Synthesized

<400> SEQUENCE: 87

Lys Glu Phe Leu Leu Tyr Leu Ala Gly Phe Val Asp Gly Asp Gly Ser
1               5                   10                  15

Ile Phe Ala Thr Ile Trp Pro Arg Gln Ser Ala Lys Phe Lys His Gln
            20                  25                  30

Leu Val Leu Trp Phe Ala Val Gly Gln Lys Thr Gln Arg Arg Trp Phe
        35                  40                  45

Leu Asp Lys Leu Val Asp Glu Ile Gly Ala Gly Tyr Val Val Asp Ala
    50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 88
<211> LENGTH: 20
<212> TYPE: DNA
<213> ORGANISM: Artificial Sequence
<220> FEATURE:
<223> OTHER INFORMATION: Synthesized

<400> SEQUENCE: 88
cctttcaact ccatctccat                                              20

<210> SEQ ID NO 89
<211> LENGTH: 21
<212> TYPE: DNA
<213> ORGANISM: Artificial Sequence
<220> FEATURE:
<223> OTHER INFORMATION: Synthesized

<400> SEQUENCE: 89
acatacggtt tagtcacaag t                                            21

<210> SEQ ID NO 90
<211> LENGTH: 19
<212> TYPE: DNA
<213> ORGANISM: Artificial Sequence

```
<220> FEATURE:
<223> OTHER INFORMATION: Synthesized

<400> SEQUENCE: 90
tccagtcact taggctcag                                                19

<210> SEQ ID NO 91
<211> LENGTH: 38
<212> TYPE: DNA
<213> ORGANISM: Artificial Sequence
<220> FEATURE:
<223> OTHER INFORMATION: Synthesized

<400> SEQUENCE: 91
cccttacagt tattaactac tctcatgagg ttcattcc                            38

<210> SEQ ID NO 92
<211> LENGTH: 38
<212> TYPE: DNA
<213> ORGANISM: Artificial Sequence
<220> FEATURE:
<223> OTHER INFORMATION: Synthesized

<400> SEQUENCE: 92
ccccggcact tgaaagtagc agatgcaaga agggcaca                            38

<210> SEQ ID NO 93
<211> LENGTH: 34
<212> TYPE: DNA
<213> ORGANISM: Artificial Sequence
<220> FEATURE:
<223> OTHER INFORMATION: Synthesized

<400> SEQUENCE: 93
actataacca gcaccttgaa cttcccctct cata                                34

<210> SEQ ID NO 94
<211> LENGTH: 38
<212> TYPE: DNA
<213> ORGANISM: Artificial Sequence
<220> FEATURE:
<223> OTHER INFORMATION: Synthesized

<400> SEQUENCE: 94
gccctgcctg tccattacac tgatgacatt atgctgac                            38

<210> SEQ ID NO 95
<211> LENGTH: 39
<212> TYPE: DNA
<213> ORGANISM: Artificial Sequence
<220> FEATURE:
<223> OTHER INFORMATION: Synthesized

<400> SEQUENCE: 95
ggccctacaa ccattctgcc tttcactttc agtgcaata                           39

<210> SEQ ID NO 96
<211> LENGTH: 36
<212> TYPE: DNA
<213> ORGANISM: Artificial Sequence
<220> FEATURE:
<223> OTHER INFORMATION: Synthesized

<400> SEQUENCE: 96
cacaaggggg aagagtgtga gggtgtggga taagaa                              36
```

ENGINEERED NUCLEASES USEFUL FOR TREATMENT OF HEMOPHILIA A

CROSS REFERENCE TO RELATED APPLICATIONS

This application is a national stage filing under 35 U.S.C. § 371 of international application number PCT/US2017/030872, filed May 3, 2017, which claims priority to U.S. Provisional Application No. 62/331,335, entitled "ENGINEERED NUCLEASES USEFUL FOR TREATMENT OF HEMOPHILIA A," filed May 3, 2016, the content of each of which is hereby incorporated by reference in its entirety.

FIELD OF THE INVENTION

The invention relates to the field of molecular biology and recombinant nucleic acid technology. In particular, the invention relates to engineered nucleases having specificity for a recognition sequence within intron 22 of a Factor VIII gene, and particularly within the int22h-1 sequence. Such engineered nucleases are useful in methods for treating hemophilia A characterized by an inversion of exons 1-22 in the Factor VIII gene.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 2, 2017, is named 182WO1_Sequence_Listing_Final, and is 172,847 bytes in size.

BACKGROUND OF THE INVENTION

Hemophilia A is a common genetic bleeding disorder with an incidence of 1 in 5000 males worldwide. This genetic disease can result from various mutations within the coagulation Factor VIII (F8) gene located on the X chromosome, which include large deletions, insertions, inversions, and point mutations. Clinically, hemophilia A can be classified based on relative Factor VIII activity in the patient's plasma as mild (5-30% activity; 50% of patients), moderate (2-5% activity; 10% of patients), or severe (<1% activity; 50% of patients). Currently, there is no cure for hemophilia A. Standard therapy includes the administration of recombinant Factor VIII, but this approach is limited by cost, the requirement for frequent injections, and the formation of Factor VIII-inactivating antibodies in the subject which reduce the effectiveness of therapy. Therefore, a clear need still exists for alternative treatments for hemophilia A. Gene therapy, targeting mutations in the Factor VIII gene, remains an attractive yet elusive approach to treatment.

Factor VIII is an essential component of the clotting cascade. The protein circulates in the body in an inactive form that is attached to von Willebrand factor. In response to injury, Factor VIII is activated (Factor VIIIa) and separates from von Willebrand factor, then interacts with Factor IXa as part of the clotting cascade which leads to the formation of firbin and stable clotting. A number of studies have suggested that Factor VIII is produced by liver sinusoidal endothelial cells, as well as extra-hepatic, hematopoietic cells throughout the body.

The Factor VIII gene on the X chromosome is large and structurally complex, comprising ~180 kb and 26 exons. The wild-type Factor VIII gene encodes two proteins. The first protein is the full-length Factor VIII protein, which is encoded by the 9030 bases found in exons 1 to 26, and has a circulating form containing 2332 amino acid residues. The second protein, referred to as Factor VIIIb, is encoded by 2598 bases in 5 exons present in the Factor VIII gene. The resulting protein comprises 216 amino acids and has a presently unknown function.

Approximately 45% of severe hemophilia A cases are caused by an intra-chromosomal inversion that involves intron 22 of the Factor VIII gene. This inversion arises when an ~9.5 kb segment of intron 22, referred to as int22h-1, recombines with one of two repeat copies (referred to as int22h-2 and int22h-3, respectively) which are positioned approximately 400 kb and 500 kb telomeric to the Factor VIII gene on the X chromosome. Following recombination, exons 1-22 of the Factor VIII gene become inverted in the genome relative to exons 23-26, resulting in the expression of a truncated, inactive Factor VIII protein that lacks the amino acids encoded by exons 23-26 (Sauna et al. (2015) Blood 125(2): 223-228).

The upstream repeat copy involved in exon 1-22 inversion is oriented in the opposite direction as int22h-1. Early studies suggested that int22h-2 and int22h-3 were both in reverse orientation relative to int22h-1, allowing for recombination to occur with either repeat sequence. This was referred to as Type I inversion and Type II inversion. However, more recent evidence indicates that int22h-2 and int22h-3 are found in an inverse orientation to one another on the X chromosome, and are part of an imperfect palindrome (FIG. 1). Recombination of sequences within this palindrome allows int22h-2 and in22h-3 to swap places in the genome and, consequently, change their orientation relative to int22h-1. As a result, the int22h-1 sequence can, in different circumstances, recombine with the int22h-2 repeat or the int22h-3 repeat, depending on which is in the opposite orientation to int22h-1 (Bagnall et al. (2006) Journal of Thrombosis and Haemostasis 4: 591-598).

Of note, intron 22 of the Factor VIII gene contains a CpG island that acts as a bi-directional promoter for two further genes, referred to as F8A1 (Factor VIII-associated 1) and F8B. The CpG island and the intron-less F8A1 gene (SEQ ID NO: 5) are both contained within the int22h-1 sequence (and consequently, within int22h-2 and in22h-3) and are transcribed in the opposite direction as the Factor VIII gene (Bowen (2002) J. Clin. Pathol: Mol. Pathol. 55: 127-144). Interestingly, the inventors have determined that the sequence of the F8A1 gene is the only region of the human Factor VIII gene that exhibits significant homology to the Factor VIII gene in the canine genome, and particularly in a clinically-relevant population of canines that are Factor VIII-deficient and exhibit an inversion of exons 1-22 in their Factor VIII gene (Lozier et al. (2002) PNAS 99(20): 12991-12996).

The present invention requires the use of site-specific, rare-cutting endonucleases that are engineered to recognize DNA sequences within the int22h-1 sequence in order to generate a double-strand break and promote recombination between int22h-1 and an inversely-oriented repeat sequence (int22h-2 or int22h-3) positioned telomeric to the Factor VIII gene. The inventors have found that nuclease-induced recombination between these regions results in an inversion or reversion of exons 1-22 of the Factor VIII gene.

Methods for producing engineered, site-specific endonucleases are known in the art. For example, zinc-finger nucleases (ZFNs) can be engineered to recognize and cut pre-determined sites in a genome. ZFNs are chimeric proteins comprising a zinc finger DNA-binding domain fused to the nuclease domain of the FokI restriction enzyme. The zinc finger domain can be redesigned through rational or experimental means to produce a protein which binds to a pre-determined DNA sequence ~18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in S. Durai et al., *Nucleic Acids Res* 33, 5978 (2005)).

Likewise, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak, et al. (2013) *Curr Opin Struct Biol.* 23:93-9). In this case, however, the DNA binding domain comprises a tandem array of TAL-effector domains, each of which specifically recognizes a single DNA basepair.

Compact TALENs are an alternative endonuclease architecture that avoids the need for dimerization (Beurdeley, et al. (2013) *Nat Commun.* 4:1762). A Compact TALEN comprises an engineered, site-specific TAL-effector DNA-binding domain fused to the nuclease domain from the I-TevI homing endonuclease. Unlike FokI, I-TevI does not need to dimerize to produce a double-strand DNA break so a Compact TALEN is functional as a monomer.

Engineered endonucleases based on the CRISPR/Cas9 system are also known in the art (Ran, et al. (2013) *Nat Protoc.* 8:2281-2308; Mali et al. (2013) *Nat Methods.* 10:957-63). A CRISPR endonuclease comprises two components: (1) a caspase effector nuclease, typically microbial Cas9; and (2) a short "guide RNA" comprising a ~20 nucleotide targeting sequence that directs the nuclease to a location of interest in the genome. By expressing multiple guide RNAs in the same cell, each having a different targeting sequence, it is possible to target DNA breaks simultaneously to multiple sites in the genome.

In the preferred embodiment of the invention, the DNA break-inducing agent is an engineered homing endonuclease (also called a "meganuclease"). Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), *Nucleic Acids Res.* 29(18): 3757-3774). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. This, coupled with the extremely low frequency of off-target cutting observed with engineered meganucleases makes them the preferred endonuclease for the present invention.

The use of engineered nucleases for gene therapy in severe hemophilia A has been limited. Park et al. described the use of a TALEN to induce an inversion of exon 1 in the Factor VIII gene in HEK 293T cells and induced pluripotent stem cells (iPSCs) (Park et al. (2014), *PNAS* 111(25): 9253-9258). Inversions of exon 1 are also associated with the occurrence of hemophilia A occur due to homologous recombination between an int1h-1 sequence in intron 1 of the Factor VIII gene and a single homologous region (int1h-2) positioned telomeric to the Factor VIII gene. The TALEN selected for this study cut within the intron 1 homology region in order to induce an inversion of this shorter sequence with an efficiency of 1.9% and 1.4% in the HEK 293T cells and iPSCs, respectively. The authors further demonstrated reversion of exon 1 in the iPSCs at a similar efficiency of 1.3%.

In a subsequent study, Park et al. reported the use of a CRISPR/Cas system to induce a reversion of exons 1-22 of the Factor VIII gene in iPSCs obtained from patients suffering from severe hemophilia A (Park et al. (2015) *Cell Stem Cell* 17: 213-220). The authors noted that inversions of exons 1-22 are eight times more prevalent than inversions of exon 1, but emphasized that the exon 1-22 inversion is technically more challenging to revert due in part to the substantially larger size of the inversion (600 kbp compared to 140 kbp) and the presence of three homologs of the int22h-1 sequence on the X chromosome, compared to only two homologs of the int1h-1 sequence. Indeed, Park et al. specifically targets recognition sequences outside of the int22h-1, int22h-2, and int22h-3 homology regions in order to rule out the possibility that unwanted deletions or inversions involving any two of the three int22 homologs, rather than the desired reversion of the inverted 600-kbp segment, would be induced by cutting within an int22h homology region. Using this approach, the authors observed a reversion frequency of approximately 3.7% in iPS cells.

The present invention improves on the art in several aspects. Despite suggestions in the art to avoid targeting recognition sequences within the int22h homology regions, the inventors surprisingly found that targeting recognition sequences within int22h-1 can, in fact, produce an inversion or reversion of exons 1-22 in the Factor VIII with high efficiency. Further, several recognition sequences targeted within the int22h-1 sequence are found within the F8A1 sequence, which the inventors found to be the only region of the Factor VIII gene which shares a high degree of homology with the canine Factor VIII gene. Thus, the methods of the invention are useful not only in human subjects suffering from hemophilia A, but also in the clinically-relevant canine hemophilia A population which also expresses an inversion of exons 1-22. Accordingly, the present invention fulfills a need in the art for further gene therapy approaches to severe hemophilia A.

SUMMARY OF THE INVENTION

The present invention provides engineered nucleases useful for the treatment of hemophilia A, which is characterized by an inversion of exons 1-22 of the Factor VIII gene. The engineered nucleases of the invention recognize and a cleave recognition sequence within an int22h-1 sequence of the Factor VIII gene, thereby promoting recombination between the int22h-1 sequence and an identical, or highly homologous, inverted repeat sequence positioned telomeric to the Factor VIII gene on the X chromosome. Such recombination results in a reversion of exons 1-22 to generate a wild-type Factor VIII gene. The present invention also provides pharmaceutical compositions and methods for treatment of hemophilia A which utilize an engineered nuclease having specificity for a recognition sequence positioned within the int22h-1 sequence of the Factor VIII gene. The present invention further provides genetically-modified cells which have been modified to correct an inversion of exons 1-22 in the Factor VIII gene, as well as pharmaceutical compositions comprising such genetically-modified cells and methods of using the same for the treatment of hemophilia A.

Thus, in one aspect, the invention provides an engineered meganuclease that recognizes and cleaves a recognition sequence within an int22h-1 sequence of a Factor VIII gene. The engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In one embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the recognition sequence can be within an F8A1 coding sequence of the Factor VIII gene. In such an embodiment, the F8A1 coding sequence can have at least 80%, at least 85%, at least 90%, at least 95%, or more, sequence identity to SEQ ID NO: 5 or SEQ ID NO: 6. In another such embodiment, the F8A1 coding sequence can comprise SEQ ID NO: 5 or SEQ ID NO: 6.

In another embodiment, the recognition sequence can comprise SEQ ID NO: 7.

In some such embodiments, the HVR1 region can comprise an amino acid sequence having at least 80% sequence identity to an amino acid sequence corresponding to residues 215-270 of SEQ ID NO: 19 or residues 24-79 of any one of SEQ ID NOs: 20-21.

In certain embodiments, the HVR1 region can comprise residues corresponding to residues 215, 217, 219, 221, 223, 224, 229, 231, 233, 235, 237, 259, 261, 266, and 268 of SEQ ID NO: 19 or residues 24, 26, 28, 30, 32, 33, 38, 40, 42, 44, 46, 68, 70, 75, and 77 of any one of SEQ ID NOs: 20-21.

In particular embodiments, the HVR1 region can comprise residues 215-270 of SEQ ID NO: 19 or residues 24-79 of any one of SEQ ID NOs: 20-21.

In some such embodiments, the HVR2 region can comprise an amino acid sequence having at least 80% sequence identity to an amino acid sequence corresponding to residues 24-79 of SEQ ID NO: 19 or residues 215-270 of any one of SEQ ID NOs: 20-21.

In certain embodiments, the HVR2 region can comprise residues corresponding to residues 24, 26, 28, 30, 32, 33, 38, 40, 42, 44, 68, 70, 75, and 77 of SEQ ID NO: 19 or residues 215, 217, 219, 221, 223, 224, 229, 231, 233, 235, 259, 261, 266, and 268 of any one of SEQ ID NOs: 20-21.

In particular embodiments, the HVR2 region can comprise residues 24-79 of SEQ ID NO: 19 or residues 215-270 of any one of SEQ ID NOs: 20-21.

In one such embodiment, the first subunit can comprise an amino acid sequence having at least 80%, at least 85%, at least 90%, at least 95%, or more, sequence identity to residues 198-344 of SEQ ID NO: 19 or residues 7-153 of SEQ ID NO: 20 or 21, and the second subunit can comprise an amino acid sequence having at least 80%, at least 85%, at least 90%, at least 95, or more, sequence identity to residues 7-153 of SEQ ID NO: 19 or residues 198-344 of SEQ ID NO: 20 or 21.

In another such embodiment, the first subunit can comprise residues 198-344 of SEQ ID NO: 19 or residues 7-153 of SEQ ID NO: 20 or 21. In another such embodiment, the second subunit can comprise residues 7-153 of SEQ ID NO: 19 or residues 198-344 of SEQ ID NO: 20 or 21.

In another such embodiment, the engineered meganuclease can be a single-chain meganuclease comprising a linker, wherein the linker covalently joins the first subunit and the second subunit.

In another such embodiment, the engineered meganuclease can comprise the amino acid sequence of any one of SEQ ID NOs: 19-21.

In another embodiment, the recognition sequence can comprise SEQ ID NO: 9.

In some such embodiments, the HVR1 region can comprise an amino acid sequence having at least 80% sequence identity to an amino acid sequence corresponding to residues 215-270 of any one of SEQ ID NOs: 28-31.

In certain embodiments, the HVR1 region can comprise residues corresponding to residues 215, 217, 219, 221, 223, 224, 231, 233, 235, 237, 261, 266, and 268 of any one of SEQ ID NOs: 28-31.

In particular embodiments, the HVR1 region can comprise residues 215-270 of any one of SEQ ID NOs: 28-31.

In some such embodiments, the HVR2 region can comprise an amino acid sequence having at least 80% sequence identity to an amino acid sequence corresponding to residues 24-79 of any one of SEQ ID NOs: 28-31.

In certain embodiments, the HVR2 region can comprise residues corresponding to residues 24, 26, 28, 30, 32, 33, 38, 40, 42, 44, 46, 68, 70, 75, and 77 of any one of SEQ ID NOs: 28-31.

In further embodiments, the HVR2 region further can comprise a residue corresponding to residue 73 of SEQ ID NO: 30.

In particular embodiments, the HVR2 region can comprise residues 24-79 of any one of SEQ ID NOs: 28-31.

In one such embodiment, the first subunit can comprise an amino acid sequence having at least 80%, at least 85%, at least 90%, at least 95%, or more, sequence identity to residues 198-344 of any one of SEQ ID NOs: 28-31, and the second subunit can comprise an amino acid sequence having at least 80%, at least 85%, at least 90%, at least 95%, or more, sequence identity to residues 7-153 of any one of SEQ ID NOs: 28-31.

In another such embodiment, the first subunit can comprise residues 198-344 of any one of SEQ ID NOs: 28-31. In another such embodiment, the second subunit can comprise residues 7-153 of any one of SEQ ID NOs: 28-31.

In another such embodiment, the engineered meganuclease is a single-chain meganuclease comprising a linker, wherein the linker covalently joins the first subunit and the second subunit.

In another such embodiment, the engineered meganuclease can comprise the amino acid sequence of any one of SEQ ID NOs: 28-31.

In another embodiment, the recognition sequence can comprise SEQ ID NO: 11.

In some such embodiments, the HVR1 region can comprise an amino acid sequence having at least 80% sequence identity to an amino acid sequence corresponding to residues 24-79 of SEQ ID NO: 40 or residues 215-270 of any one of SEQ ID NOs: 41-43.

In certain embodiments, the HVR1 region can comprise residues corresponding to residues 24, 26, 28, 30, 32, 33, 38, 40, 42, 44, 46, 68, 70, 75, and 77 of SEQ ID NO: 40 or residues 215, 217, 219, 221, 223, 224, 229, 231, 233, 235, 237, 259, 261, 266, and 268 of any one of SEQ ID NOs: 41-43.

In particular embodiments, the HVR1 region can comprise residues 24-79 of SEQ ID NO: 40 or residues 215-270 of any one of SEQ ID NOs: 41-43.

In some such embodiments, the HVR2 region can comprise an amino acid sequence having at least 80% sequence identity to an amino acid sequence corresponding to residues 215-270 of SEQ ID NO: 40 or residues 24-79 of any one of SEQ ID NOs: 41-43.

In certain embodiments, the HVR2 region can comprise residues corresponding to residues 215, 217, 219, 221, 223, 224, 229, 231, 233, 235, 237, 259, 261, 266, and 268 of SEQ ID NO: 40 or residues 24, 26, 28, 30, 32, 33, 38, 40, 42, 44, 46, 68, 70, 75, and 77 of any one of SEQ ID NOs: 41-43.

In particular embodiments, the HVR2 region can comprise residues 215-270 of SEQ ID NO: 40 or residues 24-79 of any one of SEQ ID NOs: 41-43.

In one such embodiment, the first subunit can comprise an amino acid sequence having at least 80%, at least 85%, at least 90%, at least 95%, or more, sequence identity to residues 7-153 of SEQ ID NO: 40 or residues 198-344 of any one of SEQ ID NOs: 41-43, and the second subunit can comprise an amino acid sequence having at least 80%, at least 85%, at least 90%, at least 95%, or more, sequence identity to residues 198-344 of SEQ ID NO: 40 or residues 7-153 of any one of SEQ ID NO:s 41-43.

In another such embodiment, the first subunit can comprise residues 7-153 of SEQ ID NO: 40 or residues 198-344 of any one of SEQ ID NOs: 41-43. In another such embodiment, the second subunit can comprise residues 198-344 of SEQ ID NO: 40 or residues 7-153 of any one of SEQ ID NOs: 41-43.

In another such embodiment, the engineered meganuclease is a single-chain meganuclease comprising a linker, wherein the linker covalently joins the first subunit and the second subunit.

In another such embodiment, the engineered meganuclease can comprise the amino acid sequence of any one of SEQ ID NOs: 40-43.

In another embodiment, the recognition sequence can comprise SEQ ID NO: 13.

In some such embodiments, the HVR1 region can comprise an amino acid sequence having at least 80% sequence identity to an amino acid sequence corresponding to residues 24-79 of any one of SEQ ID NOs: 52-55.

In certain embodiments, the HVR1 region can comprise residues corresponding to residues 24, 26, 28, 30, 32, 33, 38, 40, 42, 44, 68, 70, 75, and 77 of any one of SEQ ID NOs: 52-55.

In particular embodiments, the HVR1 region can comprise residues 24-79 of any one of SEQ ID NOs: 52-55.

In some such embodiments, the HVR2 region can comprise an amino acid sequence having at least 80% sequence identity to an amino acid sequence corresponding to residues 215-270 of any one of SEQ ID NOs: 52-55.

In certain embodiments, the HVR2 region can comprise residues corresponding to residues 215, 217, 219, 221, 223, 224, 229, 231, 233, 235, 237, 259, 261, 266, and 268 of any one of SEQ ID NOs: 52-55.

In particular embodiments, the HVR2 region can comprise residues 215-270 of any one of SEQ ID NOs: 52-55.

In one such embodiment, the first subunit can comprise an amino acid sequence having at least 80%, at least 85%, at least 90%, at least 95%, or more, sequence identity to residues 7-153 of any one of SEQ ID NOs: 52-55, and the second subunit can comprise an amino acid sequence having at least 80%, at least 85%, at least 90%, at least 95%, or more, sequence identity to residues 198-344 of any one of SEQ ID NOs: 52-55.

In another such embodiment, the first subunit can comprise residues 7-153 of any one of SEQ ID NOs: 52-55. In another such embodiment, the second subunit can comprise residues 198-344 of any one of SEQ ID NOs: 52-55.

In another such embodiment, the engineered meganuclease is a single-chain meganuclease comprising a linker, wherein the linker covalently joins the first subunit and the second subunit.

In another such embodiment, the engineered meganuclease can comprise the amino acid sequence of any one of SEQ ID NOs: 52-55.

In another embodiment, the recognition sequence can comprise SEQ ID NO: 15.

In some such embodiments, the HVR1 region can comprise an amino acid sequence having at least 80% sequence identity to an amino acid sequence corresponding to residues 24-79 of SEQ ID NO: 64 or residues 215-270 of any one of SEQ ID NOs: 65-67.

In certain embodiments, the HVR1 region can comprise residues corresponding to residues 24, 26, 28, 30, 32, 33, 40, 42, 44, 46, 68, 70, 75, and 77 of SEQ ID NO: 64 or residues 215, 217, 219, 221, 223, 224, 231, 233, 235, 237, 259, 261, 266, and 268 of any one of SEQ ID NOs: 65-67.

In particular embodiments, the HVR1 region can comprise residues 24-79 of SEQ ID NO: 64 or residues 215-270 of any one of SEQ ID NOs: 65-67.

In some such embodiments, the HVR2 region can comprise an amino acid sequence having at least 80% sequence identity to an amino acid sequence corresponding to residues 215-270 of SEQ ID NO: 64 or residues 24-79 of any one of SEQ ID NOs: 65-67.

In certain embodiments, the HVR2 region can comprise residues corresponding to residues 215, 217, 219, 221, 223, 224, 229, 231, 233, 235, 237, 259, 261, 266, and 268 of SEQ ID NO: 64 or residues 24, 26, 28, 30, 32, 33, 38, 40, 42, 44, 46, 68, 70, 75, and 77 of any one of SEQ ID NOs: 65-67.

In particular embodiments, the HVR2 region can comprise residues 215-270 of SEQ ID NO: 64 or residues 24-79 of any one of SEQ ID NOs: 65-67.

In one such embodiment, the first subunit can comprise an amino acid sequence having at least 80%, at least 85%, at least 90%, at least 95%, or more, sequence identity to residues 7-153 of SEQ ID NO: 64 or residues 198-344 of any one of SEQ ID NOs: 65-67, and the second subunit can comprise an amino acid sequence having at least 80%, at least 85%, at least 90%, at least 95%, or more, sequence identity to residues 198-344 of SEQ ID NO: 64 or residues 7-153 of any one of SEQ ID NO:s 65-67.

In another such embodiment, the first subunit can comprise residues 7-153 of SEQ ID NO: 64 or residues 198-344 of any one of SEQ ID NOs: 65-67. In another such embodiment, the second subunit can comprise residues 198-344 of SEQ ID NO: 64 or residues 7-153 of any one of SEQ ID NOs: 65-67.

In another such embodiment, the engineered meganuclease is a single-chain meganuclease comprising a linker, wherein the linker covalently joins the first subunit and the second subunit.

In another such embodiment, the engineered meganuclease can comprise the amino acid sequence of any one of SEQ ID NOs: 64-67.

In another embodiment, the recognition sequence can comprise SEQ ID NO: 17.

In some such embodiments, the HVR1 region can comprise an amino acid sequence having at least 80% sequence identity to an amino acid sequence corresponding to residues 215-270 of any one of SEQ ID NOs: 76-79.

In certain embodiments, the HVR1 region can comprise residues corresponding to residues 215, 217, 219, 221, 223, 224, 229, 231, 233, 235, 259, 261, 266, and 268 of any one of SEQ ID NOs: 76-79.

In particular embodiments, the HVR1 region can comprise residues 215-270 of any one of SEQ ID NOs: 76-79.

In some such embodiments, the HVR2 region can comprise an amino acid sequence having at least 80% sequence identity to an amino acid sequence corresponding to residues 24-79 of any one of SEQ ID NOs: 76-79.

In certain embodiments, the HVR2 region can comprise residues corresponding to residues 24, 26, 28, 30, 32, 33, 38, 40, 42, 44, 46, 68, 70, 75, and 77 of any one of SEQ ID NOs: 76-79.

In particular embodiments, the HVR2 region can comprise residues 24-79 of any one of SEQ ID NOs: 76-79.

In one such embodiment, the first subunit can comprise an amino acid sequence having at least 80%, at least 85%, at least 90%, at least 95%, or more, sequence identity to residues 198-344 of any one of SEQ ID NOs: 76-79, and the second subunit can comprise an amino acid sequence having at least 80%, at least 85%, at least 90%, at least 95%, or more, sequence identity to residues 7-153 of any one of SEQ ID NOs: 76-79.

In another such embodiment, the first subunit can comprise residues 198-344 of any one of SEQ ID NOs: 76-79. In another such embodiment, the second subunit can comprise residues 7-153 of any one of SEQ ID NOs: 76-79.

In another such embodiment, the engineered meganuclease is a single-chain meganuclease comprising a linker, wherein the linker covalently joins the first subunit and the second subunit.

In another such embodiment, the engineered meganuclease can comprise the amino acid sequence of any one of SEQ ID NOs: 76-79.

In another aspect, the invention provides an isolated polynucleotide comprising a nucleic acid sequence encoding any engineered meganuclease of the invention. In a particular embodiment, the isolated polynucleotide can be an mRNA.

In another aspect, the invention provides a recombinant DNA construct comprising a nucleic acid sequence which encodes any engineered meganuclease of the invention.

In one embodiment, the recombinant DNA construct can be self-cleaving.

In another embodiment, the recombinant DNA construct encodes a viral vector. In such an embodiment, the viral vector can be a retrovirus, a lentivirus, an adenovirus, or an adeno-associated virus (AAV) vector. In a particular embodiment, the viral vector can be a recombinant AAV vector.

In another aspect, the invention provides a viral vector comprising a nucleic acid sequence which encodes any engineered meganuclease of the invention.

In one embodiment, the viral vector can be a retrovirus, a lentivirus, an adenovirus, or an adeno-associated virus (AAV) vector. In a particular embodiment, the viral vector can be a recombinant AAV vector.

In another aspect, the invention provides a pharmaceutical composition for treatment of a subject having hemophilia A. In such an aspect, hemophilia A is characterized by an inversion of exons 1-22 in a Factor VIII gene. The pharmaceutical composition comprises a pharmaceutically acceptable carrier and: (a) a nucleic acid encoding an engineered nuclease, wherein the engineered nuclease is expressed in a target cell in vivo; or (b) an engineered nuclease protein; wherein the engineered nuclease has specificity for a first recognition sequence positioned within an int22h-1 sequence of the Factor VIII gene in the target cell.

In one embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the first recognition sequence can be within an F8A1 coding sequence. In such an embodiment, the F8A1 coding sequence can have at least 80%, at least 85%, at least 90%, at least 95%, or more sequence identity to SEQ ID NO: 5 or SEQ ID NO: 6. In another such embodiment, the F8A1 coding sequence can comprise SEQ ID NO: 5 or SEQ ID NO: 6.

In another embodiment, the engineered nuclease can have specificity for a second recognition sequence that is identical to, or has a high degree of homology with, the first recognition sequence, wherein the second recognition sequence is positioned in a repeat sequence telomeric to the Factor VIII gene in the X chromosome. In such an embodiment, the repeat sequence is identical to, or has a high degree of homology with, the int22h-1 sequence except that the repeat sequence is in reverse orientation relative to the int22h-1 sequence.

In another embodiment, the nucleic acid encoding the engineered nuclease can be an mRNA.

In another embodiment, the pharmaceutical composition comprises a recombinant DNA construct comprising the nucleic acid. In one such embodiment, the recombinant DNA construct can be self-cleaving.

In another embodiment, the pharmaceutical composition comprises a viral vector comprising the nucleic acid. In one such embodiment, the viral vector can be a retrovirus, a lentivirus, an adenovirus, or an AAV. In a particular embodiment, the viral vector can be a recombinant AAV vector.

In another embodiment, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment, wherein the engineered nuclease is an engineered meganuclease, the first recognition sequence can comprise SEQ ID NO: 7. In one such embodiment, the pharmaceutical composition can comprise an engineered meganuclease of the invention (or a nucleic acid encoding the same) which recognizes and cleaves SEQ ID NO: 7. In a particular embodiment, the engineered meganuclease can comprise the amino acid sequence of any one of SEQ ID NOs: 19-21.

In another embodiment, wherein the engineered nuclease is an engineered meganuclease, the first recognition sequence can comprise SEQ ID NO: 9. In one such embodiment, the pharmaceutical composition can comprise an engineered meganuclease of the invention (or a nucleic acid encoding the same) which recognizes and cleaves SEQ ID NO: 9. In a particular embodiment, the engineered meganuclease can comprise the amino acid sequence of any one of SEQ ID NOs: 28-31.

In another embodiment, wherein the engineered nuclease is an engineered meganuclease, the first recognition sequence can comprise SEQ ID NO: 11. In one such embodiment, the pharmaceutical composition can comprise an engineered meganuclease of the invention (or a nucleic acid encoding the same) which recognizes and cleaves SEQ ID NO: 11. In a particular embodiment, the engineered meganuclease can comprise the amino acid sequence of any one of SEQ ID NOs: 40-43.

In another embodiment, wherein the engineered nuclease is an engineered meganuclease, the first recognition sequence can comprise SEQ ID NO: 13. In one such embodiment, the pharmaceutical composition can comprise an engineered meganuclease of the invention (or a nucleic acid encoding the same) which recognizes and cleaves SEQ ID NO: 13. In a particular embodiment, the engineered meganuclease can comprise the amino acid sequence of any one of SEQ ID NOs: 52-55.

In another embodiment, wherein the engineered nuclease is an engineered meganuclease, the first recognition sequence can comprise SEQ ID NO: 15. In one such embodiment, the pharmaceutical composition can comprise an engineered meganuclease of the invention (or a nucleic acid encoding the same) which recognizes and cleaves SEQ ID NO: 15. In a particular embodiment, the engineered meganuclease can comprise the amino acid sequence of any one of SEQ ID NOs: 64-67.

In another embodiment, wherein the engineered nuclease is an engineered meganuclease, the first recognition sequence can comprise SEQ ID NO: 17. In one such embodiment, the pharmaceutical composition can comprise an engineered meganuclease of the invention (or a nucleic acid encoding the same) which recognizes and cleaves SEQ ID NO: 17. In a particular embodiment, the engineered meganuclease can comprise the amino acid sequence of any one of SEQ ID NOs: 76-79.

In another aspect, the invention provides a method for treating a subject having hemophilia A. In such an aspect, hemophilia A is characterized by an inversion of exons 1-22 of a Factor VIII gene. The method comprises delivering to a target cell in the subject: (a) a nucleic acid encoding an engineered nuclease, wherein the engineered nuclease is expressed in the target cell in vivo; or (b) an engineered nuclease protein; wherein the engineered nuclease is any engineered nuclease of the invention which has specificity for a first recognition sequence positioned within an int22h-1 sequence of the Factor VIII gene in the target cell.

In one embodiment of the method, the method comprises administering to the subject a pharmaceutical composition of the invention described above, which comprises (a) a nucleic acid encoding an engineered nuclease of the invention, wherein the engineered nuclease is expressed in a target cell in vivo; or (b) an engineered nuclease protein of the invention.

In another embodiment of the method, the engineered nuclease, or the nucleic acid encoding the engineered nuclease, can be delivered to a target cell which is capable of expressing wild-type Factor VIII, or a progenitor cell which differentiates into a cell which is capable of expressing wild-type Factor VIII. In one such embodiment, the target cell can be a hepatic cell. In a particular embodiment, the hepatic cell can be a hepatic sinusoidal endothelial cell. In another such embodiment, the hepatic cell can be a progenitor cell, such as a hepatic stem cell, which differentiates into a hepatic sinusoidal endothelial cell. In another such embodiment, the target cell can be a hematopoietic endothelial cell. In another such embodiment, the target cell can be a progenitor cell which differentiates into a hematopoietic endothelial cell. It is understood that target cells comprise a Factor VIII gene which has an inversion of exons 1-22.

In another embodiment of the method, the engineered nuclease recognizes and cleaves the first recognition sequence to promote recombination between the int22h-1 sequence and the repeat sequence, resulting in reversion of exons 1-22 to generate a wild-type Factor VIII gene.

In another embodiment of the method, the engineered nuclease further recognizes and cleaves the second recognition sequence in the repeat sequence.

In another embodiment of the method, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment of the method, wherein the engineered nuclease is an engineered meganuclease, the first recognition sequence can comprise SEQ ID NO: 7. In one such embodiment, the engineered meganuclease can be any engineered meganuclease of the invention which recognizes and cleaves SEQ ID NO: 7. In a particular embodiment, the engineered meganuclease can comprise the amino acid sequence of any one of SEQ ID NOs: 19-21.

In another embodiment of the method, wherein the engineered nuclease is an engineered meganuclease, the first recognition sequence can comprise SEQ ID NO: 9. In one such embodiment, the engineered meganuclease can be any engineered meganuclease of the invention which recognizes and cleaves SEQ ID NO: 9. In a particular embodiment, the engineered meganuclease can comprise the amino acid sequence of any one of SEQ ID NOs: 28-31.

In another embodiment of the method, wherein the engineered nuclease is an engineered meganuclease, the first recognition sequence can comprise SEQ ID NO: 11. In one such embodiment, the engineered meganuclease can be any engineered meganuclease of the invention which recognizes and cleaves SEQ ID NO: 11. In a particular embodiment, the engineered meganuclease can comprise the amino acid sequence of any one of SEQ ID NOs: 40-43.

In another embodiment of the method, wherein the engineered nuclease is an engineered meganuclease, the first recognition sequence can comprise SEQ ID NO: 13. In one such embodiment, the engineered meganuclease can be any engineered meganuclease of the invention which recognizes and cleaves SEQ ID NO: 13. In a particular embodiment, the engineered meganuclease can comprise the amino acid sequence of any one of SEQ ID NOs: 52-55.

In another embodiment of the method, wherein the engineered nuclease is an engineered meganuclease, the first recognition sequence can comprise SEQ ID NO: 15. In one such embodiment, the engineered meganuclease can be any engineered meganuclease of the invention which recognizes and cleaves SEQ ID NO: 15. In a particular embodiment, the engineered meganuclease can comprise the amino acid sequence of any one of SEQ ID NOs: 64-67.

In another embodiment of the method, wherein the engineered nuclease is an engineered meganuclease, the first recognition sequence can comprise SEQ ID NO: 17. In one such embodiment, the engineered meganuclease can be any engineered meganuclease of the invention which recognizes and cleaves SEQ ID NO: 17. In a particular embodiment, the engineered meganuclease can comprise the amino acid sequence of any one of SEQ ID NOs: 76-79.

In another embodiment of the method, the subject can be a mammal. In one such embodiment, the subject can be a human. In another such embodiment, the subject can be a canine.

In another aspect, the invention provides a method for producing a genetically-modified cell comprising a wild-type Factor VIII gene. The method comprises: (a) obtaining a cell comprising a Factor VIII gene having an inversion of exons 1-22; and (b) introducing into the cell: (i) a nucleic acid sequence encoding an engineered nuclease, wherein the engineered nuclease is expressed in the cell; or (ii) an engineered nuclease protein; wherein the engineered nuclease has specificity for a first recognition sequence within an int22h-1 sequence of the Factor VIII gene; and wherein the engineered nuclease recognizes and cleaves the first recognition sequence within the int22h-1 sequence to promote recombination between the int22h-1 sequence and a repeat sequence positioned telomeric to the Factor VIII gene; and wherein the repeat sequence is identical to, or has a high degree of homology with, the int22h-1 sequence except that the repeat sequence is in reverse orientation relative to the int22h-1 sequence; and wherein recombination causes reversion of exons 1-22 and generation of the genetically-modified cell comprising a wild-type Factor VIII gene.

In one embodiment, the cell can be a eukaryotic cell. In one such embodiment, the eukaryotic cell can be a pluripotent cell. In such an embodiment, the pluripotent cell can be an induced pluripotent stem (iPS) cell. In a particular embodiment, the iPS cell can be a human iPS cell or a canine iPS cell.

In another embodiment, the int22h-1 sequence can have at least 80%, at least 85%, at least 90%, at least 95%, or more, sequence identity to SEQ ID NO: 3 or SEQ ID NO: 4. In one such embodiment, the int22h-1 sequence can comprise SEQ ID NO: 3 or SEQ ID NO: 4.

In another embodiment, the first recognition sequence can be within an F8A1 coding sequence of the Factor VIII gene. In such an embodiment, the F8A1 coding sequence can have at least 80%, at least 85%, at least 90%, at least 95%, or more, sequence identity to SEQ ID NO: 3 or SEQ ID NO: 4. In a particular embodiment, the F8A1 coding sequence can comprise SEQ ID NO: 3 or SEQ ID NO: 4.

In another embodiment, the engineered nuclease can have specificity for a second recognition sequence that is identical to, or has a high degree of homology with, the first recognition sequence, wherein the second recognition sequence is positioned in a repeat sequence telomeric to the Factor VIII gene in the X chromosome. In such an embodiment, the repeat sequence is identical to, or has a high degree of homology with, the int22h-1 sequence except that the repeat sequence is in reverse orientation relative to the int22h-1 sequence.

In another embodiment, the nucleic acid can be an mRNA.

In another embodiment, the nucleic acid can be introduced into the cell using a recombinant DNA construct. In one such embodiment, the recombinant DNA construct can be self-cleaving.

In another embodiment, the nucleic acid can be introduced into the cell using a viral vector. In one such embodiment, the viral vector can be a retrovirus, a lentivirus, an adenovirus, or an AAV. In a particular embodiment, the viral vector can be a recombinant AAV vector.

In another embodiment, the engineered nuclease can be an engineered meganuclease, a TALEN, a zinc finger nuclease, a compact TALEN, a CRISPR, or a megaTAL. In a particular embodiment, the engineered nuclease can be an engineered meganuclease.

In another embodiment, the engineered nuclease can be any engineered meganuclease of the invention which recognizes and cleaves a recognition sequence comprising SEQ ID NO: 7. In one such embodiment, the engineered meganuclease can comprise the amino acid sequence of any one of SEQ ID NOs: 19-21.

In another embodiment, the engineered nuclease can be any engineered meganuclease of the invention which recognizes and cleaves a recognition sequence comprising SEQ ID NO: 9. In one such embodiment, the engineered meganuclease can comprise the amino acid sequence of any one of SEQ ID NOs: 28-31.

In another embodiment, the engineered nuclease can be any engineered meganuclease of the invention which recognizes and cleaves a recognition sequence comprising SEQ ID NO: 11. In one such embodiment, the engineered meganuclease can comprise the amino acid sequence of any one of SEQ ID NOs: 40-43.

In another embodiment, the engineered nuclease can be any engineered meganuclease of the invention which recognizes and cleaves a recognition sequence comprising SEQ ID NO: 13. In one such embodiment, the engineered meganuclease can comprise the amino acid sequence of any one of SEQ ID NOs: 52-55.

In another embodiment, the engineered nuclease can be any engineered meganuclease of the invention which recognizes and cleaves a recognition sequence comprising SEQ ID NO: 15. In one such embodiment, the engineered meganuclease can comprise the amino acid sequence of any one of SEQ ID NOs: 64-67.

In another embodiment, the engineered nuclease can be any engineered meganuclease of the invention which recognizes and cleaves a recognition sequence comprising SEQ ID NO: 17. In one such embodiment, the engineered meganuclease can comprise the amino acid sequence of any one of SEQ ID NOs: 76-79.

In another aspect, the invention provides a genetically-modified cell, wherein the genetically-modified cell comprises a wild-type Factor VIII gene and is produced according to the methods of the invention described herein, which produce a genetically-modified cell from a cell which comprises a Factor VIII gene having an inversion of exons 1-22.

In another aspect, the invention provides a pharmaceutical composition for treatment of a subject having hemophilia A. In such an aspect, hemophilia A is characterized by an inversion of exons 1-22 in a Factor VIII gene. In different embodiments, the pharmaceutical composition comprises a pharmaceutically acceptable carrier and any genetically-modified cell of the invention, and/or any genetically-modified cell produced according to the methods of the invention, which comprises a wild-type Factor VIII gene.

In another aspect, the invention provides a method for treating a subject having hemophilia A. In such an aspect, hemophilia A is characterized by an inversion of exons 1-22 of the Factor VIII gene. The method comprises administering to the subject a pharmaceutical composition of the invention which comprises a pharmaceutically acceptable carrier and any genetically-modified cell of the invention. Such a genetically-modified cell comprises a wild-type Factor VIII gene following modification.

In one embodiment of the method, the genetically-modified cell can be delivered to a target tissue. In one such embodiment, the target tissue can be the liver. In another such embodiment, the target tissue can be the circulatory system.

In another embodiment of the method, the genetically-modified cell can be a genetically-modified iPS cell. In one such embodiment, the genetically-modified iPS cell can differentiate into a cell which expresses Factor VIII when it is delivered to the target tissue. In a particular embodiment, the genetically-modified iPS cell can differentiate into a hepatic sinusoidal endothelial cell which expresses Factor VIII. In another particular embodiment, the genetically-modified iPS cell can differentiate into a hematopoietic cell, such as a hematopoietic endothelial cell, which expresses Factor VIII.

In another embodiment of the method, the subject can be a mammal. In one such embodiment, the subject can be a human. In another such embodiment, the subject can be a canine.

In another aspect, the invention provides an engineered nuclease, and particularly an engineered meganuclease, described herein for use as a medicament. The invention further provides the use of an engineered nuclease, and particularly an engineered meganuclease, described herein in the manufacture of a medicament for treating hemophilia A, which is characterized by an inversion of exons 1-22 in the Factor VIII gene.

In another aspect, the invention provides an isolated polynucleotide for use as a medicament, wherein the isolated polynucleotide comprises a nucleic acid sequence encoding an engineered nuclease, and particularly an engineered meganuclease, of the invention. The invention further provides the use of an isolated polynucleotide in the manufacture of a medicament for treating hemophilia A, which is characterized by an inversion of exons 1-22 in the Factor VIII gene, wherein the isolated polynucleotide comprises a nucleic acid sequence encoding an engineered nuclease, and particularly an engineered meganuclease, of the invention.

In another aspect, the invention provides a recombinant AAV vector for use as a medicament, wherein the recombinant AAV vector comprises an isolated polynucleotide, and wherein the isolated polynucleotide comprises a nucleic acid sequence encoding an engineered nuclease, and particularly an engineered meganuclease, of the invention. The invention further provides the use of a recombinant AAV vector in the manufacture of a medicament for treating hemophilia A, which is characterized by an inversion of exons 1-22 of the Factor VIII gene, wherein the recombinant AAV vector comprises an isolated polynucleotide, and wherein the isolated polynucleotide comprises a nucleic acid sequence encoding an engineered nuclease, and particularly an engineered meganuclease, of the invention.

In another aspect, the invention provides a genetically-modified cell of the invention for use as a medicament, wherein the genetically-modified cell has been modified to comprise a wild-type Factor VIII gene. The invention further provides the use of a genetically-modified cell of the invention in the manufacture of a medicament for treating hemophilia A, which is characterized by an inversion of exons 1-22 of the Factor VIII gene, wherein the genetically-modified cell has been modified to comprise a wild-type Factor VIII gene.

BRIEF DESCRIPTION OF THE FIGURES

FIG. 1A shows a configuration in which int22h-3 is in an inverse orientation to int22h-1, allowing for intrachromosomal recombination to occur between these repeat sequences, resulting in the illustrated inversion of exons 1-22. FIG. 1B shows a configuration in which int22h-2 is in an inverse orientation to int22h-1, allowing for intrachromosomal recombination to occur between these repeat sequences, resulting in the illustrated inversion of exons 1-22.

FIG. 2. F8R recognition sequences in the Factor VIII gene. A) Each recognition sequence targeted by a recombinant meganuclease of the invention comprises two recognition half-sites. Each recognition half-site comprises 9 base pairs, separated by a 4 base pair central sequence. The F8R 1-2 recognition sequence (SEQ ID NO: 7) comprises two recognition half-sites referred to as F8R1 and F8R2. The F8R 3-4 recognition sequence (SEQ ID NO: 9) comprises two recognition half-sites referred to as F8R3 and F8R4. The F8R 9-10 recognition sequence (SEQ ID NO: 11) comprises two recognition half-sites referred to as F8R9 and F8R10. The F8R 11-12 recognition sequence (SEQ ID NO: 13) comprises two recognition half-sites referred to as F8R11 and F8R12. The F8R 13-14 recognition sequence (SEQ ID NO: 15) comprises two recognition half-sites referred to as F8R13 and F8R14. The F8R 15-16 recognition sequence (SEQ ID NO: 17) comprises two recognition half-sites referred to as F8R15 and F8R16.

FIGS. 5A-5G. Efficiency of recombinant meganucleases for recognizing and cleaving recognition sequences in the int22h-1 sequence of the Factor VIII gene in a CHO cell reporter assay. Recombinant meganucleases set forth in SEQ ID NOs: 19-21, 28-31, 40-43, 52-55, 64-67, and 76-79 were engineered to target the F8R 1-2 recognition sequence (SEQ ID NO: 7), the F8R 3-4 recognition sequence (SEQ ID NO: 9), the F8R 9-10 recognition sequence (SEQ ID NO: 11), the F8R 11-12 recognition sequence (SEQ ID NO: 13), the F8R 13-14 recognition sequence (SEQ ID NO: 15), or the F8R 15-16 recognition sequence (SEQ ID NO: 17), and were screened for efficacy in the CHO cell reporter assay. The results shown provide the percentage of GFP-expressing cells observed in each assay, which indicates the efficacy of each meganuclease for cleaving a target recognition sequence or the CHO-23/24 recognition sequence. A negative control (bs) was further included in each assay. FIG. 5A. shows meganucleases targeting the F8R 1-2 recognition sequence. FIG. 5B and FIG. 5C show meganucleases targeting the F8R 3-4 recognition sequence. FIG. 5D shows meganucleases targeting the F8R 9-10 recognition sequence. FIG. 5E shows meganucleases targeting the F8R 11-12 recognition sequence. FIG. 5F shows meganucleases targeting the F8R 13-14 recognition sequence. FIG. 5G shows meganucleases targeting the F8R 15-16 recognition sequence.

FIGS. 6A-6F. Efficiency of engineered meganucleases for recognizing and cleaving recognition sequences in the int22h-1 sequence of the Factor VIII gene in a CHO cell reporter assay. Engineered meganucleases encompassed by the invention were engineered to target the F8R 1-2 (SEQ ID NO: 7), F8R 3-4 (SEQ ID NO: 9), F8R 9-10 (SEQ ID NO: 11), F8R 11-12 (SEQ ID NO: 13), F8R 13-14 (SEQ ID NO: 15), or F8R 15-16 (SEQ ID NO: 17) recognition sequences, and were screened for efficacy in the CHO cell reporter assay at multiple time points over 12 days after nucleofection. The results shown provide the percentage of GFP-expressing cells observed in each assay over the 12 day period of analysis, which indicates the efficacy of each meganuclease for cleaving a target recognition sequence or the CHO-23/24 recognition sequence as a function of time. FIG. 6A shows F8R 1-2 meganucleases targeting the F8R 1-2 recognition sequence. FIG. 6B shows F8R 3-4 meganucleases targeting the F8R 3-4 recognition sequence. FIG. 6C shows F8R 9-10 meganucleases targeting the F8R 9-10 recognition sequence. FIG. 6D shows F8R 11-12 meganucleases targeting the F8R 11-12 recognition sequence. FIG. 6E shows F8R 13-14 meganucleases targeting the F8R 13-14 recognition sequence. FIG. 6F shows F8R 15-16 meganucleases targeting the F8R 15-16 recognition sequence.

FIGS. 12A-12B. Reversion of Factor VIII gene by F8R nucleases in primary human patient T cells and determination of editing by long-distance PCR. Hemophilia A patient T-cells were transfected with mRNA encoding F8R3-4x.43, F8R11-12x.69, or F8R15-16x.14 nucleases, respectively. At 3 days post-transfection, genomic DNA was isolated from cells and long-distance PCR was performed to determine Factor VIII genome editing. FIG. 12A shows PCR bands corresponding to a wild-type Factor VIII gene configuration, as detected using primers H1U and H1D. FIG. 12B shows PCR bands corresponding to the hemophilia A-associated Factor VIII gene inversion, as detected using primers H3D and H1D.

BRIEF DESCRIPTION OF THE SEQUENCES

Figure 1A:
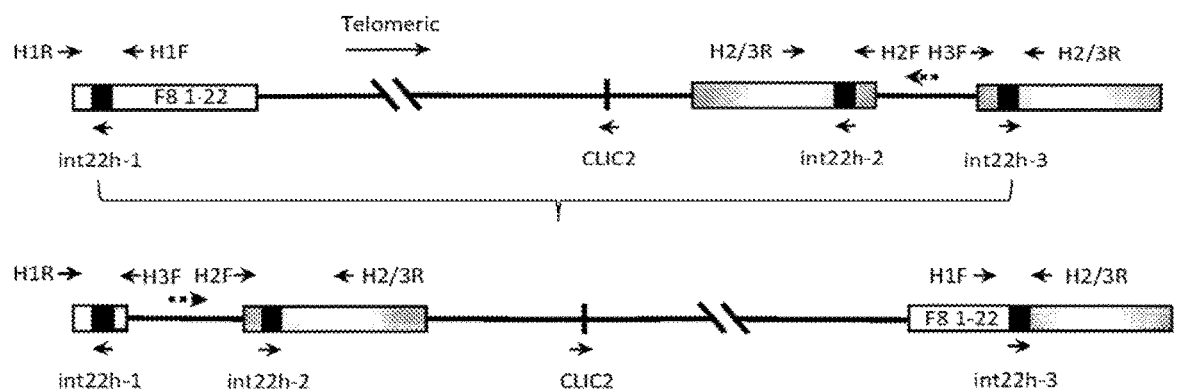
FIG. 1A and FIG. 1B. Inversion of exons 1-22 in the Factor VIII gene. The int22h-2 and int22h-3 repeat sequences are positioned telomeric to the int22h-1 sequence on the X chromosome. Further, int22h-2 and int22h-3 are found in an inverse orientation to one another as part of an imperfect palindrome. Recombination of sequences within this palindrome allows int22h-2 and in22h-3 to swap places in the genome and, consequently, change their orientation relative to int22h-1. As a result, the int22h-1 sequence can, in different circumstances, recombine with the int22h-2 repeat or the int22h-3 repeat, depending on which is in the opposite orientation to int22h-1.
Figure 1B:
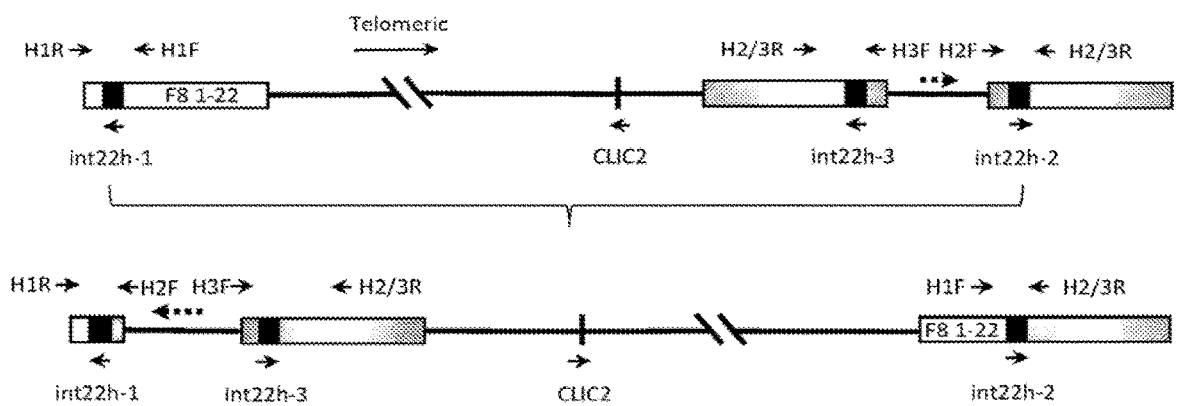
Figure 3:
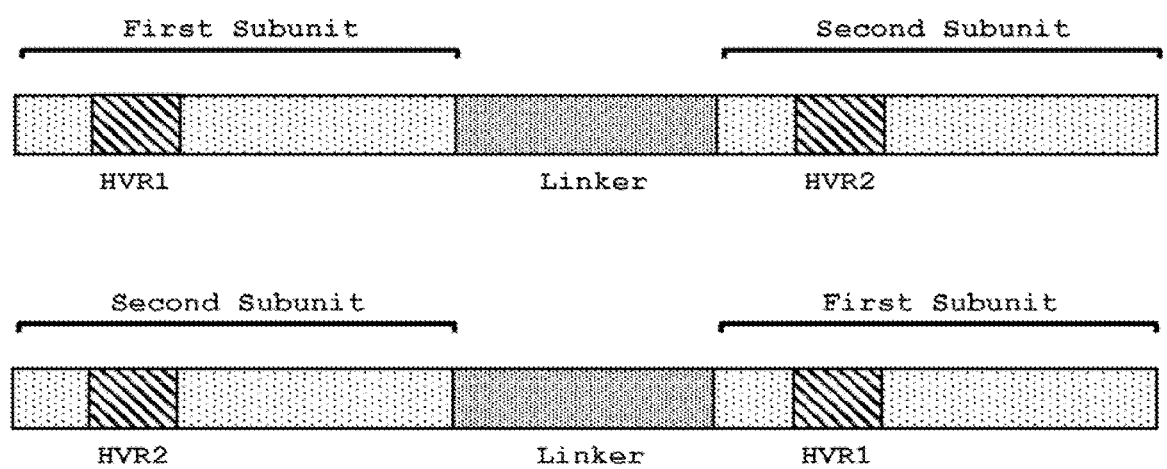
FIG. 3. The recombinant meganucleases of the invention comprise two subunits, wherein the first subunit comprising the HVR1 region binds to a first recognition half-site (e.g., F8R1, F8R3, F8R9, F8R11, F8R13, or F8R15) and the second subunit comprising the HVR2 region binds to a second recognition half-site (e.g., F8R2, F8R4, F8R10, F8R12, F8R14, or F8R16). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease from *Chlamydomonas reinhardtii.*

SEQ ID NO: 2 sets forth the amino acid sequence of the LAGLIDADG motif.

SEQ ID NO: 3 sets forth the nucleic acid sequence of a human int22h-1 sequence.

SEQ ID NO: 4 sets forth the nucleic acid sequence of a canine int22h-1 sequence.

SEQ ID NO: 5 sets forth the nucleic acid sequence of a human F8A1 sequence.

SEQ ID NO: 6 sets forth the nucleic acid sequence of a canine F8A1 sequence.

SEQ ID NO: 7 sets forth the nucleic acid sequence of the F8R 1-2 recognition sequence (sense).

SEQ ID NO: 8 sets forth the nucleic acid sequence of the F8R 1-2 recognition sequence (antisense).

SEQ ID NO: 9 sets forth the nucleic acid sequence of the F8R 3-4 recognition sequence (sense).

SEQ ID NO: 10 sets forth the nucleic acid sequence of the F8R 3-4 recognition sequence (antisense).

SEQ ID NO: 11 sets forth the nucleic acid sequence of the F8R 9-10 recognition sequence (sense).

SEQ ID NO: 12 sets forth the nucleic acid sequence of the F8R 9-10 recognition sequence (antisense).

SEQ ID NO: 13 sets forth the nucleic acid sequence of the F8R 11-12 recognition sequence (sense).

SEQ ID NO: 14 sets forth the nucleic acid sequence of the F8R 11-12 recognition sequence (antisense).

SEQ ID NO: 15 sets forth the nucleic acid sequence of the F8R 13-14 recognition sequence (sense).

SEQ ID NO: 16 sets forth the nucleic acid sequence of the F8R 13-14 recognition sequence (antisense).

SEQ ID NO: 17 sets forth the nucleic acid sequence of the F8R 15-16 recognition sequence (sense).

SEQ ID NO: 18 sets forth the nucleic acid sequence of the F8R 15-16 recognition sequence (antisense).

SEQ ID NO: 19 sets forth the amino acid sequence of the F8R 1-2x.27 meganuclease.

SEQ ID NO: 20 sets forth the amino acid sequence of the F8R 1-2x.15 meganuclease.

SEQ ID NO: 21 sets forth the amino acid sequence of the F8R 1-2x.9 meganuclease.

SEQ ID NO: 22 sets forth the amino acid sequence of the F8R 1-2x.27 meganuclease F8R1-binding monomer.

SEQ ID NO: 23 sets forth the amino acid sequence of the F8R 1-2x.15 meganuclease F8R1-binding monomer.

SEQ ID NO: 24 sets forth the amino acid sequence of the F8R 1-2x.9 meganuclease F8R1-binding monomer.

SEQ ID NO: 25 sets forth the amino acid sequence of the F8R 1-2x.27 meganuclease F8R2-binding monomer.

SEQ ID NO: 26 sets forth the amino acid sequence of the F8R 1-2x.15 meganuclease F8R2-binding monomer.

SEQ ID NO: 27 sets forth the amino acid sequence of the F8R 1-2x.9 meganuclease F8R2-binding monomer.

SEQ ID NO: 28 sets forth the amino acid sequence of the F8R 3-4x.43 meganuclease.

SEQ ID NO: 29 sets forth the amino acid sequence of the F8R 3-4x.70 meganuclease.

SEQ ID NO: 30 sets forth the amino acid sequence of the F8R 3-4x.4 meganuclease.

SEQ ID NO: 31 sets forth the amino acid sequence of the F8R 3-4L.5 meganuclease.

SEQ ID NO: 32 sets forth the amino acid sequence of the F8R 3-4x.43 meganuclease F8R3-binding monomer.

SEQ ID NO: 33 sets forth the amino acid sequence of the F8R 3-4x.70 meganuclease F8R3-binding monomer.

SEQ ID NO: 34 sets forth the amino acid sequence of the F8R 3-4x.4 meganuclease F8R3-binding monomer.

SEQ ID NO: 35 sets forth the amino acid sequence of the F8R 3-4L.5 meganuclease F8R3-binding monomer.

SEQ ID NO: 36 sets forth the amino acid sequence of the F8R 3-4x.43 meganuclease F8R4-binding monomer.

SEQ ID NO: 37 sets forth the amino acid sequence of the F8R 3-4x.70 meganuclease F8R4-binding monomer.

SEQ ID NO: 38 sets forth the amino acid sequence of the F8R 3-4x.4 meganuclease F8R4-binding monomer.

SEQ ID NO: 39 sets forth the amino acid sequence of the F8R 3-4L.5 meganuclease F8R4-binding monomer.

SEQ ID NO: 40 sets forth the amino acid sequence of the F8R 9-10x.70 meganuclease.

SEQ ID NO: 41 sets forth the amino acid sequence of the F8R 9-10x.38 meganuclease.

SEQ ID NO: 42 sets forth the amino acid sequence of the F8R 9-10x.2 meganuclease.

SEQ ID NO: 43 sets forth the amino acid sequence of the F8R 9-10x.8 meganuclease.

SEQ ID NO: 44 sets forth the amino acid sequence of the F8R 9-10x.70 meganuclease F8R9-binding monomer.

SEQ ID NO: 45 sets forth the amino acid sequence of the F8R 9-10x.38 meganuclease F8R9-binding monomer.

SEQ ID NO: 46 sets forth the amino acid sequence of the F8R 9-10x.2 meganuclease F8R9-binding monomer.

SEQ ID NO: 47 sets forth the amino acid sequence of the F8R 9-10x.8 meganuclease F8R9-binding monomer.

SEQ ID NO: 48 sets forth the amino acid sequence of the F8R 9-10x.70 meganuclease F8R10-binding monomer.

SEQ ID NO: 49 sets forth the amino acid sequence of the F8R 9-10x.38 meganuclease F8R10-binding monomer.

SEQ ID NO: 50 sets forth the amino acid sequence of the F8R 9-10x.2 meganuclease F8R10-binding monomer.

SEQ ID NO: 51 sets forth the amino acid sequence of the F8R 9-10x.8 meganuclease F8R10-binding monomer.

SEQ ID NO: 52 sets forth the amino acid sequence of the F8R 11-12x.56 meganuclease.

SEQ ID NO: 53 sets forth the amino acid sequence of the F8R 11-12x.69 meganuclease.

SEQ ID NO: 54 sets forth the amino acid sequence of the F8R 11-12x.66 meganuclease.

SEQ ID NO: 55 sets forth the amino acid sequence of the F8R 11-12x.41 meganuclease.

SEQ ID NO: 56 sets forth the amino acid sequence of the F8R 11-12x.56 meganuclease F8R11-binding monomer.

SEQ ID NO: 57 sets forth the amino acid sequence of the F8R 11-12x.69 meganuclease F8R11-binding monomer.

SEQ ID NO: 58 sets forth the amino acid sequence of the F8R 11-12x.66 meganuclease F8R11-binding monomer.

SEQ ID NO: 59 sets forth the amino acid sequence of the F8R 11-12x.41 meganuclease F8R11-binding monomer.

SEQ ID NO: 60 sets forth the amino acid sequence of the F8R 11-12x.56 meganuclease F8R12-binding monomer.

SEQ ID NO: 61 sets forth the amino acid sequence of the F8R 11-12x.69 meganuclease F8R12-binding monomer.

SEQ ID NO: 62 sets forth the amino acid sequence of the F8R 11-12x.66 meganuclease F8R12-binding monomer.

SEQ ID NO: 63 sets forth the amino acid sequence of the F8R 11-12x.41 meganuclease F8R12-binding monomer.

SEQ ID NO: 64 sets forth the amino acid sequence of the F8R 13-14x.13 meganuclease.

SEQ ID NO: 65 sets forth the amino acid sequence of the F8R 13-14x.3 meganuclease.

SEQ ID NO: 66 sets forth the amino acid sequence of the F8R 13-14x.1 meganuclease.

SEQ ID NO: 67 sets forth the amino acid sequence of the F8R 13-14x.11 meganuclease.

SEQ ID NO: 68 sets forth the amino acid sequence of the F8R 13-14x.13 meganuclease F8R13-binding monomer.

SEQ ID NO: 69 sets forth the amino acid sequence of the F8R 13-14x.3 meganuclease F8R13-binding monomer.

SEQ ID NO: 70 sets forth the amino acid sequence of the F8R 13-14x.1 meganuclease F8R13-binding monomer.

SEQ ID NO: 71 sets forth the amino acid sequence of the F8R 13-14x.11 meganuclease F8R13-binding monomer.

SEQ ID NO: 72 sets forth the amino acid sequence of the F8R 13-14x.13 meganuclease F8R14-binding monomer.

SEQ ID NO: 73 sets forth the amino acid sequence of the F8R 13-14x.3 meganuclease F8R14-binding monomer.

SEQ ID NO: 74 sets forth the amino acid sequence of the F8R 13-14x.1 meganuclease F8R14-binding monomer.

SEQ ID NO: 75 sets forth the amino acid sequence of the F8R 13-14x.11 meganuclease F8R14-binding monomer.

SEQ ID NO: 76 sets forth the amino acid sequence of the F8R 15-16x.14 meganuclease.

SEQ ID NO: 77 sets forth the amino acid sequence of the F8R 15-16x.85 meganuclease.

SEQ ID NO: 78 sets forth the amino acid sequence of the F8R 15-16x.4 meganuclease.

SEQ ID NO: 79 sets forth the amino acid sequence of the F8R 15-16x.79 meganuclease.

SEQ ID NO: 80 sets forth the amino acid sequence of the F8R 15-16x.14 meganuclease F8R15-binding monomer.

SEQ ID NO: 81 sets forth the amino acid sequence of the F8R 15-16x.85 meganuclease F8R15-binding monomer.

SEQ ID NO: 82 sets forth the amino acid sequence of the F8R 15-16x.4 meganuclease F8R15-binding monomer.

SEQ ID NO: 83 sets forth the amino acid sequence of the F8R 15-16x.79 meganuclease F8R15-binding monomer.

SEQ ID NO: 84 sets forth the amino acid sequence of the F8R 15-16x.14 meganuclease F8R16-binding monomer.

SEQ ID NO: 85 sets forth the amino acid sequence of the F8R 15-16x.85 meganuclease F8R16-binding monomer.

SEQ ID NO: 86 sets forth the amino acid sequence of the F8R 15-16x.4 meganuclease F8R16-binding monomer.

SEQ ID NO: 87 sets forth the amino acid sequence of the F8R 15-16x.79 meganuclease F8R16-binding monomer.

SEQ ID NO: 88 sets forth the nucleic acid sequence of the U1 primer.

SEQ ID NO: 89 sets forth the nucleic acid sequence of the D1 primer.

SEQ ID NO: 90 sets forth the nucleic acid sequence of the U3 primer.

SEQ ID NO: 91 sets forth the nucleic acid sequence of the FWD1 primer.

SEQ ID NO: 92 sets forth the nucleic acid sequence of the REV1 primer.

SEQ ID NO: 93 sets froth the nucleic acid sequence of the FWD3 primer.

SEQ ID NO: 94 sets forth the nucleic acid sequence of the H1U primer.

SEQ ID NO: 95 sets forth the nucleic acid sequence of the H1D primer.

SEQ ID NO: 96 sets forth the nucleic acid sequence of the H3D primer.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes which cleave a phosphodiester bond within a polynucleotide chain.

As used herein, the term "meganuclease" refers to an endonuclease that binds double-stranded DNA at a recognition sequence that is greater than 12 base pairs. Preferably, the recognition sequence for a meganuclease of the invention is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859). A meganuclease as used herein binds to double-stranded DNA as a heterodimer. A meganuclease may also be a "single-chain meganuclease" in which a pair of DNA-binding domains are joined into a single polypeptide using a peptide linker. The term "homing endonuclease" is synonymous with the term "meganuclease." Meganucleases of the invention are substantially non-toxic when expressed in cells without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will recognize non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. No. 8,445,251. In some embodiments, a linker may have an amino acid sequence comprising residues 154-195 of any one of SEQ ID NOs: 19-21, 28-31, 40-43, 52-55, 64-67, or 76-79.

As used herein, the term "TALEN" refers to an endonuclease comprising a DNA-binding domain comprising 16-22 TAL domain repeats fused to any portion of the FokI nuclease domain.

As used herein, the term "Compact TALEN" refers to an endonuclease comprising a DNA-binding domain with 16-22 TAL domain repeats fused in any orientation to any portion of the I-TevI homing endonuclease.

As used herein, the term "zinc finger nuclease" or "ZFN" refers to a chimeric endonuclease comprising a zinc finger DNA-binding domain fused to the nuclease domain of the FokI restriction enzyme. The zinc finger domain can be redesigned through rational or experimental means to produce a protein which binds to a pre-determined DNA sequence ~18 basepairs in length, comprising a pair of nine basepair half-sites separated by 2-10 basepairs. Cleavage by a zinc finger nuclease can create a blunt end or a 5' overhand of variable length (frequently four basepairs).

As used herein, the term "CRISPR" refers to a caspase-based endonuclease comprising a caspase, such as Cas9, and a guide RNA that directs DNA cleavage of the caspase by hybridizing to a recognition site in the genomic DNA.

As used herein, the term "megaTAL" refers to a single-chain endonuclease comprising a transcription activator-like effector (TALE) DNA binding domain with an engineered, sequence-specific homing endonuclease.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the term "recognition sequence" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a Compact TALEN, the recognition sequence comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a Compact TALEN produces two basepair 3' overhangs. In the case of a CRISPR, the recognition sequence is the sequence, typically 16-24 basepairs, to which the guide RNA binds to direct Cas9 cleavage. Cleavage by a CRISPR produced blunt ends. In the case of a zinc finger, the DNA binding domains typically recognize an 18-bp recognition sequence comprising a pair of nine basepair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, $K_d$. As used herein, a nuclease has "altered" binding affinity if the $K_d$ of the nuclease for a reference recognition sequence is increased or decreased by a statistically significant ($p<0.05$) amount relative to a reference nuclease.

As used herein, the term "specificity" means the ability of a meganuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific meganuclease is capable of cleaving only one or a very few recognition sequences. Specificity can be determined by any method known in the art. As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×–10×) relative to a reference meganuclease.

As used herein, the term "homologous recombination" or "HR" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), *J. Mol. Biol.* 215:403-410; Gish and States (1993), *Nature Genet.* 3:266-272; Madden et al. (1996), *Meth. Enzymol.*266:131-141; Altschul et al. (1997), *Nucleic Acids Res.* 25:33 89-3402); Zhang et al. (2000), *J. Comput. Biol.* 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 19-21, 28-31, 40-43, 52-55, 64-67, or 76-79. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-18 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 72, 73, 75, and 77 of any one of SEQ ID NOs: 19-21, 28-31, 40-43, 52-55, 64-67, or 76-79. In other embodiments, variable residues within a hypervariable region correspond to one or more of positions 215, 217, 219, 221, 223, 224, 229, 231, 233, 235, 237, 259, 261, 263, 264, 266, and 268 of any one of SEQ ID NOs: 19-21, 28-31, 40-43, 52-55, 64-67, or 76-79.

As used herein, the terms "Factor VIII gene," "F8 gene," and the like, refer to a gene located on the X chromosome which encodes the coagulation Factor VIII protein. In humans, the Factor VIII gene, identified by NCBI as Gene ID No. 2157, is located from base pair 154,835,788 to base pair 155,026,934 on the X chromosome. In canines, the Factor VIII gene can be the gene identified by NCBI Reference Sequence: NM_001003212.1. It is understood that the term "Factor VIII gene" can include both a wild-type Factor VIII gene and a Factor VIII gene which comprises naturally-occurring polymorphisms and/or mutations that allow for the production of a functional Factor VIII protein.

As used herein, the terms "int22h-1" and "int22h-1 sequence" refer to a sequence positioned within intron 22 of the Factor VIII gene having a size of approximately 9.5 kb (Bagnall et al. (2006) Journal of Thrombosis and Haemostasis 4:591-598) and can further refer to the human sequence identified by GenBank as Accession No. AY619999.1. The int22h-1 sequence is characterized as comprising a CpG island, a coding sequence for the H2AFB1 histone protein, and a coding sequence for the Factor VIII-Associated 1 protein (F8A1; also referred to as the intron 22 protein). The int22h-1 sequence is further characterized as being identical to, or having high homology with, at least one repeat sequence that is positioned telomeric to the Factor VIII gene on the X chromosome. In humans, two repeat sequences, referred to as int22h-2 and int22h-3, are positioned telomeric to the Factor VIII gene on the X chromosome. In particular embodiments of the invention, the human int22h-1 sequence can comprise SEQ ID NO: 3. In other particular embodiments of the invention, the canine int22h-1 sequence can comprise SEQ ID NO: 4.

As used herein, the terms "F8A1 coding sequence" and "intron 22 protein coding sequence" are used interchangeably and refer to a sequence positioned within the int22h-1 sequence which encodes the F8A1 protein. The F8A1 coding sequence is intronless and is transcribed in the opposite direction as the Factor VIII gene. In one embodiment, the wild-type human F8A1 coding sequence can comprise SEQ ID NO: 5. In another embodiment, the wild-type canine F8A1 coding sequence can comprise SEQ ID NO: 6, which has ~75% homology to the human F8A1 coding sequence. It is understood that reference to an F8A1 coding sequence includes a wild-type F8A1 sequence and an F8A1 sequence comprising naturally-occurring polymorphisms and/or mutations that allow for the production of a functional F8A1 protein.

As used herein, the terms "inversion" and "inversion of exons 1-22" refer to a mutation of a Factor VIII gene wherein an intra-chromosomal homologous recombination event occurs between the int22h-1 sequence of the Factor VIII gene and an identical or closely related, inversely oriented, repeat sequence positioned telomeric to the Factor VIII gene on the X chromosome, which results in an inversion of exons 1-22 with respect to exons 23-26.

As used herein, the term "reversion" refers to an intra-chromosomal homologous recombination event in a cell comprising an inversion of exons 1-22 of the Factor VIII gene, wherein a double-strand break is produced within the int22h-1 sequence to promote recombination with a repeat sequence telomeric to the Factor VIII gene on the X chromosome. Such recombination results in the corrected orientation of exons 1-22 and the production of a functional, wild-type Factor VIII gene.

The terms "recombinant DNA construct," "recombinant construct," "expression cassette," "expression construct," "chimeric construct," "construct," and "recombinant DNA fragment" are used interchangeably herein and are nucleic acid fragments. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, a "self-cleaving" recombinant DNA construct refers to a DNA construct which comprises at least one coding sequence for an endonuclease and at least one recognition sequence for the same endonuclease. When expressed in a cell (i.e., in vivo), the endonuclease recognizes and cleaves the recognition sequence, resulting in linearization of the DNA construct.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first proteins corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the terms "treatment" or "treating a subject" refers to the administration of an engineered nuclease of the invention, or a nucleic acid encoding an engineered nuclease of the invention, to a subject having hemophilia A for the purpose of correcting an inversion of exons 1-22 in the Factor VIII gene in cells which normally express Factor VIII in wild-type subjects. Such treatment results in correction of the Factor VIII gene in a number of cells sufficient to increase circulating levels of Factor VIII in the subject, and either partial or complete relief of one or more symptoms of hemophilia A in the subject. The terms "treatment" or "treating a subject" can further refer to the administration of a genetically-modified cell comprising a wild-type Factor VIII gene to a subject according the method of the invention, wherein the genetically-modified cell is delivered to a target tissue and either produces Factor VIII, or differentiates into a cell which produces Factor VIII, in an amount sufficient to increase the circulating levels of Factor VIII in the subject, resulting in either partial or complete relief of one or more symptoms of hemophilia A. In some aspects, an engineered nuclease of the invention, a nucleic acid encoding the same, or a genetically-modified cell of the invention is administered during treatment in the form of a pharmaceutical composition of the invention.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 00 and 02 if the variable is inherently continuous.

2.1 Principle of the Invention

The present invention is based, in part, on the hypothesis that engineered nucleases can be used to treat hemophilia A by correcting an inversion of exons 1-22 in the Factor VIII gene. More specifically, nucleases can be engineered to recognize and cleave a recognition sequence present within an int22h-1 sequence of the Factor VIII gene to produce a double-strand break. Intra-chromosomal homologous recombination can then occur between the int22h-1 sequence and a repeat sequence which is telomeric to the Factor VIII gene on the X chromosome, resulting in a reversion of exons 1-22 and the production of a functional, wild-type Factor VIII gene in target cells of the subject.

The invention is also based, in part, on the hypothesis that pluripotent cells (e.g., induced pluripotent stem (iPS) cells) comprising an inversion of exons 1-22 in the Factor VIII gene can be obtained and contacted with an engineered nuclease of the invention (or a nucleic acid encoding the same) in order to correct the Factor VIII gene by the same mechanism described above. Such pluripotent cells can then be administered to a subject having hemophilia A, wherein the cells are delivered to a target tissue (e.g., the liver or the circulatory system) and differentiate into cells which express wild-type Factor VIII in the subject.

Thus, the present invention encompasses engineered nucleases, and particularly engineered recombinant meganucleases, which recognize and cleave a recognition sequence within the int22h-1 sequence of a Factor VIII gene. The present invention also encompasses methods of using such engineered nucleases to make genetically-modified cells, and the use of such cells in a pharmaceutical composition and in methods for treating hemophilia A. Further, the invention encompasses pharmaceutical compositions comprising engineered nuclease proteins, nucleic acids encoding engineered nucleases, or genetically-modified cells of the invention, and the use of such compositions for the treatment of hemophilia A.

2.2 NUCLEASES FOR RECOGNIZING AND CLEAVING RECOGNITION SEQUENCES WITHIN AN INT22H-1 SEQUENCE OF THE FACTOR VIII GENE

It is known in the art that it is possible to use a site-specific nuclease to make a DNA break in the genome of a living cell, and that such a DNA break can result in permanent modification of the genome via homologous recombination of the cleaved target site with an identical or highly homologous DNA sequence within the genome.

Thus, in different embodiments, a variety of different types of endonuclease are useful for practicing the invention. In one embodiment, the invention can be practiced using engineered recombinant meganucleases. In another embodiment, the invention can be practiced using a CRISPR nuclease or CRISPR Nickase. Methods for making CRISPRs and CRISPR Nickases that recognize pre-determined DNA sites are known in the art, for example Ran, et al. (2013) Nat Protoc. 8:2281-308. In another embodiment, the invention can be practiced using TALENs or Compact TALENs. Methods for making TALE domains that bind to pre-determined DNA sites are known in the art, for example Reyon et al. (2012) Nat Biotechnol. 30:460-5. In another embodiment, the invention can be practiced using zinc finger nucleases (ZFNs). In a further embodiment, the invention can be practiced using megaTALs.

In preferred embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some examples, recombinant meganucleases of the invention have been engineered to recognize and cleave the F8R 1-2 recognition sequence (SEQ ID NO: 7). The F8R 1-2 recognition sequence is positioned within both the int22h-1 sequence and the F8A1 sequence. Such recombinant meganucleases are collectively referred to herein as "F8R 1-2 meganucleases." Exemplary F8R 1-2 meganucleases are provided in SEQ ID NOs: 19-22.

In additional examples, recombinant meganucleases of the invention have been engineered to recognize and cleave the F8R 3-4 recognition sequence (SEQ ID NO: 9). The F8R 3-4 recognition sequence is positioned within both the int22h-1 sequence and the F8A1 sequence. Such recombinant meganucleases are collectively referred to herein as "F8R 3-4 meganucleases." Exemplary F8R 3-4 meganucleases are provided in SEQ ID NOs: 28-31.

In additional examples, recombinant meganucleases of the invention have been engineered to recognize and cleave the F8R 9-10 recognition sequence (SEQ ID NO: 11). Such recombinant meganucleases are collectively referred to herein as "F8R 9-10 meganucleases." Exemplary F8R 9-10 meganucleases are provided in SEQ ID NOs: 40-43.

In additional examples, recombinant meganucleases of the invention have been engineered to recognize and cleave the F8R 11-12 recognition sequence (SEQ ID NO: 13). Such recombinant meganucleases are collectively referred to herein as "F8R 11-12 meganucleases." Exemplary F8R 11-12 meganucleases are provided in SEQ ID NOs: 52-55.

In additional examples, recombinant meganucleases of the invention have been engineered to recognize and cleave the F8R 13-14 recognition sequence (SEQ ID NO: 15). Such recombinant meganucleases are collectively referred to herein as "F8R 13-14 meganucleases." Exemplary F8R 13-14 meganucleases are provided in SEQ ID NOs: 64-67.

In additional examples, recombinant meganucleases of the invention have been engineered to recognize and cleave the F8R 15-16 recognition sequence (SEQ ID NO: 17). Such recombinant meganucleases are collectively referred to herein as "F8R 15-16 meganucleases." Exemplary F8R 15-16 meganucleases are provided in SEQ ID NOs: 76-79.

Recombinant meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the F8R1, F8R3, F8R9, F8R11, F8R13, or F8R15 half-site), and the second subunit binds to a second recognition half-site in the recognition sequence (e.g., the F8R2, F8R4, F8R10, F8R12, F8R14, or F8R16 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary F8R 1-2 meganucleases of the invention are provided in Table 1. Exemplary F8R 3-4 meganucleases of the invention are provided in Table 2. Exemplary F8R 9-10 meganucleases of the invention are provided in Table 3. Exemplary F8R 11-12 meganucleases of the invention are provided in Table 4. Exemplary F8R 13-14 meganucleases of the invention are provided in Table 5. Exemplary F8R 15-16 meganucleases of the invention are provided in Table 6.

TABLE 1

Exemplary recombinant meganucleases engineered to recognize and cleave the F8R 1-2 recognition sequence (SEQ ID NO: 7)

| Meganuclease | AA SEQ ID | F8R1 Subunit Residues | F8R1 Subunit SEQ ID | *F8R1 Subunit % | F8R2 Subunit Residues | F8R2 Subunit SEQ ID | *F8R2 Subunit % |
|---|---|---|---|---|---|---|---|
| F8R 1-2x.27 | 19 | 198-344 | 22 | 100 | 7-153 | 25 | 100 |
| F8R 1-2x.15 | 20 | 7-153 | 23 | 95.24 | 198-344 | 26 | 95.24 |
| F8R 1-2x.9 | 21 | 7-153 | 24 | 95.24 | 198-344 | 27 | 95.24 |

*"F8R1 Subunit %" and "F8R2 Subunit %" represent the amino acid sequence identity between the F8R1-binding and F8R2-binding subunit regions of each meganuclease and the F8R1-binding and F8R2-binding subunit regions, respectively, of the F8R 1-2x.27 meganuclease.

TABLE 2

Exemplary recombinant meganucleases engineered to recognize and cleave the F8R 3-4 recognition sequence (SEQ ID NO: 9)

| Meganuclease | AA SEQ ID | F8R3 Subunit Residues | F8R3 Subunit SEQ ID | *F8R3 Subunit % | F8R4 Subunit Residues | F8R4 Subunit SEQ ID | *F8R4 Subunit % |
|---|---|---|---|---|---|---|---|
| F8R 3-4x.43 | 28 | 198-344 | 32 | 100 | 7-153 | 36 | 100 |
| F8R 3-4x.70 | 29 | 198-344 | 33 | 98.64 | 7-153 | 37 | 91.16 |
| F8R 3-4x.4 | 30 | 198-344 | 34 | 100 | 7-153 | 38 | 98.64 |
| F8R 3-4L.5 | 31 | 198-344 | 35 | 98.64 | 7-153 | 39 | 97.28 |

*"F8R3 Subunit %" and "F8R4 Subunit %" represent the amino acid sequence identity between the F8R3-binding and F8R4-binding subunit regions of each meganuclease and the F8R3-binding and F8R4-binding subunit regions, respectively, of the F8R 3-4x.43 meganuclease.

TABLE 3

Exemplary recombinant meganucleases engineered to recognize and cleave the F8R 9-10 recognition sequence (SEQ ID NO: 11)

| Meganuclease | AA SEQ ID | F8R9 Subunit Residues | F8R9 Subunit SEQ ID | *F8R9 Subunit % | F8R10 Subunit Residues | F8R10 Subunit SEQ ID | *F8R10 Subunit % |
|---|---|---|---|---|---|---|---|
| F8R 9-10x.70 | 40 | 7-153 | 44 | 100 | 198-344 | 48 | 100 |
| F8R 9-10x.38 | 41 | 198-344 | 45 | 97.96 | 7-153 | 49 | 100 |
| F8R 9-10x.2 | 42 | 198-344 | 46 | 94.56 | 7-153 | 50 | 91.84 |
| F8R 9-10x.8 | 43 | 198-344 | 47 | 95.24 | 7-153 | 51 | 98.64 |

*"F8R9 Subunit %" and "F8R10 Subunit %" represent the amino acid sequence identity between the F8R9-binding and F8R10-binding subunit regions of each meganuclease and the F8R9-binding and F8R10-binding subunit regions, respectively, of the F8R 9-10x.70 meganuclease.

TABLE 4

Exemplary recombinant meganucleases engineered to recognize
and cleave the F8R 11-12 recognition sequence (SEQ ID NO: 13)

| Meganuclease | AA SEQ ID | F8R11 Subunit Residues | F8R11 Subunit SEQ ID | *F8R11 Subunit % | F8R12 Subunit Residues | F8R12 Subunit SEQ ID | *F8R12 Subunit % |
|---|---|---|---|---|---|---|---|
| F8R 11-12x.56 | 52 | 7-153 | 56 | 100 | 198-344 | 60 | 100 |
| F8R 11-12x.69 | 53 | 7-153 | 57 | 91.84 | 198-344 | 61 | 95.24 |
| F8R 11-12x.66 | 54 | 7-153 | 58 | 92.52 | 198-344 | 62 | 90.48 |
| F8R 11-12x.41 | 55 | 7-153 | 59 | 91.84 | 198-344 | 63 | 92.52 |

*"F8R11 Subunit %" and "F8R12 Subunit %" represent the amino acid sequence identity between the F8R11-binding and F8R12-binding subunit regions of each meganuclease and the F8R11-binding and F8R12-binding subunit regions, respectively, of the F8R 11-12x.56 meganuclease.

TABLE 5

Exemplary recombinant meganucleases engineered to recognize
and cleave the F8R 13-14 recognition sequence (SEQ ID NO: 15)

| Meganuclease | AA SEQ ID | F8R13 Subunit Residues | F8R13 Subunit SEQ ID | *F8R13 Subunit % | F8R14 Subunit Residues | F8R14 Subunit SEQ ID | *F8R14 Subunit % |
|---|---|---|---|---|---|---|---|
| F8R 13-14x.13 | 64 | 7-153 | 68 | 100 | 198-344 | 72 | 100 |
| F8R 13-14x.3 | 65 | 198-344 | 69 | 94.56 | 7-153 | 73 | 92.52 |
| F8R 13-14x.1 | 66 | 198-344 | 70 | 93.88 | 7-153 | 74 | 93.2 |
| F8R 13-14x.11 | 67 | 198-344 | 71 | 93.2 | 7-153 | 75 | 93.2 |

*"F8R13 Subunit %" and "F8R14 Subunit %" represent the amino acid sequence identity between the F8R13-binding and F8R14-binding subunit regions of each meganuclease and the F8R13-binding and F8R14-binding subunit regions, respectively, of the F8R 13-14x.13 meganuclease.

TABLE 6

Exemplary recombinant meganucleases engineered to recognize
and cleave the F8R 15-16 recognition sequence (SEQ ID NO: 17)

| Meganuclease | AA SEQ ID | F8R15 Subunit Residues | F8R15 Subunit SEQ ID | *F8R15 Subunit % | F8R16 Subunit Residues | F8R16 Subunit SEQ ID | *F8R16 Subunit % |
|---|---|---|---|---|---|---|---|
| F8R 15-16x.14 | 76 | 198-344 | 80 | 100 | 7-153 | 84 | 100 |
| F8R 15-16x.85 | 77 | 198-344 | 81 | 99.32 | 7-153 | 85 | 93.88 |
| F8R 15-16x.4 | 78 | 198-344 | 82 | 95.24 | 7-153 | 86 | 91.84 |
| F8R 15-16x.79 | 79 | 198-344 | 83 | 94.56 | 7-153 | 87 | 92.52 |

*"F8R15 Subunit %" and "F8R16 Subunit %" represent the amino acid sequence identity between the F8R15-binding and F8R16-binding subunit regions of each meganuclease and the F8R15-binding and F8R16-binding subunit regions, respectively, of the F8R 15-16x.14 meganuclease.

2.3 Methods for Delivering and Expressing Endonucleases

The invention provides methods for producing genetically-modified cells using engineered nucleases that recognize and cleave recognition sequences found within an intron 22 sequence of a Factor VIII gene. The invention further provides methods for treating hemophilia A in a subject by administering a pharmaceutical composition comprising a pharmaceutically acceptable carrier and an engineered nuclease of the invention (or a nucleic acid encoding the engineered nuclease). In each case, the invention requires that an engineered nuclease of the invention can be delivered to and/or expressed from DNA/RNA in appropriate cells that comprise an inversion of exons 1-22 in a Factor VIII gene and would typically express Factor VIII in a healthy subject (e.g., hepatic sinusoidal endothelial cells or hematopoietic endothelial cells, or progenitor cells which differentiate into the same).

Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA (e.g., mRNA). For embodiments in which the engineered nuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804):304-10) as well as inducible promoters such as the tetracycline-inducible promoter (Dingermann et al. (1992), Mol Cell Biol. 12(9):4038-45). An engineered nuclease of the invention can also be operably linked to a synthetic promoter. Synthetic promoters can include, without limitation, the JeT promoter (WO 2002/012514).

In some embodiments, mRNA encoding an endonuclease is delivered to a cell because this reduces the likelihood that the gene encoding the engineered nuclease will integrate into the genome of the cell. Such mRNA encoding an engineered nuclease can be produced using methods known in the art such as in vitro transcription. In some embodiments, the mRNA is capped using 7-methyl-guanosine. In some embodiments, the mRNA may be polyadenylated.

In another particular embodiment, a nucleic acid encoding an endonuclease of the invention can be introduced into the cell using a single-stranded DNA template. The single-stranded DNA can further comprise a 5' and/or a 3' AAV inverted terminal repeat (ITR) upstream and/or downstream of the sequence encoding the engineered nuclease. In other embodiments, the single-stranded DNA can further comprise a 5' and/or a 3' homology arm upstream and/or downstream of the sequence encoding the engineered nuclease.

In another particular embodiment, genes encoding an endonuclease of the invention can be introduced into a cell using a linearized DNA template. In some examples, a plasmid DNA encoding an endonuclease can be digested by one or more restriction enzymes such that the circular plasmid DNA is linearized prior to being introduced into a cell.

In another particular embodiment, genes encoding an endonuclease of the invention can be introduced into a cell on a self-cleaving recombinant DNA construct. Such a construct can comprise at least one coding sequence for an endonuclease and at least one recognition sequence for the same endonuclease. When expressed in a cell (i.e., in vivo), the endonuclease recognizes and cleaves the recognition sequence, resulting in linearization of the DNA construct.

Purified nuclease proteins can be delivered into cells to cleave genomic DNA by a variety of different mechanisms known in the art, including those further detailed herein below.

The target tissue(s) for delivery of recombinant meganucleases of the invention include, without limitation, cells of the liver, preferably hepatic sinusoidal endothelial cells or, alternatively, progenitor cells which differentiate into hepatic sinusoidal endothelial cells. Target tissues can also include, without limitation, cells in the circulatory system, preferably hematopoietic endothelial cells or, alternatively, progenitor cells which differentiate into hematopoietic endothelial cells. As discussed, endonucleases of the invention can be delivered as purified protein or as RNA or DNA encoding the endonucleases. In one embodiment, endonuclease proteins, or mRNA, or DNA vectors encoding endonucleases, are supplied to target cells (e.g., cells in the liver or cells in the circulatory system) via injection directly to the target tissue. Alternatively, endonuclease protein, mRNA, or DNA can be delivered systemically via the circulatory system.

In some embodiments, endonuclease proteins, or DNA/mRNA encoding endonucleases, are formulated for systemic administration, or administration to target tissues, in a pharmaceutically acceptable carrier in accordance with known techniques. See, e.g., Remington, The Science And Practice of Pharmacy (21st ed. 2005). In the manufacture of a pharmaceutical formulation according to the invention, proteins/RNA/mRNA are typically admixed with a pharmaceutically acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation.

In some embodiments, endonuclease proteins, or DNA/mRNA encoding the endonuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706, and HSV-1 VP-22 (Deshayes et al. (2005) Cell Mol Life Sci. 62:1839-49. In an alternative embodiment, endonuclease proteins, or DNA/mRNA encoding endonucleases, are coupled covalently or non-covalently to an antibody that recognizes a specific cell-surface receptor expressed on target cells such that the endonuclease protein/DNA/mRNA binds to and is internalized by the target cells. Alternatively, endonuclease protein/DNA/mRNA can be coupled covalently or non-covalently to the natural ligand (or a portion of the natural ligand) for such a cell-surface receptor. (McCall, et al. (2014) Tissue Barriers. 2(4):e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, endonuclease proteins, or DNA/mRNA encoding endonucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, endonuclease proteins, or DNA/mRNA encoding endonucleases, are coupled covalently or, preferably, non-covalently to a nanoparticle or encapsulated within such a nanoparticle using methods known in the art (Sharma, et al. (2014) Biomed Res Int. 2014). A nanoparticle is a nanoscale delivery system whose length scale is <1 μm, preferably <100 nm. Such nanoparticles may be designed using a core composed of metal, lipid, polymer, or biological macromolecule, and multiple copies of the endonuclease proteins, mRNA, or DNA can be attached to or encapsulated with the nanoparticle core. This increases the copy number of the protein/mRNA/DNA that is delivered to each cell and, so, increases the intracellular expression of each endonuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the endonuclease proteins or DNA/mRNA encoding the endonucleases are encapsulated within liposomes or complexed using cationic lipids (see, e.g., Lipofectamine™, Life Technologies Corp., Carlsbad, Calif.; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, endonuclease proteins, or DNA/mRNA encoding endonucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, endonuclease proteins, or DNA/mRNA encoding recombinant meganucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, endonuclease proteins, or DNA/mRNA encoding endonucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, endonuclease proteins, or DNA/mRNA encoding endonucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding an endonuclease are delivered using a viral vector. Such vectors are known in the art and include retroviral vectors, lentiviral vectors, adenoviral vectors, and adeno-associated virus (AAV) vectors (reviewed in Vannucci, et al. (2013 New Microbiol. 36:1-22). In some embodiments, the viral vectors are injected directly into target tissues. In alternative embodiments, the viral vectors are delivered systemically via the circulatory system. It is known in the art that different AAV vectors tend to localize to different tissues. In liver target tissues, effective transduction of hepatocytes has been shown, for example, with AAV serotypes 2, 8, and 9 (Sands (2011) Methods Mol. Biol. 807:141-157). AAV vectors can also be self-complementary such that they do not require second-strand DNA synthesis in the host cell (McCarty, et al. (2001) Gene Ther. 8:1248-54).

In one embodiment, a viral vector used for endonuclease gene delivery is a self-limiting viral vector. A self-limiting viral vector can have limited persistence time in a cell or organism due to the presence of a recognition sequence for a recombinant meganuclease within the vector. Thus, a self-limiting viral vector can be engineered to provide coding for a promoter, an endonuclease described herein, and an endonuclease recognition site within the ITRs. The self-limiting viral vector delivers the endonuclease gene to a cell, tissue, or organism, such that the endonuclease is expressed and able to cut the genome of the cell at an endogenous recognition sequence within the genome. The delivered endonuclease will also find its target site within the self-limiting viral vector itself, and cut the vector at this target site. Once cut, the 5' and 3' ends of the viral genome will be exposed and degraded by exonucleases, thus killing the virus and ceasing production of the endonuclease.

If the endonuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cells. Examples of liver-specific promoters include, without limitation, human alpha-1 antitrypsin promoter and apolipoprotein A-II promoter.

It is envisioned that a single treatment will permanently cause a reversion of exons 1-22 in the Factor VIII gene, resulting in a functional, wild-type gene in a percentage of patient target cells. If the frequency of reversion is low, however, or if a large percentage of target cells need to be corrected, it may be necessary to perform multiple treatments on each patient.

2.4 Pharmaceutical Compositions

In some embodiments, the invention provides a pharmaceutical composition comprising a pharmaceutically acceptable carrier and engineered nuclease of the invention, or a pharmaceutically acceptable carrier and an isolated polynucleotide comprising a nucleic acid encoding an engineered nuclease of the invention. In other embodiments, the invention provides a pharmaceutical composition comprising a pharmaceutically acceptable carrier and a genetically-modified cell of the invention which can be delivered to a target tissue where the cell can then differentiate into a cell which expresses wild-type Factor VIII. Pharmaceutical compositions of the invention can be useful for treating a subject having hemophilia A, wherein the disease is characterized by an inversion of exons 1-22 in a Factor VIII gene.

Such pharmaceutical compositions can be prepared in accordance with known techniques. See, e.g., Remington, The Science and Practice of Pharmacy (21st ed. 2005). In the manufacture of a pharmaceutical formulation according to the invention, endonuclease polypeptides (or DNA/RNA encoding the same) are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

2.5 Methods for Producing Recombinant Aav Vectors

In some embodiments, the invention provides recombinant AAV vectors for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the site-specific endonuclease is not expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

1. The endonuclease can be placed under the control of a tissue-specific promoter that is not active in the packaging cells. For example, if a viral vector is developed for delivery of (an) endonuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human α1-antitrypsin (such as PalAT), and hemopexin (such as Phpx) (Kramer, M G et al., (2003) Mol. Therapy 7:375-85). Examples of eye-specific promoters include opsin, and corneal epithelium-specific K12 promoters (Martin K R G, Klein R L, and Quigley H A (2002) Methods (28): 267-75) (Tong Y, et al., (2007) J Gene Med, 9:956-66). These promoters, or other tissue-specific promoters known in the art, are not highly-active in HEK-293 cells and, thus, will not be expected to yield significant levels of endonuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASBS (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) PLoS One v.5(8):e12274).

2. Alternatively, the vector can be packaged in cells from a different species in which the endonuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) J. Biotechnol. 131(2):138-43). An endonuclease under the control of a mammalian promoter is unlikely to be expressed in these cells (Airenne, K J, et al. (2013) Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of an endonuclease. Because these introns are not spliced efficiently from pre-mRNA transcripts in insect cells, insect cells will not express a functional endonuclease and will package the full-length genome. In contrast, mammalian cells to which the resulting recombinant AAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

3. The endonuclease gene can be operably linked to an inducible promoter such that a small-molecule inducer is required for endonuclease expression. Examples of inducible promoters include the Tet-On system (Clontech; Chen H., et al., (2015) BMC Biotechnol. 15(1):4)) and the RheoSwitch system (Intrexon; Sowa G., et al., (2011) Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome The latter step is necessary because the endonuclease will not be expressed in the target cells or tissues following recombinant AAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, recombinant AAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the endonuclease gene will be repressed only in the packaging cells expressing the repressor and not in target cells or tissues transduced with the resulting recombinant AAV vector.

2.6 Engineered Nuclease Variants

Embodiments of the invention encompass the engineered nucleases described herein, and variants thereof. Further embodiments of the invention encompass isolated polynucleotides comprising a nucleic acid sequence encoding the endonucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave recognition sequences found in an int22h-1 sequence in a Factor VIII gene including, for example, the F8R 1-2 recognition sequence (SEQ ID NO: 7), the F8R 3-4 recognition sequence (SEQ ID NO: 9), the F8R 9-10 recognition sequence (SEQ ID NO: 11), the F8R 11-12 recognition sequence (SEQ ID NO: 13), the F8R 13-14 recognition sequence (SEQ ID NO: 15), or the F8R 15-16 recognition sequence (SEQ ID NO: 17). Such variants may result, for example, from human manipulation. Biologically active variants of a native polypeptide of the embodiments (e.g., SEQ ID NOs: 19-21, 28-31, 40-43, 52-55, 64-67, or 76-79), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 7 provides potential substitutions that can be made in a recombinant meganuclease monomer or subunit to enhance specificity based on the base present at each half-site position (−1 through −9) of a recognition half-site.

TABLE 7

| Posn. | Favored Sense-Strand Base | | | | | | | | | |
|---|---|---|---|---|---|---|---|---|---|---|
| | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | E46* | Q75* | | | | | | | |
| | A46* | R46* | D46* | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | S26* | |
| | Q77 | K26* | E26* | | | | | Q26* | | | |
| −5 | | E42 | R42 | | | | K28* C28* | | | M66 | |
| | | | | | | | Q42 | | | K66 | |
| −6 | Q40 | E40 | R40 | C40 | A40 | | | | | S40 | |
| | C28* | R28* | | I40 | A79 | | | | | S28* | |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | C38 | | | | H38 | |
| | Q38 | K30* | R38 | L38 | | | | | | N38 | |
| | | R30* | E30* | | | | | | | Q30* | |
| −8 | F33 | E33 | F33 | L33 | | R32* R33 | | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | S32 | |
| | | | K32 | V32 | | | | I32 | | N32 | |
| | | | | A32 | | | | | | H32 | |
| | | | | C32 | | | | | | Q32 | |
| | | | | | | | | | | T32 | |

Bold entries are wild-type contact residues and do not constitute "modifications" as used herein.
An asterisk indicates that the residue contacts the base on the antisense strand.

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave recognition sequences found within an int22h-1 sequence of a Factor VIII gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Recognize and Cleave F8R Recognition Sequences 1. Meganucleases that Recognize and Cleave the F8R 1-2 Recognition Sequence Recombinant meganucleases (SEQ ID NOs: 19-21), collectively referred to herein as "F8R 1-2 meganucleases," were engineered to recognize and cleave the F8R 1-2 recognition sequence (SEQ ID NO: 7), which is present in the human and canine Factor VIII gene, specifically within the int22h-1 sequence, and more specifically within the F8A1 sequence. Each F8R 1-2 recombinant meganuclease comprises an N-terminal nuclease-localization signal derived from SV40, a first meganuclease subunit, a linker sequence, and a second meganuclease subunit. A first subunit in each F8R 1-2 meganuclease binds to the F8R1 recognition half-site of SEQ ID NO: 7, while a second subunit binds to the F8R2 recognition half-site (see, FIG. 2).

The F8R1-binding subunits and F8R2-binding subunits each comprise a 56 base pair hypervariable region, referred to as HVR1 and HVR2, respectively. F8R1-binding subunits are highly conserved outside of the HVR1 region. Similarly, F8R2-binding subunits are also highly conserved outside of the HVR2 region. The F8R1-binding regions of SEQ ID NOs: 19-21 are provided as SEQ ID NOs: 22-24, respectively. Each of SEQ ID NOs: 22-24 share at least 90% sequence identity to SEQ ID NO: 22, which is the F8R1-binding region of the meganuclease F8R 1-2x.27 (SEQ ID NO: 19). F8R2-binding regions of SEQ ID NOs: 19-21 are provided as SEQ ID NOs: 25-27, respectively. Each of SEQ ID NOs: 25-27 share at least 90% sequence identity to SEQ ID NO: 25, which is the F8R2-binding region of the meganuclease F8R 1-2x.27 (SEQ ID NO: 19).

2. Meganucleases that Recognize and Cleave the F8R 3-4 Recognition Sequence

Recombinant meganucleases (SEQ ID NOs: 28-31), collectively referred to herein as "F8R 3-4 meganucleases," were engineered to recognize and cleave the F8R 3-4 recognition sequence (SEQ ID NO: 9), which is present in the human and canine Factor VIII gene, specifically within the int22h-1 sequence, and more specifically within the F8A1 sequence. Each F8R 3-4 recombinant meganuclease comprises an N-terminal nuclease-localization signal derived from SV40, a first meganuclease subunit, a linker sequence, and a second meganuclease subunit. A first subunit in each F8R 3-4 meganuclease binds to the F8R3 recognition half-site of SEQ ID NO: 9, while a second subunit binds to the F8R4 recognition half-site (see, FIG. 2).

The F8R3-binding subunits and F8R4-binding subunits each comprise a 56 base pair hypervariable region, referred to as HVR1 and HVR2, respectively. F8R3-binding subunits are highly conserved outside of the HVR1 region. Similarly, F8R4-binding subunits are also highly conserved outside of the HVR2 region. The F8R3-binding regions of SEQ ID NOs: 28-31 are provided as SEQ ID NOs: 32-35, respectively. Each of SEQ ID NOs: 32-35 share at least 90% sequence identity to SEQ ID NO: 32, which is the F8R3-binding region of the meganuclease F8R 3-4x.43 (SEQ ID NO: 28). F8R4-binding regions of SEQ ID NOs: 28-31 are provided as SEQ ID NOs: 36-39, respectively. Each of SEQ ID NOs: 36-39 share at least 90% sequence identity to SEQ ID NO: 36, which is the F8R4-binding region of the meganuclease F8R 3-4x.43 (SEQ ID NO: 28).

3. Meganucleases that Recognize and Cleave the F8R 9-10 Recognition Sequence

Recombinant meganucleases (SEQ ID NOs: 40-43), collectively referred to herein as "F8R 9-10 meganucleases," were engineered to recognize and cleave the F8R 9-10 recognition sequence (SEQ ID NO: 11), which is present in the human and canine Factor VIII gene, specifically within the int22h-1 sequence. Each F8R 9-10 recombinant meganuclease comprises an N-terminal nuclease-localization signal derived from SV40, a first meganuclease subunit, a linker sequence, and a second meganuclease subunit. A first subunit in each F8R 9-10 meganuclease binds to the F8R9 recognition half-site of SEQ ID NO: 11, while a second subunit binds to the F8R10 recognition half-site (see, FIG. 2).

The F8R9-binding subunits and F8R10-binding subunits each comprise a 56 base pair hypervariable region, referred to as HVR1 and HVR2, respectively. F8R9-binding subunits are highly conserved outside of the HVR1 region. Similarly, F8R10-binding subunits are also highly conserved outside of the HVR2 region. The F8R9-binding regions of SEQ ID NOs: 40-43 are provided as SEQ ID NOs: 44-47, respectively. Each of SEQ ID NOs: 44-47 share at least 90% sequence identity to SEQ ID NO: 44, which is the F8R9-binding region of the meganuclease F8R 9-10x.70 (SEQ ID NO: 40). F8R10-binding regions of SEQ ID NOs: 40-43 are provided as SEQ ID NOs: 48-51, respectively. Each of SEQ ID NOs: 48-51 share at least 90% sequence identity to SEQ ID NO: 48, which is the F8R10-binding region of the meganuclease F8R 9-10x.70 (SEQ ID NO: 40).

4. Meganucleases that Recognize and Cleave the F8R 11-12 Recognition Sequence

Recombinant meganucleases (SEQ ID NOs: 52-55), collectively referred to herein as "F8R 11-12 meganucleases," were engineered to recognize and cleave the F8R 11-12 recognition sequence (SEQ ID NO: 13), which is present in the human and canine Factor VIII gene, specifically within the int22h-1 sequence. Each F8R 11-12 recombinant meganuclease comprises an N-terminal nuclease-localization signal derived from SV40, a first meganuclease subunit, a linker sequence, and a second meganuclease subunit. A first subunit in each F8R 11-12 meganuclease binds to the F8R11 recognition half-site of SEQ ID NO: 13, while a second subunit binds to the F8R12 recognition half-site (see, FIG. 2).

The F8R11-binding subunits and F8R12-binding subunits each comprise a 56 base pair hypervariable region, referred to as HVR1 and HVR2, respectively. F8R11-binding subunits are highly conserved outside of the HVR1 region. Similarly, F8R12-binding subunits are also highly conserved outside of the HVR2 region. The F8R11-binding regions of SEQ ID NOs: 52-55 are provided as SEQ ID NOs: 56-59, respectively. Each of SEQ ID NOs: 56-59 share at least 90% sequence identity to SEQ ID NO: 56, which is the F8R11-binding region of the meganuclease F8R 11-12x.56 (SEQ ID NO: 52). F8R12-binding regions of SEQ ID NOs: 52-55 are provided as SEQ ID NOs: 60-63, respectively. Each of SEQ ID NOs: 60-63 share at least 90% sequence identity to SEQ ID NO: 60, which is the F8R12-binding region of the meganuclease F8R 11-12x.56 (SEQ ID NO: 52).

5. Meganucleases that Recognize and Cleave the F8R 13-14 Recognition Sequence

Recombinant meganucleases (SEQ ID NOs: 64-67), collectively referred to herein as "F8R 13-14 meganucleases," were engineered to recognize and cleave the F8R 13-14 recognition sequence (SEQ ID NO: 15), which is present in the human and canine Factor VIII gene, specifically within the int22h-1 sequence. Each F8R 13-14 recombinant meganuclease comprises an N-terminal nuclease-localization signal derived from SV40, a first meganuclease subunit, a linker sequence, and a second meganuclease subunit. A first subunit in each F8R 13-14 meganuclease binds to the F8R13 recognition half-site of SEQ ID NO: 15, while a second subunit binds to the F8R14 recognition half-site (see, FIG. 2).

The F8R13-binding subunits and F8R14-binding subunits each comprise a 56 base pair hypervariable region, referred to as HVR1 and HVR2, respectively. F8R13-binding subunits are highly conserved outside of the HVR1 region. Similarly, F8R14-binding subunits are also highly conserved outside of the HVR2 region. The F8R13-binding regions of SEQ ID NOs: 64-67 are provided as SEQ ID NOs: 68-71, respectively. Each of SEQ ID NOs: 68-71 share at least 90% sequence identity to SEQ ID NO: 68, which is the F8R13-binding region of the meganuclease F8R 13-14x.13 (SEQ ID NO: 64). F8R14-binding regions of SEQ ID NOs: 64-67 are provided as SEQ ID NOs: 72-75, respectively. Each of SEQ ID NOs: 72-75 share at least 90% sequence identity to SEQ ID NO: 72, which is the F8R14-binding region of the meganuclease F8R 13-14x.13 (SEQ ID NO: 64).

6. Meganucleases that Recognize and Cleave the F8R 15-16 Recognition Sequence

Recombinant meganucleases (SEQ ID NOs: 76-79), collectively referred to herein as "F8R 15-16 meganucleases," were engineered to recognize and cleave the F8R 15-16 recognition sequence (SEQ ID NO: 17), which is present in the human and canine Factor VIII gene, specifically within the int22h-1 sequence. Each F8R 15-16 recombinant meganuclease comprises an N-terminal nuclease-localization signal derived from SV40, a first meganuclease subunit, a linker sequence, and a second meganuclease subunit. A first subunit in each F8R 15-16 meganuclease binds to the F8R15 recognition half-site of SEQ ID NO: 17, while a second subunit binds to the F8R16 recognition half-site (see, FIG. 2).

The F8R15-binding subunits and F8R16-binding subunits each comprise a 56 base pair hypervariable region, referred to as HVR1 and HVR2, respectively. F8R15-binding subunits are highly conserved outside of the HVR1 region. Similarly, F8R16-binding subunits are also highly conserved outside of the HVR2 region. The F8R15-binding regions of SEQ ID NOs: 76-79 are provided as SEQ ID NOs: 80-83, respectively. Each of SEQ ID NOs: 80-83 share at least 90% sequence identity to SEQ ID NO: 80, which is the F8R15-binding region of the meganuclease F8R 15-16x.14 (SEQ ID NO: 76). F8R16-binding regions of SEQ ID NOs: 76-79 are provided as SEQ ID NOs: 84-87, respectively. Each of SEQ ID NOs: 84-87 share at least 90% sequence identity to SEQ ID NO: 84, which is the F8R16-binding region of the meganuclease F8R 15-16x.14 (SEQ ID NO: 76).

7. Cleavage of F8R Recognition Sequences in a CHO Cell Reporter Assay

Figure 4:
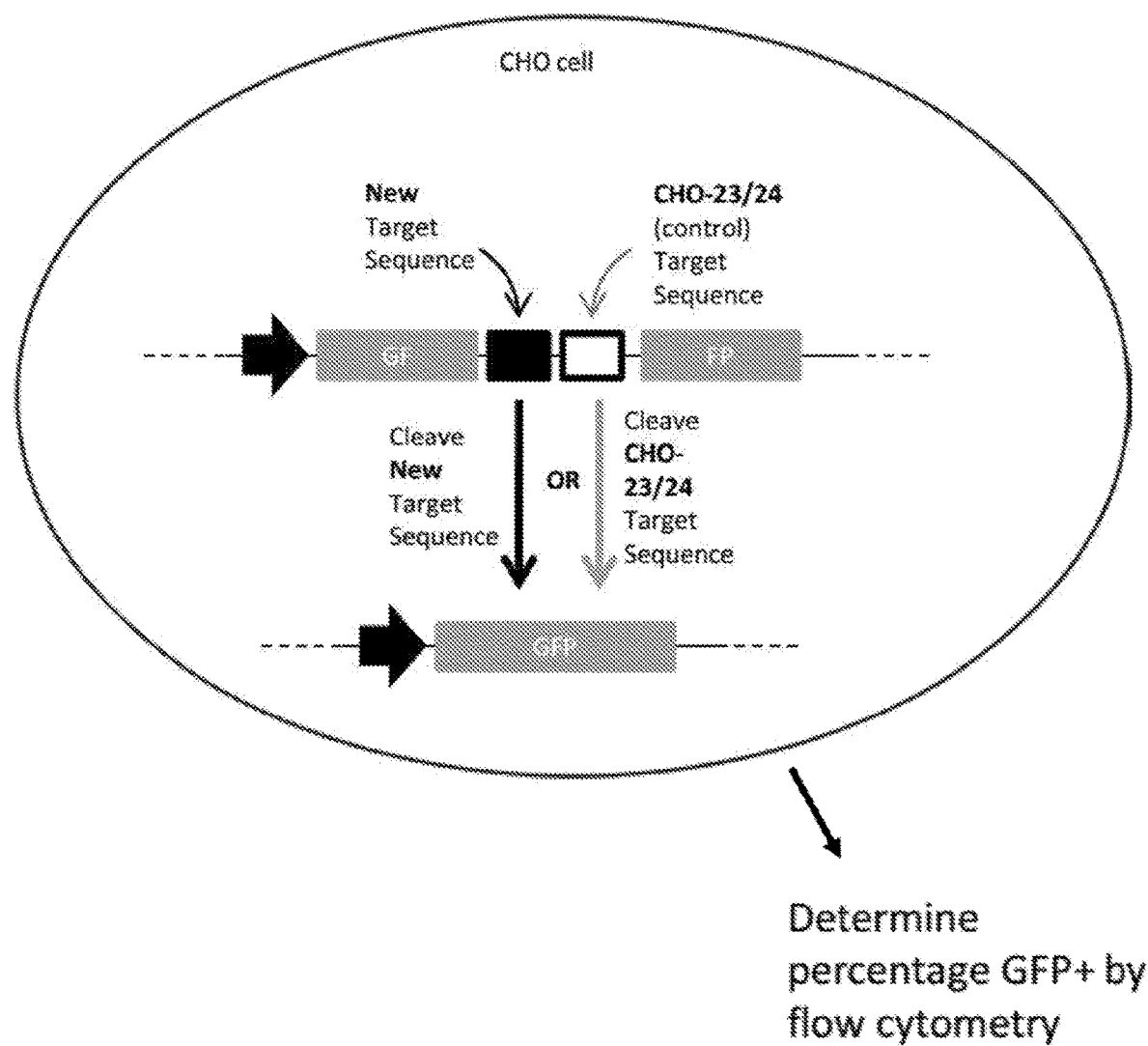
FIG. 4. Schematic of reporter assay in CHO cells for evaluating recombinant meganucleases targeting recognition sequences found in intron 22 of the Factor VIII gene. For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease of the invention (e.g., the F8R 1-2 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.
Figure 5A:
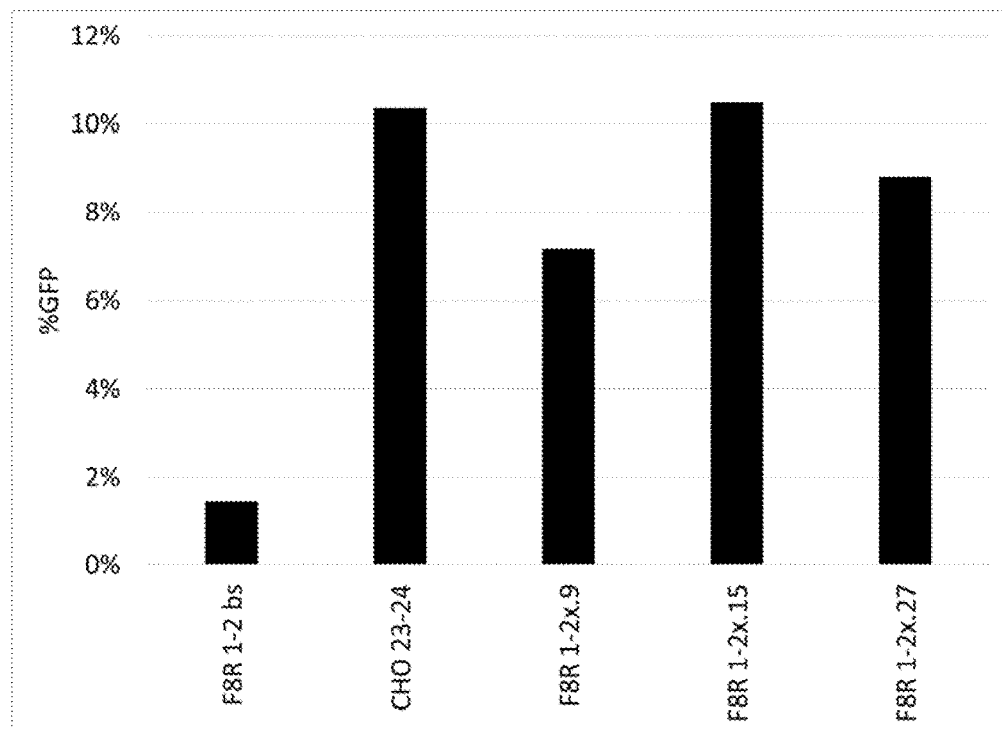
Figure 5B:
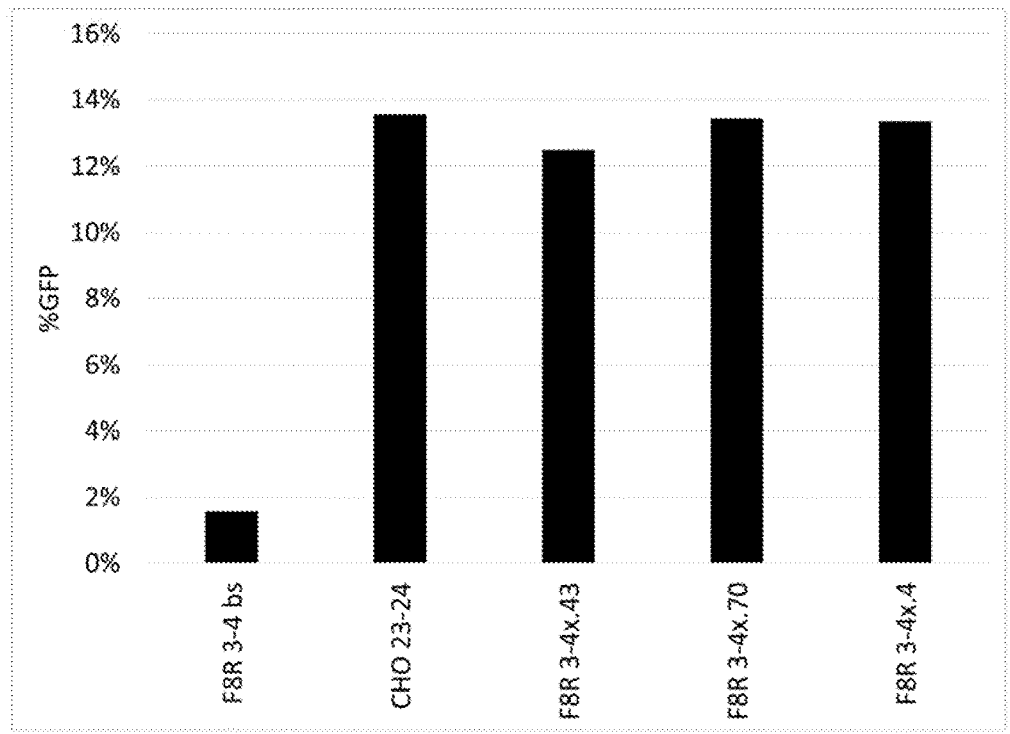
Figure 5C:
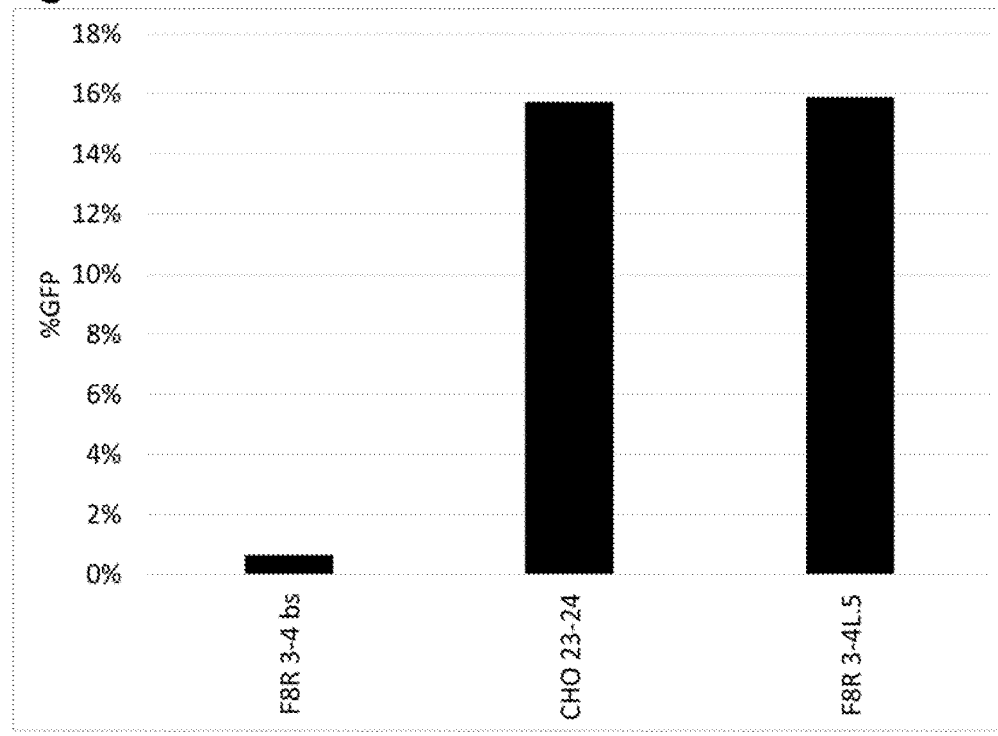
Figure 5D:
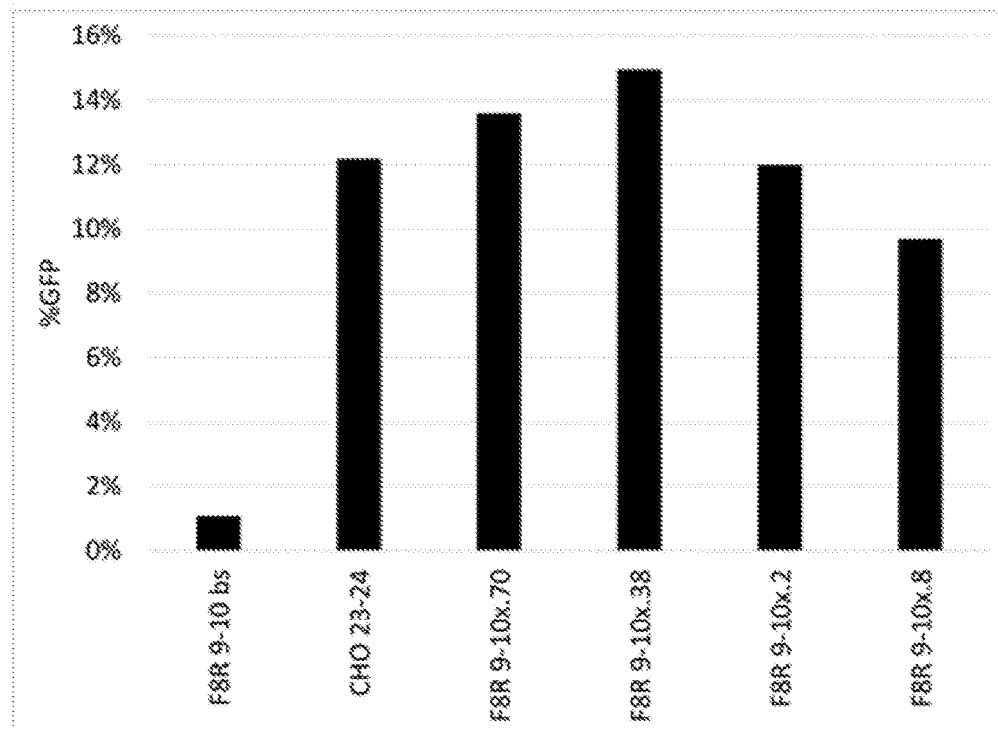
Figure 5E:
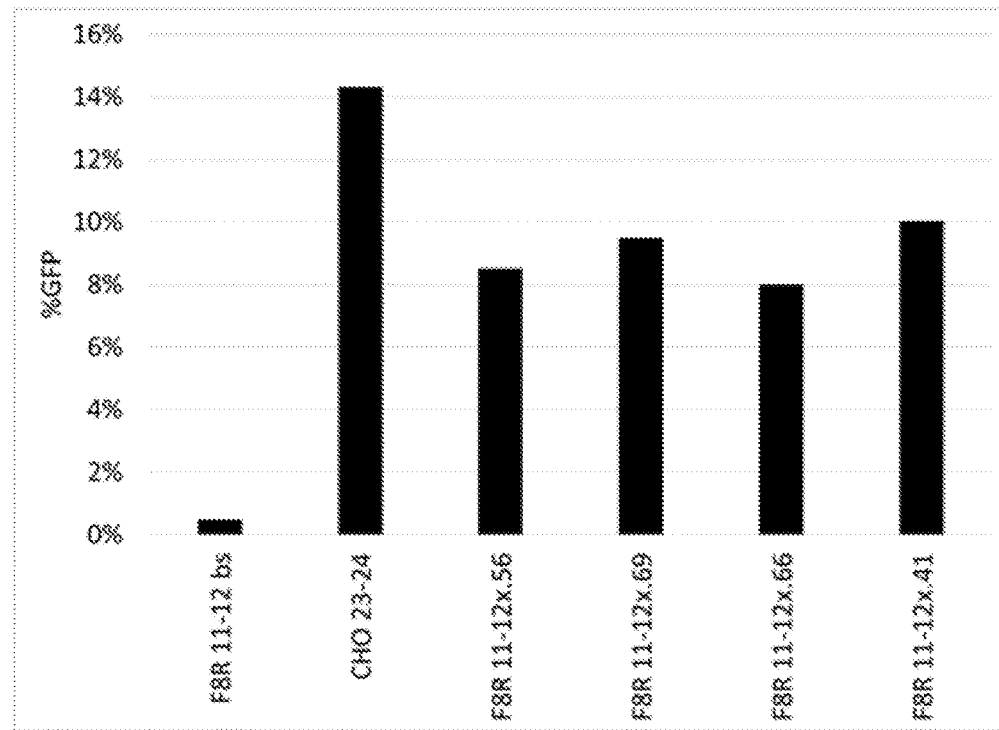
Figure 5F:
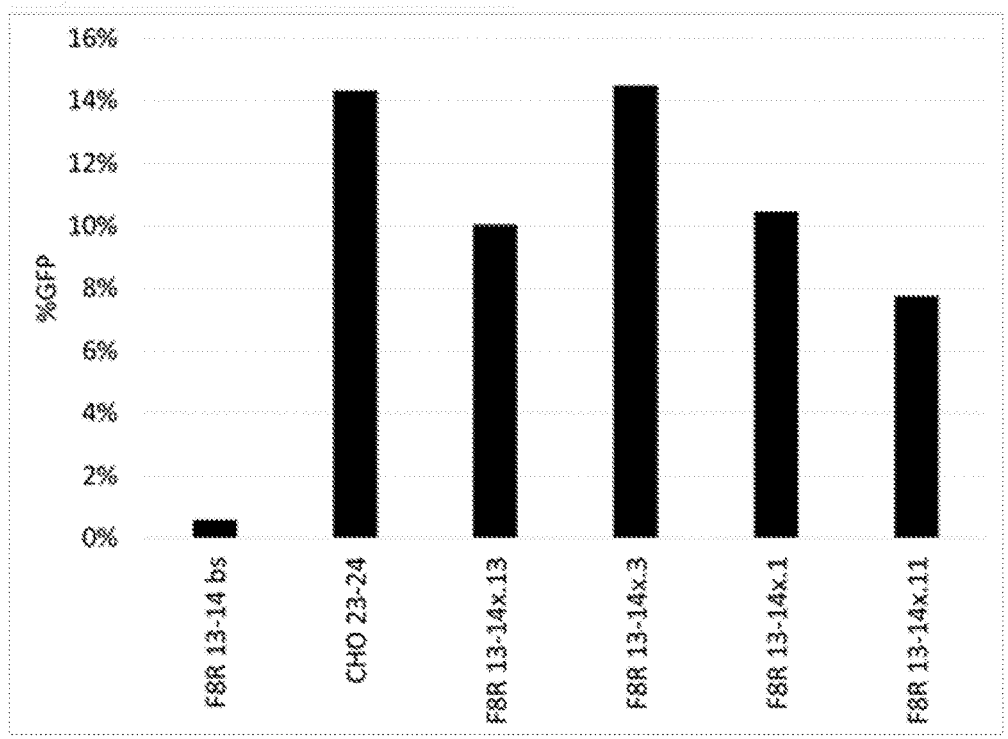
Figure 6A:
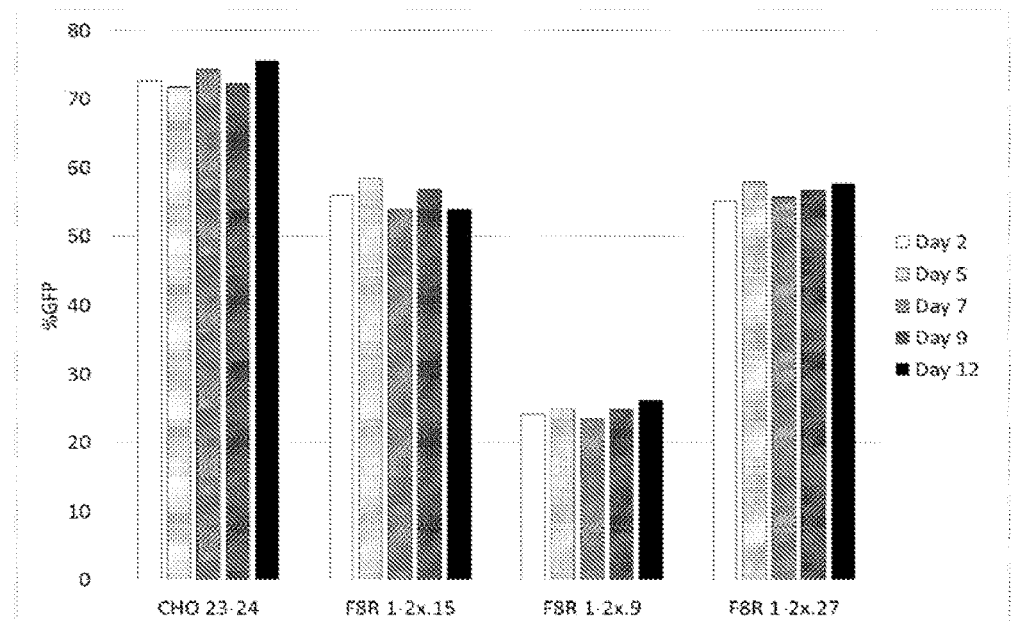
Figure 6B:
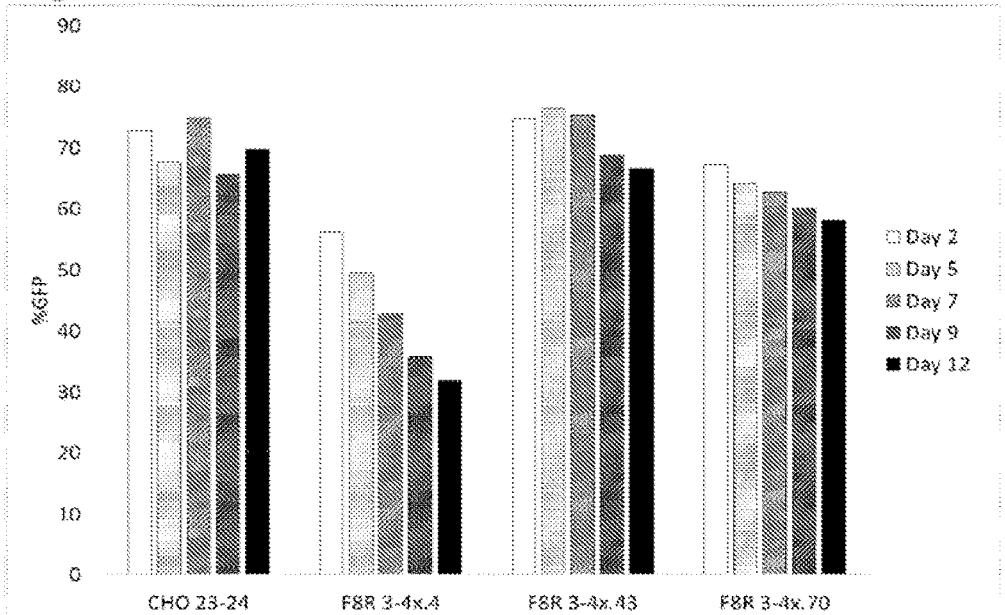
Figure 6C:
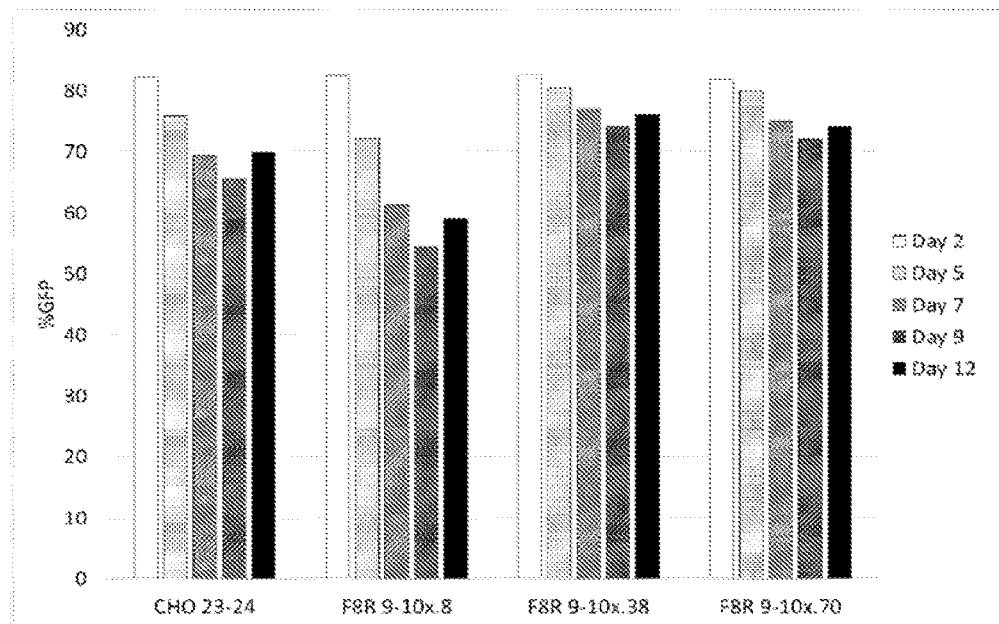
Figure 6D:
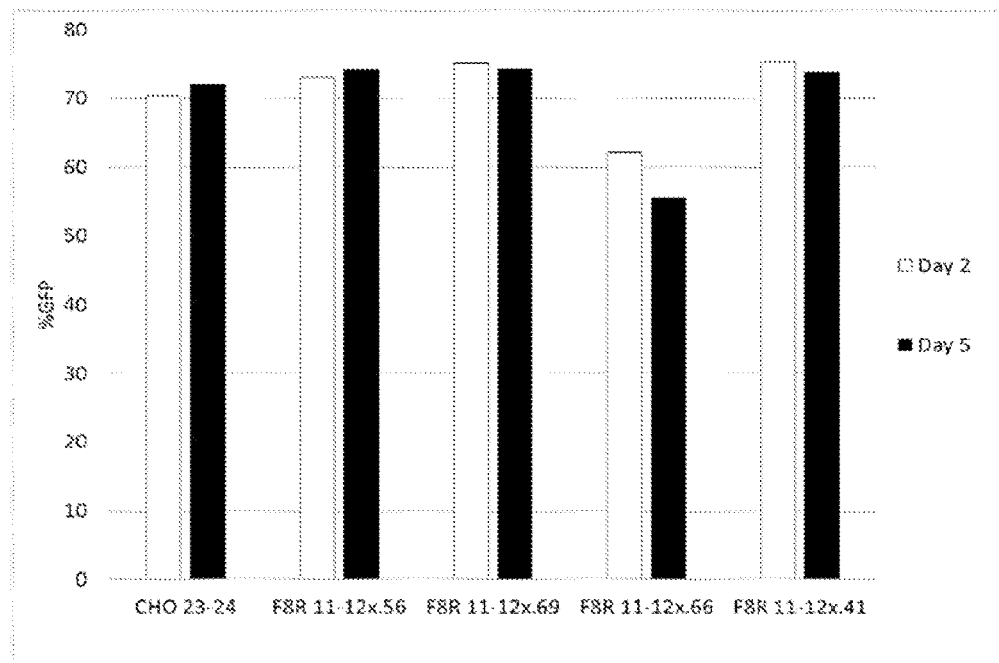

To determine whether F8R 1-2, F8R 3-4, F8R 9-10, F8R 11-12, F8R 13-14, and F8R 15-16 meganucleases could recognize and cleave their respective recognition sequences (SEQ ID NOs: 7, 9, 11, 13, 15, and 17, respectively), each recombinant meganuclease was evaluated using the CHO cell reporter assay previously described (see, WO/2012/167192 and FIG. 4). To perform the assays, CHO cell reporter lines were produced which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the F8R 1-2 recognition sequence (SEQ ID NO: 7), the F8R 3-4 recognition sequence (SEQ ID NO: 9), the F8R 9-10 recognition sequence (SEQ ID NO: 11), the F8R 11-12 recognition sequence (SEQ ID NO: 13), the F8R 13-14 recognition sequence (SEQ ID NO: 15), or the F8R 15-16 recognition sequence (SEQ ID NO: 17). The second recognition sequence inserted into the GFP gene was a CHO-23/24 recognition sequence, which is recognized and cleaved by a control meganuclease called "CHO-23/24". CHO reporter cells comprising the F8R 1-2 recognition sequence and the CHO-23/24 recognition sequence are referred to as "F8R 1-2 cells." CHO reporter cells comprising the F8R 3-4 recognition sequence and the CHO-23/24 recognition sequence are referred to as "F8R 3-4 cells." CHO reporter cells comprising the F8R 9-10 recognition sequence and the CHO-23/24 recognition sequence are referred to as "F8R 9-10 cells." CHO reporter cells comprising the F8R 11-12 recognition sequence and the CHO-23/24 recognition sequence are referred to as "F8R 11-12 cells." CHO reporter cells comprising the F8R 13-14 recognition sequence and the CHO-23/24 recognition sequence are referred to as "F8R 13-14 cells." CHO reporter cells comprising the F8R 15-16 recognition sequence and the CHO-23/24 recognition sequence are referred to as "F8R 15-16 cells."

CHO reporter cells were transfected with plasmid DNA encoding their corresponding recombinant meganucleases (e.g., F8R 1-2 cells were transfected with plasmid DNA encoding F8R 1-2 meganucleases) or encoding the CHO-23/34 meganuclease. In each assay, 4e5 CHO reporter cells were transfected with 50 ng of plasmid DNA in a 96-well plate using Lipofectamine® 2000 (ThermoFisher) according to the manufacturer's instructions. At 48 hours post-transfection, cells were evaluated by flow cytometry to determine the percentage of GFP-positive cells compared to an untransfected negative control (F8R bs). As shown in FIGS. 5A-5G, all F8R meganucleases were found to produce GFP-positive cells in cell lines comprising their corresponding recognition sequence at frequencies significantly exceeding the negative control.

The efficacy of PCS 7-8 meganucleases was also determined in a time-dependent manner 2, 5, 7, 9, and 12 days, after introduction of the meganucleases into CHO reporter cells. In this study, F8R 1-2, F8R 3-4, F8R 9-10, F8R 11-12, F8R 13-14, or F8R 15-16 cells ($1.0 \times 10^6$) were electroporated with $1 \times 10^6$ copies of their corresponding meganuclease mRNA per cell using a BioRad Gene Pulser Xcell™ according to the manufacturer's instructions. At the designated time points post-transfection, cells were evaluated by flow cytometry to determine the percentage of GFP-positive cells. A CHO-23/24 meganuclease was also included at each time point as a positive control.

As shown in FIGS. 6A-6F, the % GFP produced by a number of different F8R meganucleases was relatively consistent over the time course of each study, indicating persistent cleavage activity and a lack of any substantial toxicity in the cells. Other F8R meganucleases exhibited some variability in % GFP expression over the time course of the study.

8. Conclusions

These studies demonstrated that F8R meganucleases encompassed by the invention can efficiently target and cleave their respective recognition sequences in cells.

Example 2

Inversion of Exons 1-22 in the Human Factor VIII Gene

1. Production of Indels at Recognition Sequences in Mammalian Cells

Figure 7:
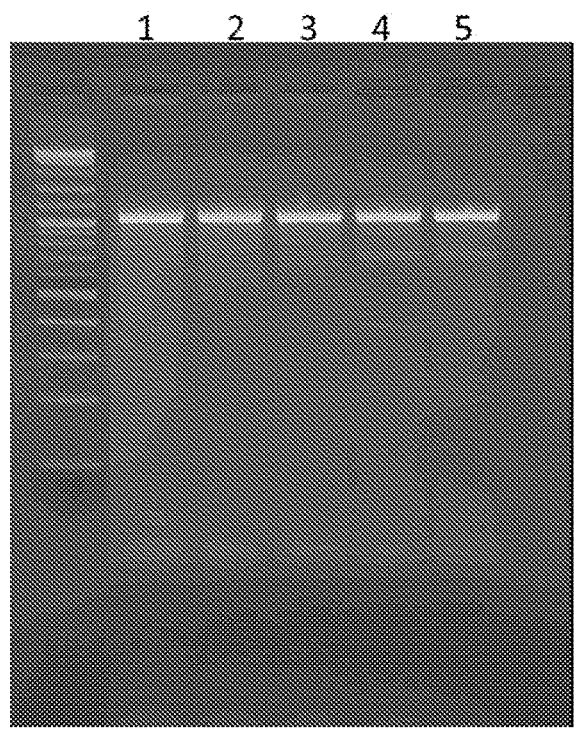
FIG. 7. Cleavage of F8R recognition sequences in mammalian cells. Meganucleases F8R 1-2 and F8R 3-4 were tested for the ability to cut and cause insertions and/or deletions (indels) at their recognition sites by T7 endonuclease assay in HEK 293 cells.

Meganucleases F8R 1-2 and F8R 3-4 were tested for the ability to cut and cause insertions and/or deletions (indels) at their recognition sites by T7 endonuclease assay. HEK 293 cells were transfected with 200 ng of mRNA encoding each nuclease. Cells were harvested at 7 days post transfection and gDNA was extracted. This gDNA was used as a template in PCR reactions using primers F8R3-4f.357 and F8R1-2r.467. The resulting PCR product was then analyzed using T7 endonuclease to reveal the presence of indels (FIG. 7). FIG. 7 illustrates an agarose gel loaded with PCR/T7 endonuclease reactions from HEK 293 cells that were mock treated (Lane 1) or treated with F8R 1-2x.15 (lane 2), F8R 1-2x.27 (lane 3), F8R 3-4x.43 (lane 4), or F8R 3-4x.70 (lane 5). The lower molecular weight bands in lanes 4 and 5 are indicative of a positive T7 endonuclease result and the presence of indels at the targeted recognition sequences.

2. Inversion of Exons 1-22 in Mammalian Cells

Figure 8A:
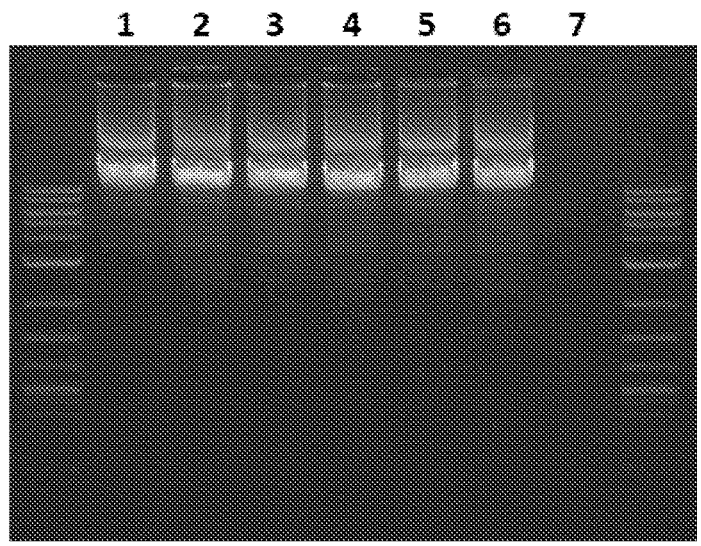
FIG. 8A and FIG. 8B. Inversion of exons 1-22 in the Factor VIII gene of mammalian cells. This experiment determined if cleavage of genomic DNA by F8R 1-2 and F8R 3-4 meganucleases could stimulate an inversion of exons 1-22 in the Factor VIII gene of HEK 293 cells. Genomic DNA was analyzed by PCR using a primer set which could detect normal positioning of exons 1-22 (H1R/H1F) or an inversion of exons 1-22 (H1R/H2/3R).
Figure 8B:
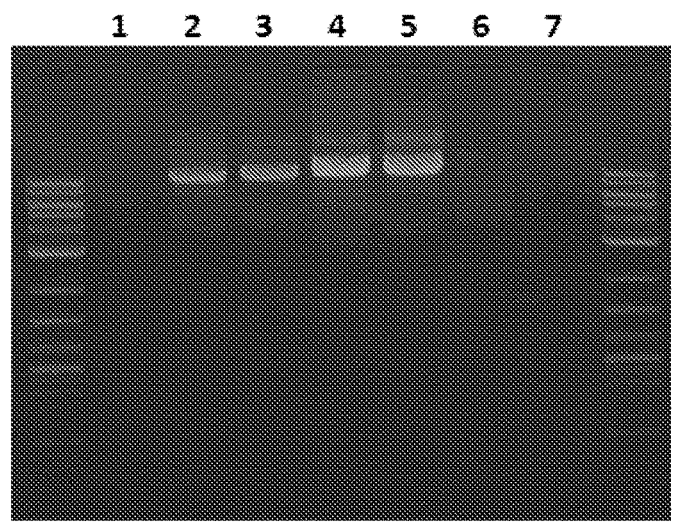

To determine if cleavage of genomic DNA by F8R 1-2 and F8R 3-4 meganucleases could stimulate an inversion of exons 1-22, we first transfected HEK 293 cells with 200 ng of mRNA encoding either F8R 1-2 or F8R 3-4 meganucleases and harvested gDNA 7 days later. The gDNA was analyzed by PCR using primer set H1R/H1F to detect normal exon 1-22 positioning and with primer set H1R/H2/3R to detect inverted exon 1-22 positioning (FIG. 8). FIG. 8A illustrates an agarose gel loaded with H1R/H1F primed PCR reactions from HEK 293 cells that were mock treated (lane 1), or treated with F8R 1-2x.15 (lane 2), F8R 1-2x.27 (lane 3), F8R 3-4x.43 (lane 4), F8R 3-4x.70 (lane 5). Lane 6 contains a control PCR using untreated human cell gDNA template. Lane 7 contains a no template PCR negative control. FIG. 8B illustrates an agarose gel loaded with H1R/H2/3R primed PCR reactions from HEK 293 cells that were mock treated (lane 1), or treated with F8R 1-2x.15 (lane 2), F8R 1-2x.27 (lane 3), F8R 3-4x.43 (lane 4), F8R 3-4x.70 (lane 5). Lane 6 contains a control PCR using untreated human cell gDNA template. Lane 7 contains a no template PCR negative control. The presence of PCR fragments in FIG. 8B is indicative of successful exon 1-22 inversion using F8R meganucleases encompassed by the invention.

Figure 9:
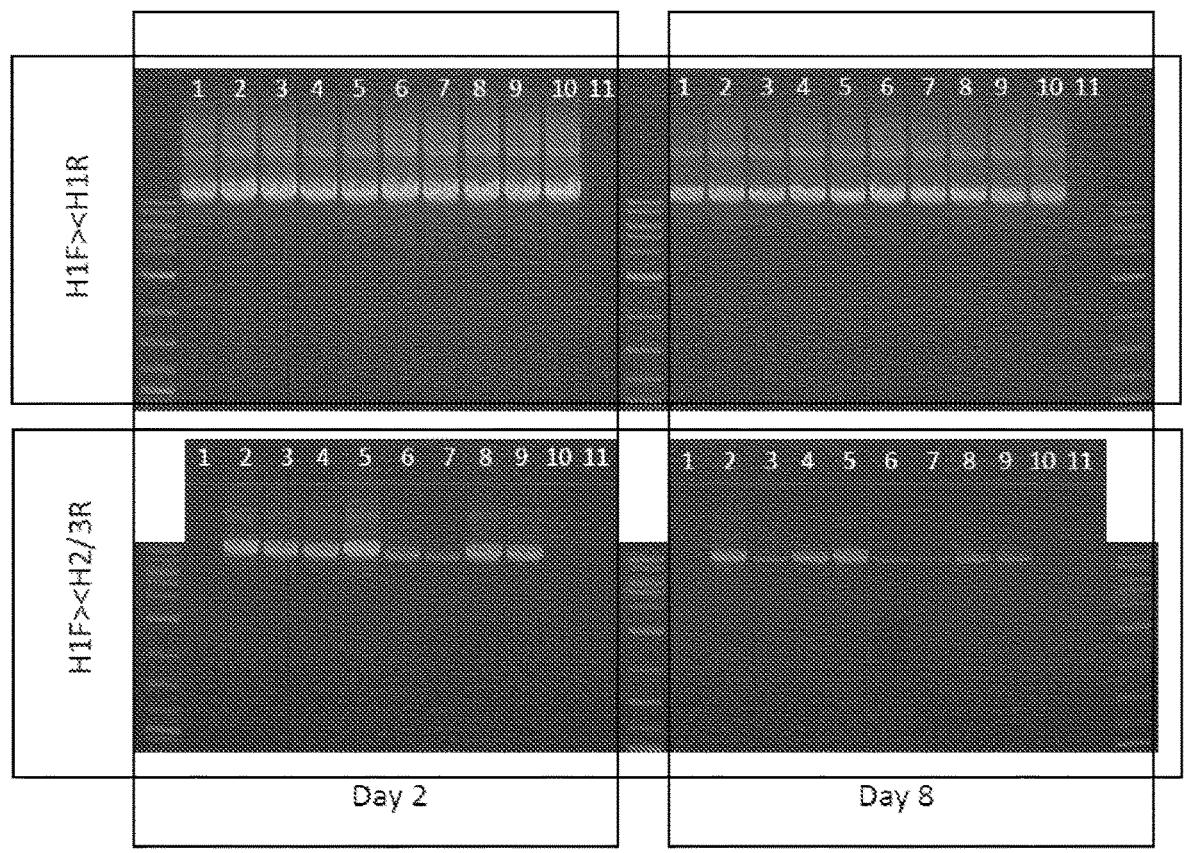
FIG. 9. Inversion of exons 1-22 in the Factor VIII gene of mammalian cells. This experiment determined if cleavage of genomic DNA by F8R 9-10, F8R 11-12, F8R 13-14, and F8R 15-16 meganucleases could stimulate an inversion of exons 1-22 in the Factor VIII gene of HEK 293 cells. Genomic DNA was analyzed by PCR using a primer set which could detect normal positioning of exons 1-22 (H1R/H1F) or an inversion of exons 1-22 (H1R/H2/3R). PCR analysis from day 2 and day 8 are provided for each primer set.

To determine if cleavage of genomic DNA by F8R 9-10, F8R 11-12, F8R 13-14, and F8R 15-16 meganucleases could stimulate an inversion of exons 1-22, we first transfected HEK 293 cells with 200 ng of mRNA encoding each individual nuclease and harvested gDNA at day 2 and day 8 post transfection. The gDNA was analyzed by PCR using primer set H1R/H1F, which detects normal exon 1-22 positioning, and with primer set H1R/H2/3R, which detects inverted exon 1-22 positioning (FIG. 9). FIG. 9 illustrates an agarose gel loaded with H1R/H1F primed PCR reactions (top) and H1R/H2/3R primed PCR reactions (bottom) from HEK 293 cells that were mock treated (lane 1), or treated with F8R 9-10x.38 (lane 2), F8R 9-10x.70 (lane 3), F8R 11-12x.56 (lane 4), F8R 11-12x.69 (lane 5), F8R 13-14x.3 (lane 6), F8R 13-14x.13 (lane 7), F8R 15-16x.14 (lane 8), or F8R 15-16x.85 (lane 9). Lane 10 contains a control PCR using untreated human cell gDNA template. Lane 11 contains a no template PCR negative control. The presence of PCR fragments in H1R/H2/3R primed PCR reactions (lower half of FIG. 9) is indicative of successful exon 1-22 inversion using the F8R meganucleases encompassed by the invention.

Example 3

Inversion of Factor VIII Gene by F8R Nucleases in 293 Cells and Determination of Efficiency by Inverse Digital PCR 1. Materials and Methods This study demonstrated that F8R nucleases encompassed by this invention can lead to the hemophilia A specific Factor VIII gene inversion in HEK293cells. In addition, the described method can be used to determine the efficiency of F8R nuclease-mediated Factor VIII gene inversion.

HEK293 cells (2×10^6) were transfected with mRNA (5 µg) encoding F8R11-12x.69 or F8R13-14x.13 nucleases, respectively, using a Bio-Rad GenePulser XCell according to the manufacturer's instructions. At 2 days post-transfection, genomic DNA was isolated from cells and inverse digital PCR was performed to determine Factor VIII genome editing. Genomic DNA isolated from untransfected cells served as a control.

Genomic DNA was digested to completion with restriction endonuclease Digested DNA was circularized using T4 DNA ligase and analyzed by inverse digital PCR using the Bio-Rad QX200 Digital PCR System according to the manufacturer's instructions. In normal human genomic DNA, the MI digest generates an approximately 21 kb fragment encompassing the int22h-1 repeat in intron 22 of the Factor VIII gene as well as an approximately 16 kb fragment encompassing a near-identical, inversely oriented copy of the int22h-1 repeat located about 0.5 Mb upstream of int22h-1.

In inverse digital PCR, the two circularized BclI fragments described above are amplified with primers flanking the respective BclI sites. Primers U1 and D1 bind upstream and downstream, respectively of the int22h-1 repeat in intron 22 of the Factor VIII gene; primer U3 binds upstream of a near-identical, inversely oriented copy of the int22h-1 repeat located about 0.5 Mb upstream of int22h-1. All primers bind the genomic DNA in opposite orientation to conventional PCR and generate amplicons only when the BclI fragments are circularized.

```
U1:
                                  (SEQ ID NO: 88)
[5'-CCTTTCAACTCCATCTCCAT-3']

D1:
                                  (SEQ ID NO: 89)
[5'-ACATACGGTTTAGTCACAAGT-3']

U3:
                                  (SEQ ID NO: 90)
[5'-TCCAGTCACTTAGGCTCAG-3']
```

Inverse digital PCR of HEK293 genomic DNA with primers U1/D1 yields an approximately 0.5 kb amplicon that can be detected using a TaqMan probe while PCR with primers U3/U1 does not generate an amplification product.

Upon successful inversion of the genomic fragment between int22h-1 and its distal copy, the U1 primer binding site, which is located on the inverted fragment, is reoriented relative to the D1 and U3 primer binding sites. Now, the U1/D1 PCR fails to generate a PCR product, while the U3/U1 PCR yields an approximately 0.5 kb amplicon which can be detected with the same TaqMan probe.

2. Results

Figure 10:
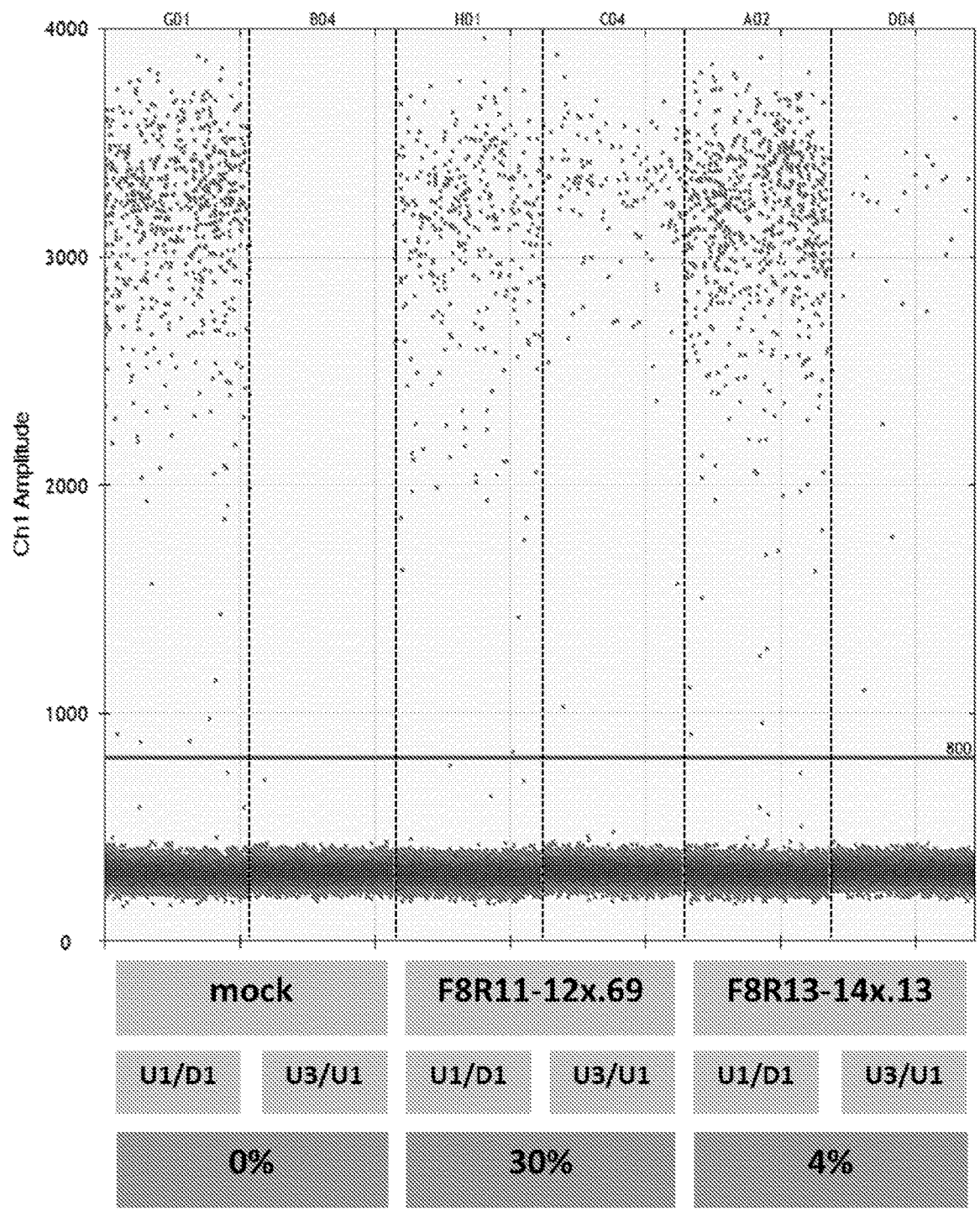
FIG. 10. Inversion of Factor VIII gene by F8R nucleases in 293 cells and determination of efficiency by inverse digital PCR. HEK293 cells were transfected with mRNA encoding F8R11-12x.69 or F8R13-14x.13 nucleases, respectively. At 2 days post-transfection, genomic DNA was isolated from cells and inverse digital PCR was performed to determine Factor VIII genome editing.

Genomic DNAs from HEK293 cells and HEK293 cells treated with F8R11-12x.69 or F8R13-14x.13 nucleases, respectively, were analyzed by inverse digital PCR. Only the U1/D1 fragment was amplified from genomic DNA isolated from untreated HEK293 cells, while the U3/U1 PCR did not generate a signal (FIG. 10, mock). Using genomic DNA from F8R nuclease-treated HEK293 cells, both U1/D1 and U3/U1 amplicons were detected (FIG. 10, F8R11-12x.69 and F8R13-14x.13). The U1/D1 fragment was still amplified from genomic DNA from F8R nuclease-treated HEK293 cells because the nuclease treatment generated a mixed population of cells with both edited and unedited genomes. Since digital PCR allows parallel analysis of hundreds to thousands of chromosome equivalents, the Factor VIII gene inversion efficiency could be be calculated. Out of the total number of Factor VIII genes detected by this assay, 4% and 30% showed an inversion as a result of the activity of nucleases F8R13-14x.13 and F8R11-12x.69, respectively.

3. Conclusions

Inverse digital PCR detected Factor VIII gene inversion in HEK293 cells treated with nucleases F8R11-12x.69 and F8R13-14x.13. In addition, using inverse digital PCR, the editing efficiency could be calculated. Depending on the nuclease (F8R11-12x.69), up to 30% of the detected Factor VIII genes in HEK293 cells were edited. Importantly, this study demonstrates that Factor VIII gene inversions can be induced by DNA double-strand breaks within the int22h repeats. Both nucleases target recognition sequences within the int22h repeats and potentially introduce up to three double-strand breaks per chromosome.

Example 4

Inversion of Factor VIII Gene by F8R Nucleases in Primary Human T Cells and Determination of Editing by Long-Distance PCR 1. Materials and Methods This study demonstrated that F8R nucleases encompassed by this invention can lead to the hemophilia A specific Factor VIII gene inversion in normal wild-type human T-cells. Normal human T-cells (1×10^6) were transfected with mRNA (1 µg) encoding F8R3-4x.43 nuclease using a Lonza 4D nucleofector according to the manufacturer's instructions. At 3 days post-transfection, genomic DNA was isolated from cells and long-distance PCR was performed to determine Factor VIII genome editing. Genomic DNA isolated from untransfected normal human T-cells served as a control.

In this long-distance PCR, the genomic DNA was amplified between primers FWD1/REV1 and FWD3/FWD1, respectively.

FWD1:
(SEQ ID NO: 91)
[5'-CCCTTACAGTTATTAACTACTCTCATGAGG1TCATTCC-3']

REV1:
(SEQ ID NO: 92)
[5'-CCCCGGCACTTGAAAGTAGCAGATGCAAGAAGGGCACA-3']

FWD3:
(SEQ ID NO: 93)
[5'-ACTATAACCAGCACCTTGAACTTCCCCTCTCATA-3']

Primers FWD1 and REV1 bind upstream and downstream, respectively of the int22h-1 repeat in intron 22 of the Factor VIII gene; primer FWD3 binds upstream of a near-identical, inversely oriented copy of the int22h-1 repeat located about 0.5 Mb upstream of int22h-1.

Long-distance PCR of normal human genomic DNA with primers FWD1/REV1 yields an approximately 10 kb amplicon while PCR with primers FWD3/FWD1 does not generate an amplification product.

Upon successful inversion of the genomic fragment between int22h-1 and its distal copy, the FWD1 primer binding site, which is located on the inverted fragment, is reoriented relative to the REV1 and FWD3 primer binding sites. Now, the FWD1/REV1 PCR fails to generate a PCR product while the FWD3/FWD1 PCR yields an approximately 9.7 kb amplicon. PCR fragments are analyzed by agarose gel electrophoresis and visualized by ethidium bromide.

2. Results

Figure 11:
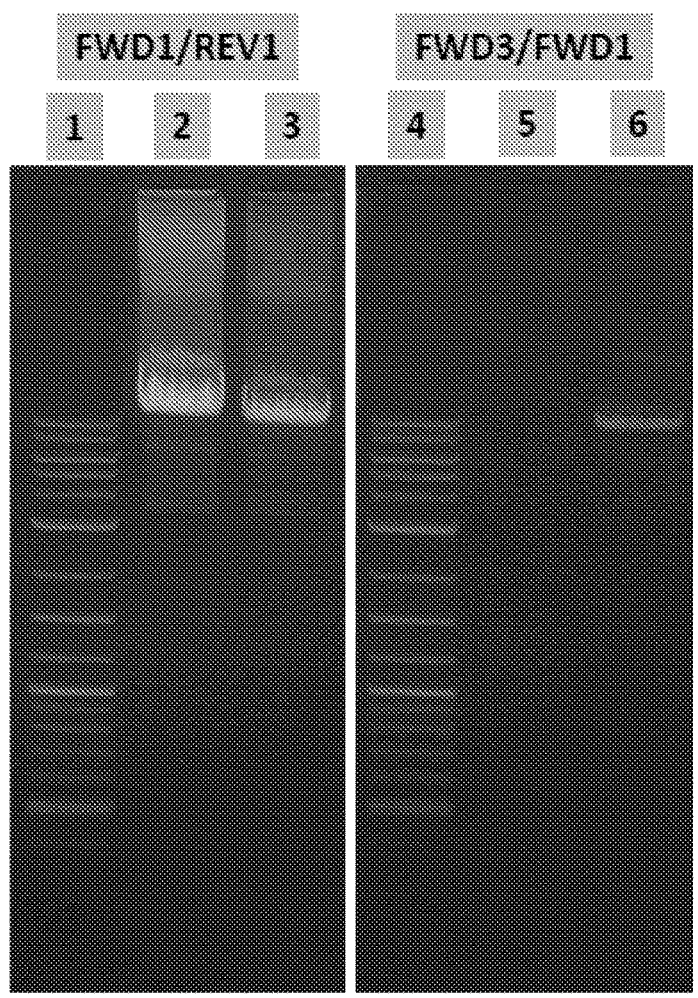
FIG. 11. Inversion of Factor VIII gene by F8R nucleases in primary human T cells and determination of editing by long-distance PCR. Normal human T-cells were transfected with mRNA encoding the F8R3-4x.43 nuclease. At 3 days post-transfection, genomic DNA was isolated from cells and long-distance PCR was performed to determine Factor VIII genome editing.

Genomic DNAs from normal human T-cells and normal human T-cells treated with F8R3-4x.43 nuclease were analyzed by long-distance PCR (FIG. 11). Only the FWD1/REV1 fragment was be amplified from genomic DNA isolated from untreated normal human T-cells (lanes 2 and 5). Using genomic DNA from F8R3-4x.43 nuclease-treated normal human T-cells as PCR template, both FWD1/REV1 and FWD3/FWD1 primer combinations yield their signature ~10 kb and ~9.7 kb amplicons, respectively (lanes 3 and 6). The FWD1/REV1 fragment can still be amplified from genomic DNA from F8R3-4x.43 treated normal human T-cells because the nuclease treatment generated a mixed population of cells with edited and unedited genomes.

3. Conclusions

The F8R3-4x.43 meganuclease was able to generate an inversion of the Factor VIII gene in human T cells by producing a double strand break within the int22h regions, and this inversion could be detected by long-distance PCR.

Example 5

Reversion of Factor VIII Gene by F8R Nucleases in Primary Human Patient T Cells and Determination of Editing by Long-Distance PCR 1. Materials and Methods This study demonstrated that F8R nucleases encompassed by this invention can lead to the reversion of the hemophilia A specific Factor VIII gene inversion in hemophilia A patient T-cells.

Hemophilia A patient T-cells (1×10^6) were transfected with mRNA (1 µg) encoding F8R3-4x.43, F8R11-12x.69, or F8R15-16x.14 nucleases, respectively, using a Lonza 4D nucleofector according to the manufacturer's instructions. At 3 days post-transfection, genomic DNA was isolated from cells and long-distance PCR was performed to determine Factor VIII genome editing. Genomic DNA isolated from patient T-cells transfected with mRNA encoding green fluorescent protein (GFP) served as a control.

In this long-distance PCR, the genomic DNA was amplified between primers H1U/H1D and H3D/H1D, respectively.

H1U:

(SEQ ID NO: 94)
[5'-GCCCTGCCTGTCCATTACACTGATGACATTATGCTGAC-3']

H1D:

(SEQ ID NO: 95)
[5'-GGCCCTACAACCATTCTGCCTTTCACTTTCAGTGCAATA-3']

H3D:

(SEQ ID NO: 96)
[5'-CACAAGGGGGAAGAGTGTGAGGGTGTGGGATAAGAA-3']

Primers H1U and H1D bind upstream and downstream, respectively of the int22h-1 repeat in intron 22 of the Factor VIII gene; primer H3D binds downstream of a near-identical, inversely oriented copy of the int22h-1 repeat located about 0.5 Mb upstream of int22h-1.

Long-distance PCR of normal human genomic DNA with primers H1U/H1D yields an approximately 12 kb amplicon while PCR with primers H3D/H1D does not generate an amplification product. Conversely, long-distance PCR of genomic DNA from patient cells with the hemophilia A gene inversion with primers H1U/H1D fails to generate a PCR product while the H3D/H1D PCR yields an approximately 11 kb amplicon.

Upon successful reversion of the genomic fragment in patient T-cells between two inversely oriented int22h repeats, the H1U primer binding site, which is located on the inverted fragment, is reoriented relative to the H3U and H1D primer binding sites. Now the H1U/H1D PCR yields the 12 kb amplicon, indicating a reversion to the wild-type configuration of the Factor VIII gene. PCR fragments were analyzed by agarose gel electrophoresis and visualized by ethidium bromide.

2. Results

Genomic DNAs from hemophilia A patient T-cells treated with mRNA encoding F8R3-4x.43, F8R11-12x.69, or F8R15-16x.14 nucleases (or GFP as a control) were analyzed by long-distance PCR (FIG. 12). Only the H3/H1D fragment could be amplified from genomic DNA isolated from patient T-cells treated with GFP mRNA (lanes 1a and 1b). Using genomic DNA from F8R3-4x.43, F8R11-12x.69, or F8R15-16x.14 nuclease-treated patient T-cells as PCR template, both H1U/H1D and H3D/H1D primer combinations yielded their signature wild-type (~12 kb) and inversion (~11 kb) amplicons, respectively (lanes 3a and 3b: F8R3-4x.43; lanes 4a and 4b: F8R11-12x.69; lanes 5a and 5b: F8R15-16x.14). The H3U/H1D fragment was still being amplified from genomic DNA from F8R nuclease-treated patient T-cells because the nuclease treatment generated a mixed population of cells with edited and unedited genomes.

3. Conclusions

F8R meganucleases encompassed by the invention were capable of inducing a reversion of the inverted Factor VIII gene back to a wild-type configuration in hemophilia A patient T-cells in vitro, and this reversion could be detected by long-distance PCR.

The invention claimed is:

1. A method for genetically-modifying a Factor VIII gene in the genome of a mammalian cell to generate a reversion of exons 1-22, wherein said mammalian cell comprises an inversion of exons 1-22 in the Factor VIII gene compared to a wild-type Factor VIII gene, said method comprising delivering to said mammalian cell a nucleic acid encoding an engineered nuclease having specificity for a recognition sequence positioned within an int22h-1 sequence of a Factor VIII gene, wherein said engineered nuclease is expressed in said mammalian cell;
wherein said engineered nuclease cleaves said recognition sequence and generates a reversion of exons 1-22 to a wild-type orientation in said genetically-modified mammalian cell.

2. The method of claim 1, wherein said genetically-modified cell produces a functional Factor VIII protein following said reversion of exons 1-22 to a wild-type orientation.

3. The method of claim 1, wherein said recognition sequence is within an F8A1 coding sequence of said Factor VIII gene.

4. The method of claim 3, wherein said F8A1 coding sequence has at least 95% sequence identity to SEQ ID NO: 5.

5. The method of claim 1, wherein said nucleic acid is delivered to said mammalian cell using an mRNA.

6. The method of claim 1, wherein said nucleic acid is delivered to said mammalian cell using a DNA construct.

7. The method of claim 1, wherein said nucleic acid is delivered to said mammalian cell using a viral vector.

8. The method of claim 7, wherein said viral vector is a recombinant AAV vector.

9. The method of claim 1, wherein said engineered nuclease is an engineered meganuclease, a TALEN, a zinc finger nuclease, a compact TALEN, a CRISPR, or a megaTAL.

10. The method of claim 9, wherein said engineered nuclease is an engineered meganuclease.

11. The method of claim 1, wherein said mammalian cell is a hepatic sinusoidal endothelial cell or a progenitor cell capable of differentiating into a hepatic sinusoidal endothelial cell.

12. The method of claim 1, wherein said mammalian cell is a human cell.

13. The method of claim 12, wherein said int22h-1 sequence of said Factor VIII gene has at least 95% sequence identity to SEQ ID NO: 3.

14. The method of claim 1, wherein said mammalian cell is a canine cell.

15. The method of claim 14, wherein said int22h-1 sequence of said Factor VIII gene has at least 95% sequence identity to SEQ ID NO: 4.

16. The method of claim 1, wherein said recognition sequence comprises the nucleic acid sequence of SEQ ID NO: 9.

* * * * *